US00RE42804E

(19) United States
(12) Reissued Patent
Dedig et al.

(10) Patent Number: US RE42,804 E
(45) Date of Reissued Patent: Oct. 4, 2011

(54) INJECTOR SYSTEMS AND SYRINGE ADAPTERS FOR USE THEREWITH

(75) Inventors: James Albert Dedig, Pittsburgh, PA (US); Thomas P. Joyce, Wilkins Township, PA (US); Michael A. Spohn, Butler, PA (US); John A. Haury, Sewickley, PA (US)

(73) Assignee: MEDRAD, Inc., Indianola, PA (US)

(21) Appl. No.: 12/187,610

(22) Filed: Aug. 7, 2008

Related U.S. Patent Documents

Reissue of:
(64) Patent No.: 6,726,657
Issued: Apr. 27, 2004
Appl. No.: 09/633,299
Filed: Aug. 8, 2000

U.S. Applications:
(63) Continuation-in-part of application No. 09/365,285, filed on Jul. 30, 1999, now abandoned.

(51) Int. Cl.
*A61M 1/00* (2006.01)
(52) U.S. Cl. ..... 604/152; 604/131
(58) Field of Classification Search ..... 604/151–154, 604/67, 65, 131, 118, 189
See application file for complete search history.

(56) References Cited

U.S. PATENT DOCUMENTS 3,880,163 A * 4/1975 Ritterskamp ..... 604/136
4,006,736 A * 2/1977 Kranys et al. ..... 600/432
4,067,479 A 1/1978 Moline
4,342,312 A * 8/1982 Whitney et al. ..... 604/28
4,465,473 A * 8/1984 Ruegg ..... 604/154
4,563,175 A * 1/1986 LaFond ..... 604/155
4,650,465 A * 3/1987 Langer et al. ..... 604/65
(Continued)

FOREIGN PATENT DOCUMENTS

EP 0346950 12/1989
(Continued)

OTHER PUBLICATIONS

Liebel-Flarsheim Company, Angiomat 6000 Digital Injection System Operator's Manual, 600950 Rev.1 (1990), pp. 3-6 to 3-8, 4-52 to 4-56.

(Continued)

*Primary Examiner* — Manuel A Mendez
(74) *Attorney, Agent, or Firm* — David Schramm

(57) ABSTRACT

An adapter includes a syringe carrier adapted to seat at least a portion of the syringe. The syringe carrier includes at least one rearward facing abutmer member to abut at least one forward facing surface on a syringe. The syringe carrie includes an opening therein to allow a drive member of an injector to communicate forward force to the plunger through abutment without connective engagement between the drive member and the plunger. The adapter further includes a releasable mounting mechanism positioned to the rear of the syringe carrier to mount the adapter in a desired position relative to the front wall of the injector. An adapter includes a first section and a second section that are rotatable relative to each other about a hinge axis generally perpendicular to a longitudinal axis of the adapter. An adapter includes a first section and a second section that are generally the same in construction, the first section and the section being connectable to form a syringe carrier to seat at least a portion of the syringe.

35 Claims, 43 Drawing Sheets

U.S. PATENT DOCUMENTS

| | | | | | |
|---|---|---|---|---|---|
| 4,671,790 | A | | 6/1987 | Nishi | |
| 4,677,980 | A | * | 7/1987 | Reilly et al. | 600/432 |
| 4,695,271 | A | * | 9/1987 | Goethel | 604/506 |
| 4,978,335 | A | * | 12/1990 | Arthur, III | 604/67 |
| 5,026,349 | A | | 6/1991 | Schmitz et al. | |
| 5,254,096 | A | | 10/1993 | Rondelet et al. | |
| 5,269,762 | A | * | 12/1993 | Armbruster et al. | 604/155 |
| 5,279,569 | A | * | 1/1994 | Neer et al. | 604/154 |
| 5,300,031 | A | * | 4/1994 | Neer et al. | 604/154 |
| 5,322,511 | A | * | 6/1994 | Armbruster et al. | 604/155 |
| 5,383,858 | A | | 1/1995 | Reilly et al. | |
| 5,456,670 | A | | 10/1995 | Neer et al. | |
| 5,494,036 | A | | 2/1996 | Uber, III et al. | |
| 5,520,653 | A | | 5/1996 | Reilly et al. | |
| 5,535,746 | A | | 7/1996 | Hoover et al. | |
| 5,545,140 | A | | 8/1996 | Conero et al. | |
| 5,662,612 | A | | 9/1997 | Niehoff | |
| 5,681,286 | A | | 10/1997 | Niehoff | |
| 5,741,232 | A | | 4/1998 | Reilly et al. | |
| 5,779,675 | A | | 7/1998 | Reilly et al. | |
| 5,795,333 | A | | 8/1998 | Reilly et al. | |
| 5,865,805 | A | | 2/1999 | Ziemba | |
| 5,873,861 | A | | 2/1999 | Hitchins et al. | |
| 5,899,885 | A | | 5/1999 | Reilly et al. | |
| 5,913,844 | A | | 6/1999 | Ziemba et al. | |
| 5,928,197 | A | | 7/1999 | Niehoff | |
| 5,938,639 | A | | 8/1999 | Reilly et al. | |
| 5,944,694 | A | | 8/1999 | Hitchins et al. | |
| 5,947,929 | A | | 9/1999 | Trull | |
| 5,997,502 | A | | 12/1999 | Reilly et al. | |
| 6,080,136 | A | | 6/2000 | Trull et al. | |
| 6,082,597 | A | | 7/2000 | Beckett et al. | |
| 6,241,708 | B1 | | 6/2001 | Reilly et al. | |

FOREIGN PATENT DOCUMENTS

| | | |
|---|---|---|
| EP | 0561122 | 9/1993 |
| EP | 0567186 | 10/1993 |
| JP | 9-122234 | 5/1991 |
| JP | 8-336592 | 12/1996 |
| WO | WO95/20410 | 3/1995 |
| WO | WO95/26211 | 10/1995 |
| WO | WO97/36635 | 9/1997 |
| WO | 99/10032 | 3/1999 |
| WO | 01/08727 | 2/2001 |

OTHER PUBLICATIONS

Liebel-Flarsheim Company, Angiomat 6000 Contrast Delivery System Brochure (1992).

Drawing of Dual Flange Injector Head (publicly disclosed in Jul. 1995).

Medrad MCT/MCT Plus Operation Manual, KMP 810P Revision B (1991), pp. 4-18 to 4-22 and 6-1 to 6-13.

Liebel-Flarsheim Company, Angiomat CT Digital Injection System Operator's Manual, 600964 (1990), pp. 1-3 to 1-4, 3-7 to 3-9, 4-37 to 4-39.

Liebel-Flarsheim Company, Angiomat CT Digital Injection System Operator's Manual, 600964 Rev. A (1991) pp. 1-5, 3-12, 4-48 to 4-51.

Liebel-Flarsheim Company, CT 9000 ADV Digital Injection System Manual 800961-B, Feb. 1998 pp. 1-4 to 1-16.

International Search Report for Counterpart PCT Application No. PCT/US 00/20623.

Plaintiff's, Tyco Healthcare Group LP, Mallinckrodt Inc., and Liebel-Flarsheim Company, Second Supplemental Preliminary Invalidity Contentions filed Dec. 11, 2006.

Plaintiff's, Tyco Healthcare Group LP, Mallinckrodt Inc., and Liebel-Flarsheim Company, Supplemental Preliminary Invalidity Contentions filed Mar. 3, 2006.

Defendant Medrad, Inc.'s Second Amended Answer and Counterclaims filed Jan. 5, 2006.

Plaintiff's Reply to Defendant's Second Amended Counterclaims filed Jan. 27, 2006.

Medrad, Inc.'s Reply to Plaintiff's Counterclaims filed Feb. 16, 2006.

Japanese Sonic Shot 50 Operations Manual (1998).

Mallinckrodt's Optistar MR Digital Injection System,Operator's Manual 801900-A (Nov. 1999).

* cited by examiner

INJECTOR SYSTEMS AND SYRINGE ADAPTERS FOR USE THEREWITH

Matter enclosed in heavy brackets [ ] appears in the original patent but forms no part of this reissue specification; matter printed in italics indicates the additions made by reissue.

RELATED APPLICATION

The present application is a continuation-in-part application of pending U.S. patent application Ser. No. 09/365,285 filed Jul. 30, 1999, the disclosure of which is incorporated herein by reference.

FIELD OF THE INVENTION

The present invention relates to powered injector systems and syringe adapters for use therewith.

BACKGROUND OF THE INVENTION

A number of injector-actuated syringes and powered injectors for use in medical procedures such as angiography, computed tomography, ultrasound and NMRIMRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

As discussed in U.S. Pat. No. 5,383,858, a syringe used with a front-loading injector preferably includes a readily releasable mounting mechanism for securing the syringe to the front wall of the injector. The use of specifically designed mounting mechanisms, however, prevents the use of syringes of other various types with front-loading injectors. Such syringes may, for example, include a syringe body, a plunger reciprocally mounted therein, and a plunger extension for transfer of force to the plunger.

U.S. Pat. No. 5,520,653, the disclosure of which is incorporated herein by reference, discloses several adapters designed to allow the use of various syringes with a front-loading injector. In one embodiment, the adapter of U.S. Pat. No. 5,520,653 includes a syringe carrier having a front end, a rear end, and syringe retaining channel located between the carrier front and rear ends for engaging at least a portion of the syringe flange. Mounting flanges near the rearward end of the carrier lo releasably mount the carrier in a desired position relative to the front wall of the injector. The adapter of U.S. Pat. No. 5,520,653 further includes a follower reciprocally mounted within the carrier. The follower has a front end that engages the syringe plunger extension when the syringe is installed in the carrier. A drive head opening in the carrier communicates with a pair of drive head slots positioned near the rear end of the follower for releasably mounting the follower in a desired position relative to the drive head of the injector.

Although U.S. Pat. No. 5,520,653 is a substantial improvement in the art, it remains desirable to develop improved adapters for use with syringes of various types to permit use of such syringes with front-loading injectors.

SUMMARY OF THE INVENTION

In general, the present invention provides an adapter for releasably mounting a syringe in a desired position relative to a front-loading powered injector. The syringe includes a body and a plunger slideably positioned within the body. The injector includes a front wall, an opening formed in the front wall, and a drive member reciprocally mounted in the injector. The adapter preferably includes generally a syringe carrier adapted to seat at least a portion of the syringe. The syringe carrier includes at least one rearward facing abutment member to abut at least one forward facing surface on the syringe. The syringe carrier includes an opening therein to allow the drive member of the injector to communicate forward force to the plunger through abutment without connective engagement between the drive member and the plunger. The adapter further includes a releasable mounting mechanism positioned to the rear of the syringe carrier to mount the adapter in a desired position relative to the front wall of the injector.

The syringe may further include a transition region over which the radius or width of the syringe decreases (for example, a generally frusto-conical region) attached to a forward end of the body. The abutment member may abut a forward facing surface created by the transition region. Preferably, the abutment member abuts the transition region only in the vicinity of the transition from the body to the generally frusto-conical region (for example, at to the outer edge of the transition region).

The syringe may further include a syringe flange attached to a rearward end of the body of the syringe. The abutment member may abut a forward facing surface of the syringe flange. Preferably, the abutment member abuts the syringe flange only in the vicinity of the transition from the body to the syringe flange.

In one embodiment, the adapter includes a first section and a second section rotatable relative to each other about a hinge axis generally perpendicular to a longitudinal axis of the adapter. The first section and the second section are preferably rotatable about the hinge axis to an open position to allow loading of the syringe into the adapter from a position to the rear of the hinge axis. The first section and the second section are also preferably rotatable about the hinge axis to a closed position to form the syringe carrier.

In another embodiment, the adapter includes a first section and a second section that are generally the same in construction. The first section and the second section are connectable to form the syringe carrier and the releasable mounting mechanism.

The present invention also provides an adapter for releasably mounting a syringe in a desired position relative to a powered injector. The syringe preferably includes a body and a plunger slideably positioned within the body as discussed above. The injector preferably includes a front wall, an opening formed in the front wall, and a drive member reciprocally mounted in the injector. The adapter includes a first section and a second section that are rotatable relative to each other about a hinge axis generally perpendicular to a longitudinal axis of the adapter to an open position to allow loading of the syringe into the adapter from a position to the rear of the hinge axis. The first section and the second section are also preferably rotatable about the hinge axis to a closed position to form a syringe carrier to seat at least a portion of the syringe.

The present invention also provides an adapter for releasably mounting a syringe in a desired position relative to a powered injector. The adapter preferably includes a first section and a second section that are of generally the same in construction. The first section and the section are connectable to form a syringe carrier to seat at least a portion of the syringe. Preferably, the first section and the section also form a releasable mounting mechanism positioned to the rear of the syringe carrier to mount the adapter in a desired position relative to the front wall of the injector.

In another aspect, the present invention provides an adapter for releasably attaching a syringe to a front-loading powered injector including a releasable mounting mechanism positioned at a rear of the adapter to mount the adapter in a desired position relative to the front wall of the injector. The adapter also includes a syringe carrier section adapted to seat at least a portion of the syringe. The syringe carrier section is preferably open along the length of the top thereof to allow placement of the syringe therein from the top. A portion of the syringe carrier section abuts the transition region of the syringe in a manner that the force exerted by the syringe on the adapter is generally symmetrical about an axis of the adapter during an injection, thereby reducing any bending moment about the mounting mechanism. The syringe carrier section also includes an opening in a rear section thereof to allow the drive member of the injector to communicate forward force to the syringe plunger. The portion of the syringe carrier section abutting the transition region of the syringe can, for example, include a first abutment surface positioned on a first lateral side of the syringe carrier section and a second abutment surface positioned on a second lateral side of the carrier section.

In another aspect, the present invention provides an adapter for releasably attaching a syringe to a front-loading powered injector including an intermediate section through which a push rod can pass to communicate force from the injector drive member to the plunger. The intermediate section has a releasable mounting mechanism positioned at a rear thereof to mount the adapter in a desired position relative to the front wall of the injector. The adapter also includes a syringe carrier section connected to the intermediate section. The syringe carrier section is adapted to seat at least a portion of the syringe and includes an opening in a rear section thereof to allow the drive member of the injector to communicate forward force to the plunger via the push rod.

The syringe carrier section is preferably open on a top thereof. A forward portion of the syringe carrier section abuts the transition region of the syringe during injection. The syringe carrier section is movable relative to the intermediate section to move the forward portion out of contact with the transition region of the syringe to enable removal of the syringe without retraction of the drive member. In one aspect, for example, the carrier section is connected to the intermediate section in a hinging manner.

In another aspect, an adapter system of the present invention includes an intermediate section having a releasable mounting mechanism positioned at a rear thereof as described above. The adapter system also includes a syringe carrier section connected to the intermediate section and adapted to seat at least a portion of the syringe. The syringe carrier section includes an opening in a rear section thereof to allow the drive member of the injector to communicate forward force to the plunger from the drive member and is preferably open on a top thereof. A forward portion of the syringe carrier section abuts the transition region of the syringe during an injection procedure. The adapter system further includes a push rod used to communicate force from the injector drive member to the plunger. The pushrod has a forward section that is movable relative to a rearward section of the pushrod to allow movement of the transition region of the syringe out of contact with the forward portion of the syringe carrier section to enable removal of the syringe from the adapter without retraction of the drive member. The forward section of the push rod can, for example, be rotatable, hingeable or removable relative to the rearward section of the push rod.

Another adapter system of the present invention includes a releasable mounting mechanism positioned at a rear of the adapter to mount the adapter in a desired position relative to the front wall of the injector as described above and a pushrod to communicate force from the drive member to the plunger. The adapter system also includes a syringe carrier section adapted to seat at least a portion of the syringe. The syringe carrier section includes an opening in a rear section thereof to allow passage of the pushrod therethrough to contact to the plunger. The adapter system further includes a contact member preferably positioned in the syringe carrier section to contact the pushrod and prevent a fluid from the syringe from passing rearward of the sealing member. The contact member can, for example, include a wiper seal.

In another aspect, the present invention provides an adapter including a releasable mounting mechanism and a syringe carrier section adapted to seat at least a portion of the syringe. The syringe carrier section is preferably open on a top thereof to allow placement of the syringe therein or removal of the syringe therefrom from the top. The syringe carrier section includes at least one flexing retainer therein to place pressure on at least one side of the syringe to retain the syringe within the syringe carrier section, The syringe carrier section further includes an opening in a rear section thereof to allow the drive member of the injector to communicate forward force to the plunger.

In still a further aspect, the present invention provides an adapter for releasably attaching a syringe to a front-loading powered injector including a releasable mounting mechanism as described above and a syringe carrier section adapted to seat at least a portion of the syringe. A forward abutment portion of the syringe carrier section abuts the transition region of the syringe. The syringe carrier section includes a biasing member to contact a rear surface of the syringe. The biasing member forces or biases the transition region of the syringe against the forward abutment portion for syringes of various lengths. The biasing member can, for example, be biased forward by a spring. The biasing member can also, for example, be biased forward by flexible member on a rear side thereof.

BRIEF DESCRIPTION OF THE DRAWINGS

Other aspects of the invention and their advantages will be discerned from the following detailed description when read in connection with the accompanying drawings, in which:

FIG. 41 illustrates a perspective view of an adapter including another embodiment of a syringe retaining member.

DETAILED DESCRIPTION OF THE INVENTION

Figure 1A:
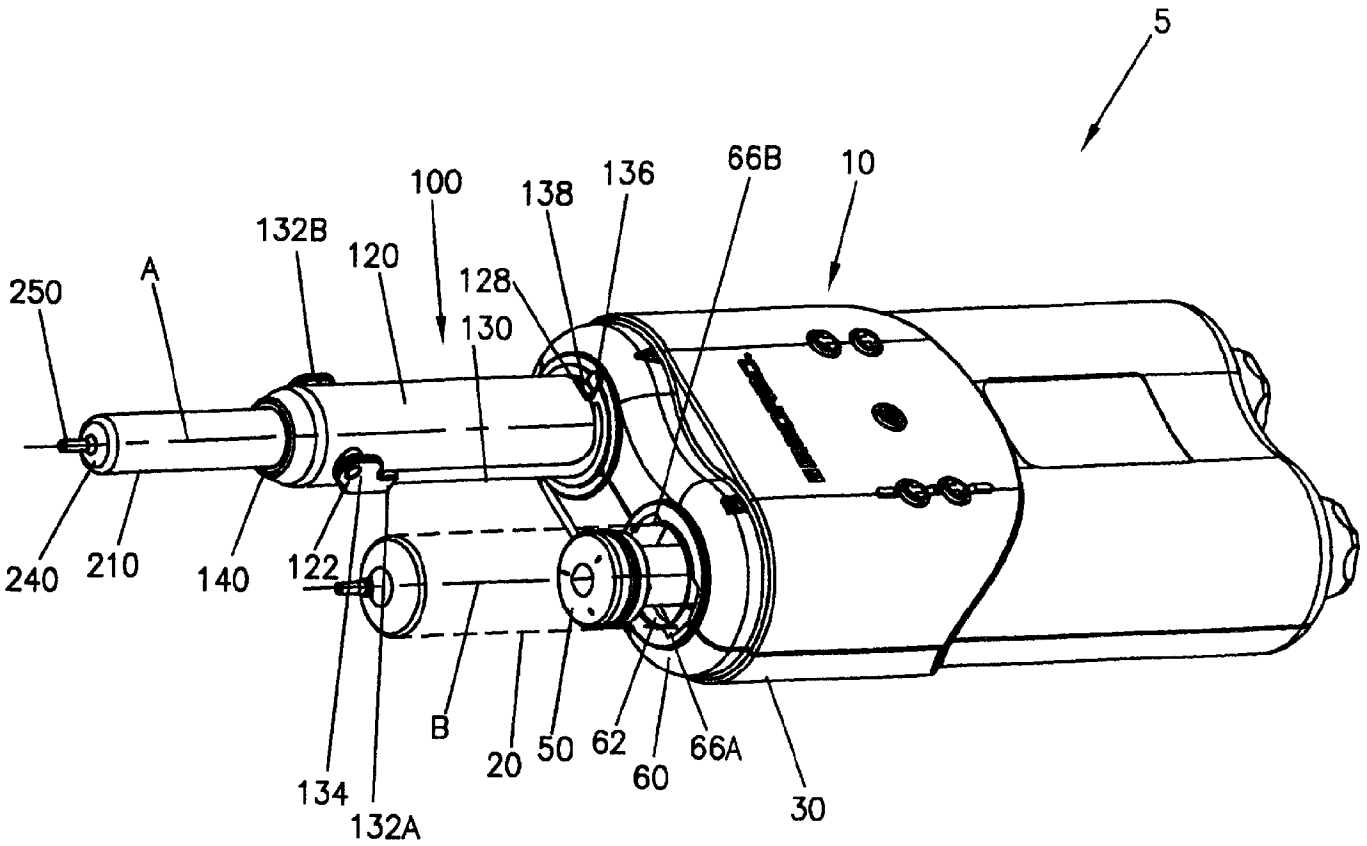
FIG. 1A illustrates an embodiment of an injector system of the present invention for use in connection with an MRI procedure.
Figure 1B:
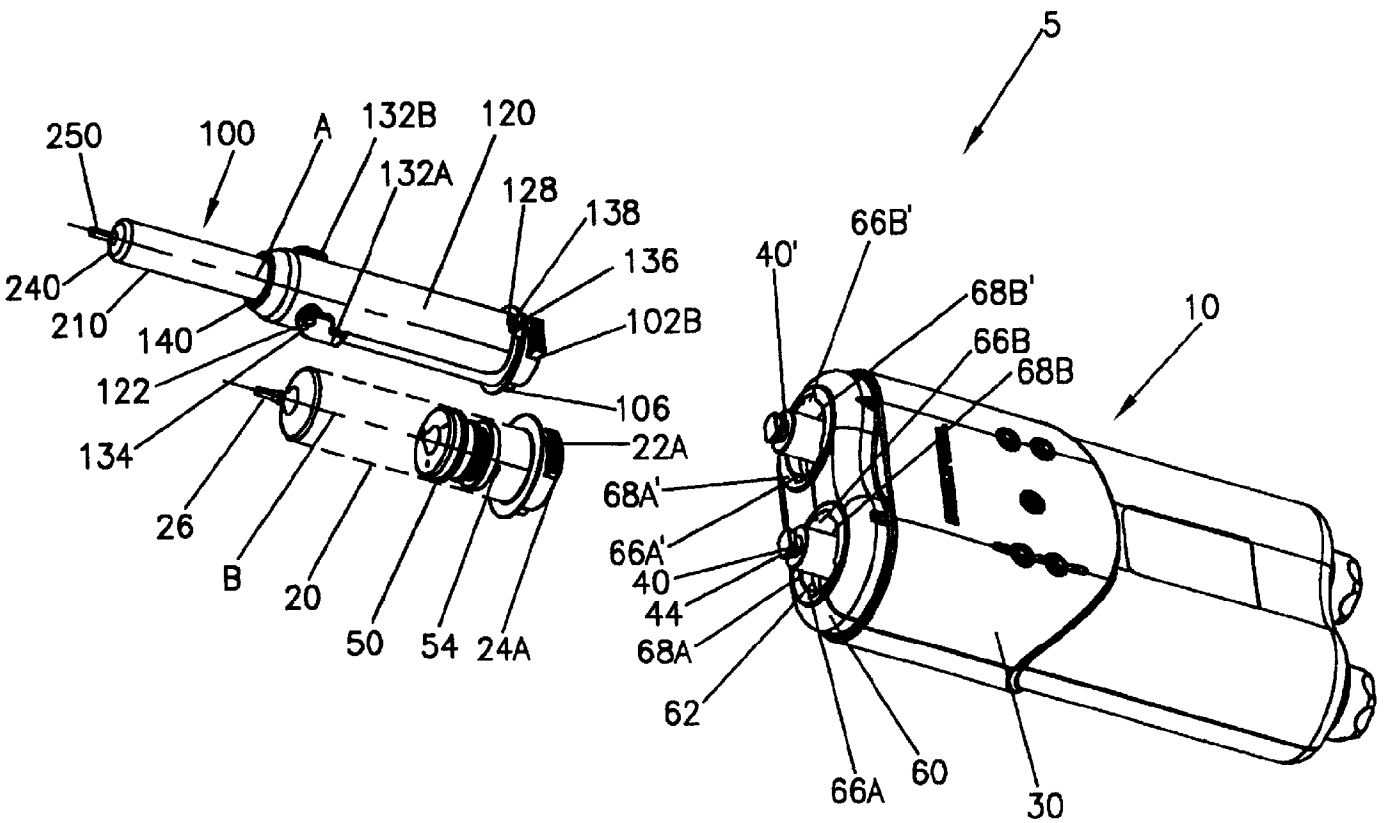
FIG. 1B illustrates the injector system of FIG. 1A in which the saline syringe and the adapter have been disassembled from the injector.

An embodiment of a front-loading injector system 5 of the present invention is illustrated in FIGS. 1A and 1B. Injector system 5 is particularly adapted for use in MRI procedures and includes a powered injector 10, a syringe 20 for injection of saline solution and an adapter 100. An example of an injector 10 suitable for use in the present invention is the SPECTRIS® injector available from Medrad, Inc. of Indianola, Penn. However, the present invention may be used in connection with other fluid delivery systems, including injectors and infusion pumps for computed tomography, ultrasound and angiographic procedures. As best illustrated in FIG. 1B, injector housing 30 of injector 10 preferably includes a first drive member or piston 40 therein which cooperates with a syringe plunger 50 in saline syringe 20 to inject a saline solution from the interior of syringe 20 into a patient.

As shown in FIGS. 1B, injector 10 also includes a second drive member or piston 40' that cooperates with an adapter 100 and a syringe plunger extension rod 220 of a syringe 200 (see, for example, FIG. 2A) containing a fluid such as a contrast medium to inject the fluid from the interior of syringe 200 into a patient.

As used herein to describe injection system 5 and other embodiments of the present invention, the terms "axial" or "axially" refer generally to, for example, an axis A around which adapter 100 is preferably formed (although not necessarily symmetrically therearound) or an axis B around which saline syringe 20 is formed (although not necessarily symmetrically therearound). The terms "proximal" or "rearward" refer generally to an axial or a longitudinal direction toward the end of injector housing 30 opposite the end to which syringe 20 and adapter 100 are mounted. The terms "distal" or "forward" refer generally to an axial or a longitudinal direction toward a syringe tip of syringe 20 or syringe 200. The term "radial" refers generally to a direction normal to an axis such as axis A or axis B.

Saline syringe 20 and adapter 100 are preferably removably connected to injector 10 as described in U.S. Pat. No. 5,383,858. In that regard, front-loading injector 10 preferably includes a front wall 60 having a first opening 62 formed therein. Piston 40 is reciprocally mounted within injector 10 and is extendible through opening 62. Piston 40 preferably includes a piston flange or head 44. Receiving slots 66a and 66b, are preferably positioned opposite one another around opening 62. Receiving flanges 68a and 68b are preferably positioned opposite one another and between receiving slots 66a and 66b and extend inwardly into opening 62.

The rearward end of saline syringe 20 preferably includes a readily releasable mounting mechanism such as a pair of mounting flanges 22a and 22b for mounting saline syringe 20 in a desired position relative to the front wall 60 of injector 10. Flange 22b is not shown but is generally identical to flange 22a and positioned opposite flange 22a. Mounting flanges 22a and 22b may include indicating means, such as detent(s), bar code(s), protrusion(s) or notch(es) 24a, which provide information to the injector 10, for example, about the type of saline syringe 20 being used. Correspondingly, injector 10 preferably includes any suitable means (not shown) for reading information from notch(es) 24a.

To attach syringe 20 to injector 10, the rearward end of syringe 20 is inserted into injector opening 62 such that mounting flanges 22a and 22b are inserted into receiving slots 66a and 66b, respectively. If, at this time, plunger 40 is not positioned at the rearward end of syringe 20 such that a piston flange 44 can engage capture members 54 (as described in U.S. Pat. No. 5,383,858), piston 40 may be advanced forward by the operation of injector 10 until piston flange 44 is in position to be received by capture members 54.

Once mounting flanges 22a and 22b are inserted into receiving slots 66a and 66b, respectively, and piston 40 is in position to be received by capture members 54, the operator preferably rotates syringe 20 approximately 90 degrees such that mounting flanges 22a and 22b move behind and are engaged by receiving flanges 68a and 68b, respectively, and piston flange 44 rotates into position to be retained by, for example, L-shaped capture members 54. Injector 10 may include a stop mechanism (not shown), for example, extending from at least one of the retaining slots 68a and 68b, to prevent rotation of syringe 20 more than 90 degrees. Tactile, visual or audible feedback can be provided to the operator via, for example, cooperating members on syringe 20 and injector 10 to inform the operator that secure connection has been achieved. After securely attaching syringe 20 to injector 10, advancing piston 40 in a forward direction will apply a motive force to plunger 50 to advance plunger 50 forward within syringe 20, thereby forcing saline solution in syringe 20 out of syringe neck 26 into the fluid path to the patient. Retracting piston 40 in a rearward direction will cause plunger 50 to move rearward in syringe 20, thereby drawing fluid into syringe 20.

Adapter 100 is preferably attached to injector 10 in a similar manner as described above for attachment of syringe 20 to injector 10. In that regard, a rearward portion or section of adapter 100 preferably includes a readily releasable mounting mechanism such as a pair of mounting flanges 102a and 102b (see FIG. 2A) for mounting adapter 100 in a desired position relative to the front wall 60 of injector 10. Mounting flanges 102a and 102b may include indicating means, such as detents or notches 104a and 104b, which provide information to injector 10 about the type of adapter and/or syringe being used. Correspondingly, injector 10 preferably includes any suitable means (not shown) for reading information from notches 104a and 104b.

To attach adapter 100 to injector 10, the rearward end of adapter 100 is inserted into injector opening 62' such that mounting flanges 102a and 102b are inserted into receiving slots 66a' and 66b', respectively. Once mounting flanges 102a and 102b are inserted into receiving slots 66a' and 66b', respectively, the operator preferably rotates adapter 100 or adapter 100/syringe 200 combination approximately 90 degrees such that mounting flanges 102a and 102b move behind and are engaged by receiving flanges 68a' and 68b', respectively. As described above, a stop mechanism (not shown) may, for example, extend from at least one of the retaining slots 68a' and 68b', to prevent rotation of adapter 100 more than 90 degrees. Once again, tactile, visual or audible feedback can be provided to the operator via, for example, cooperating members on adapter 100 and injector 10 to inform the operator that secure connection has been achieved. A drip flange 106 can, for example, be formed on a rearward portion of adapter 100 to, among other things, assist in forming a secure connection. Drip flange 106 may, for example, include a raised member or detent 108 (see, for example, FIG. 2A) that mates with a recess (not shown) in the face of opening 62' to provide audible and/or tactile feedback to the operator upon proper alignment/connection of adapter 100 to injector 10.

After securely attaching adapter 100 to injector 10, advancing piston 40' in a forward direction will apply a motive force to a plunger extension 220 of syringe 200 to a advance syringe plunger 225 (see FIG. 2E) forward within syringe barrel 210, thereby forcing contrast medium in syringe 200 out of syringe neck 250 into the fluid path to the patient.

Adapter 100 is illustrated in further detail in FIGS. 2A through 2E. In the embodiment of adapter 100, a "break" action is used to load syringe 200 into a carrier 110 of adapter 100. In that regard, carrier 110 includes a first portion or section 120 and a second portion or section 130. First portion 120 is hingingly attached to second portion 130 via support arms 132a and 132b, each of which includes a passage 134 therein. First portion 120 includes generally cylindrical tabs 122 on each side thereof that snap into passages 134 to hingingly or rotatably attach first portion 120 to second portion 130 about an axis C (see, for example, FIG. 2D) preferably oriented generally perpendicular to longitudinal axis A of adapter 100.

Figure 2A:
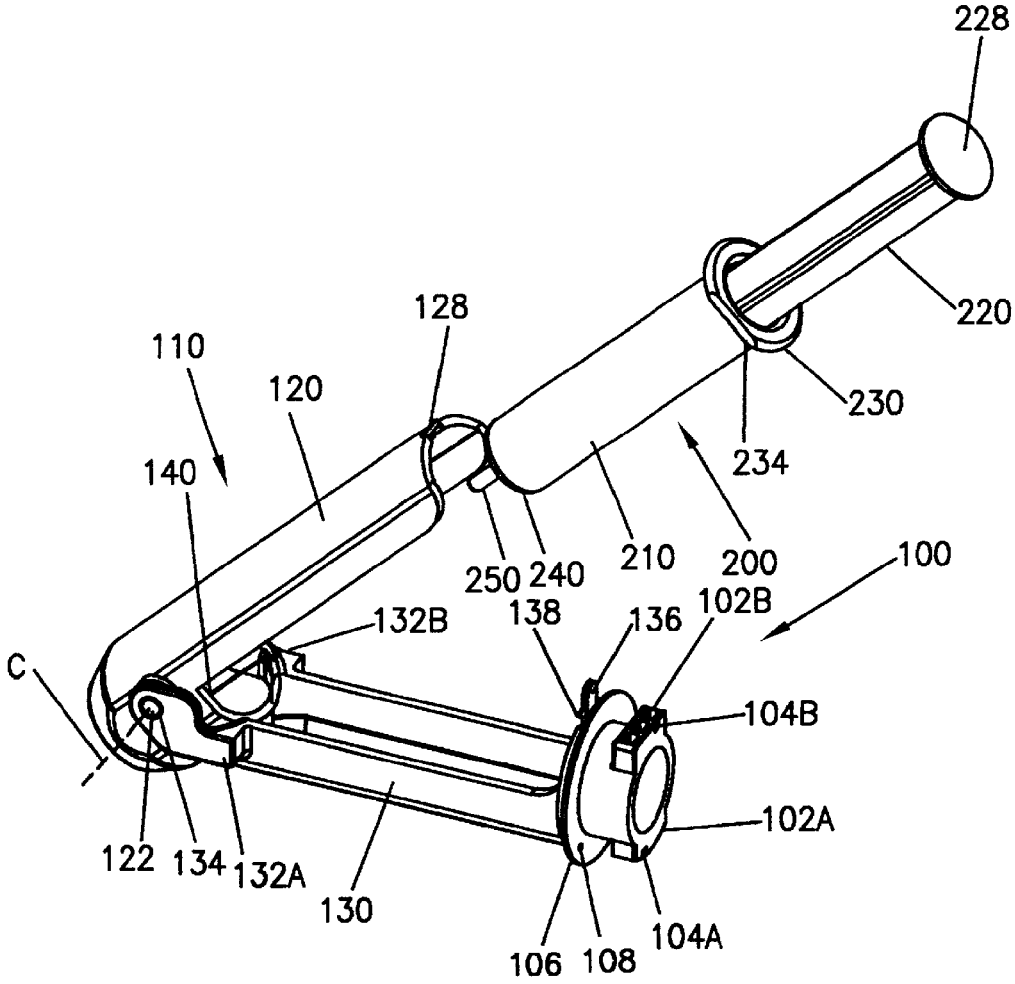
FIG. 2A illustrates a perspective view of an embodiment of an adapter of the present invention in an open state for loading of a syringe therein.

FIG. 2A illustrates adapter 100 in an open state and ready to receive syringe 200 from a position to the rear of the hinging mechanism. In this embodiment, syringe 200 comprises generally cylindrical body or barrel 210 in which a fluid such as contrast medium, saline or therapeutic agent is contained. Preferably, the fluid medium is "prefilled" into syringe 200 before loading of syringe 200 in adapter 100. Syringe 200 can, for example, be prefilled by the manufacturer or manually filled remote from the injector. Syringe 200 further includes plunger 225 slideably disposed within barrel 210 that is similar in operation to plunger 50 of saline syringe 20. Plunger 225 of syringe 200 is operatively connected to plunger extension rod 220 by, for example, a threaded connection. Syringe 200 further includes a flange 230 at a rearward end of barrel 210. At a forward end of barrel 210, syringe 200 includes, for example, a generally frusto-conical transition or cone region 240 that connects barrel 210 to a tapered neck 250 from which contrast medium is injected. Tapered neck 250 can include, for example, a luer connection at the end thereof for connection to a fluid path (for example, flexible tubing) as known in the art.

In many cases, syringes 200 for use, for example, in an MRI procedure are prefilled with contrast medium by the manufacturer. Many such syringes 200 are designed for manual injection into a patient wherein an operator manually advances plunger rod 220 (and thereby plunger 225 within syringe 200) forward by applying pressure to a rearward end 228 of plunger extension rod 220. Syringe barrel 210 and flange 230 may, for example, be fabricated from glass or plastic. Plunger extension rod 220 is typically fabricated from a plastic material.

Figure 2B:
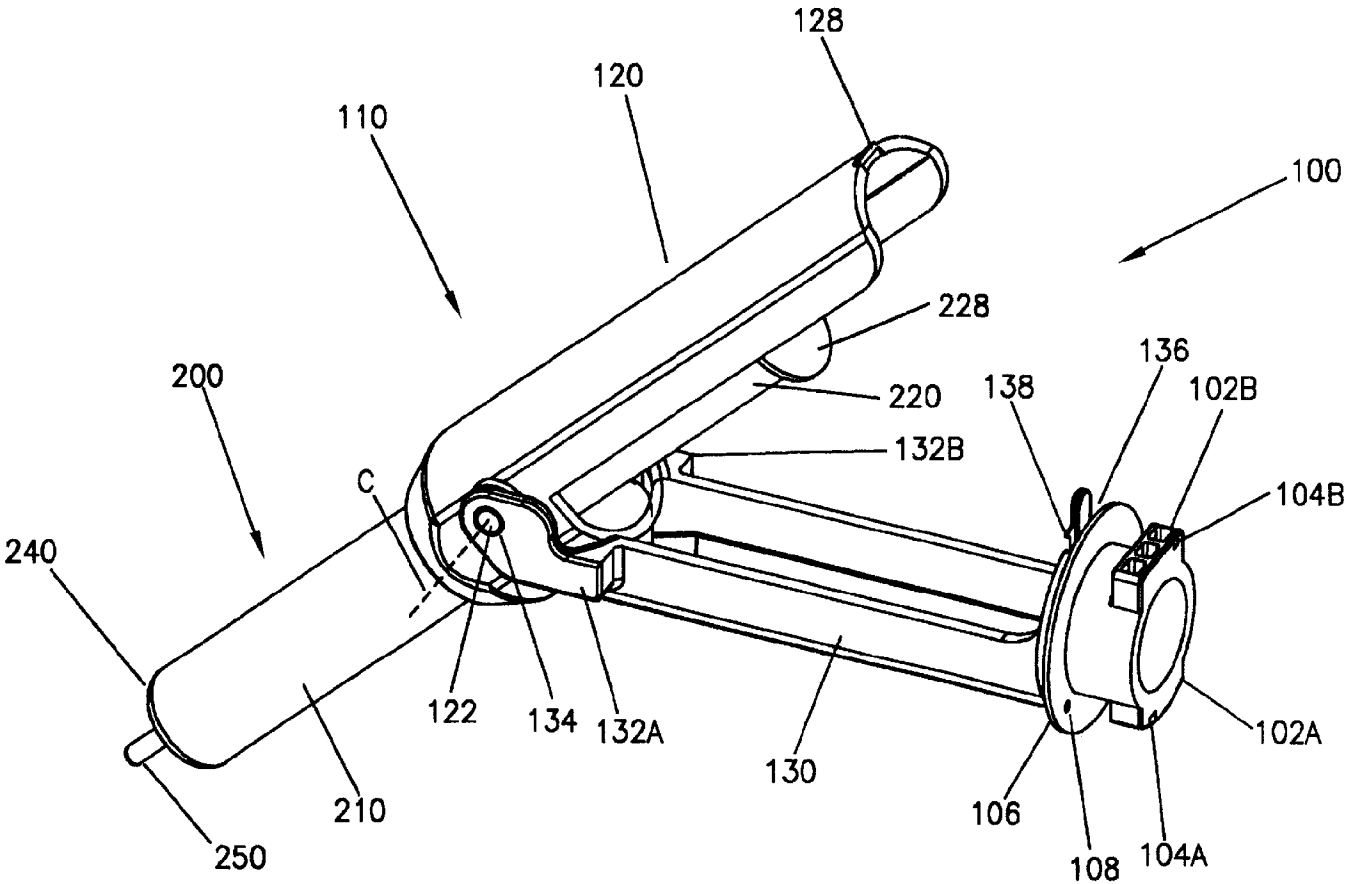
FIG. 2B illustrates a perspective view of the adapter of FIG. 2A in an open state with a syringe loaded therein.

As illustrated in FIGS. 2A and 2B, syringe 200 is loaded into carrier 110 by positioning syringe 200 in general alignment with a generally cylindrical passage 140 formed in a forward end of first portion 120 of adapter 100. Syringe 200 is slid forward within passage 140 until syringe flange 230 abuts a shoulder 150 (see FIG. 2E) that extends radially inwardly within first portion 120. Shoulder 150 cooperates with syringe flange 230 to hold syringe 200 within adapter 100 and to provide resistance to the forward force applied to plunger extension rod 220 by piston 40' during an injection procedure.

Figure 2C:
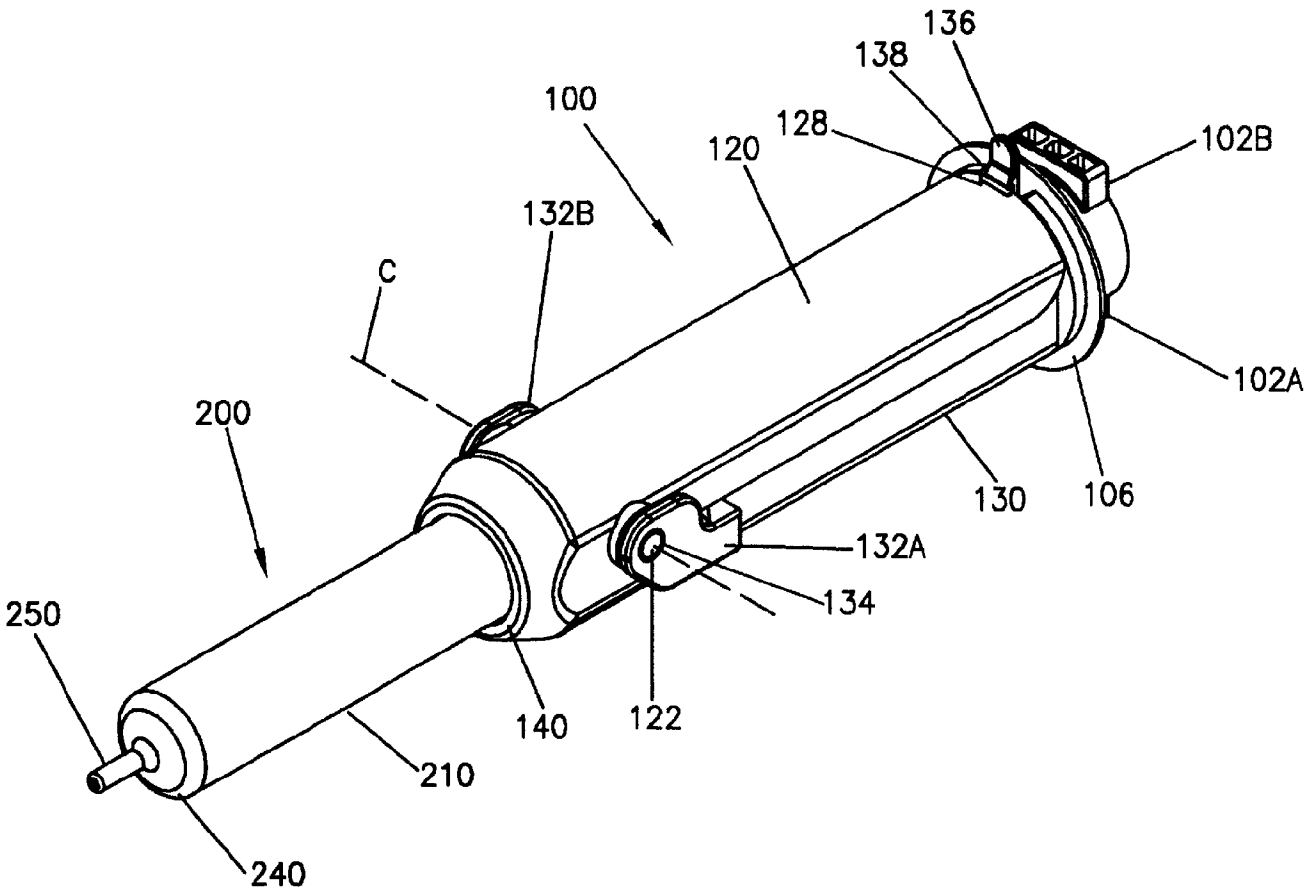
FIG. 2C illustrates a perspective view of the adapter of FIG. 2A in a closed state with a syringe loaded therein.
Figure 2D:
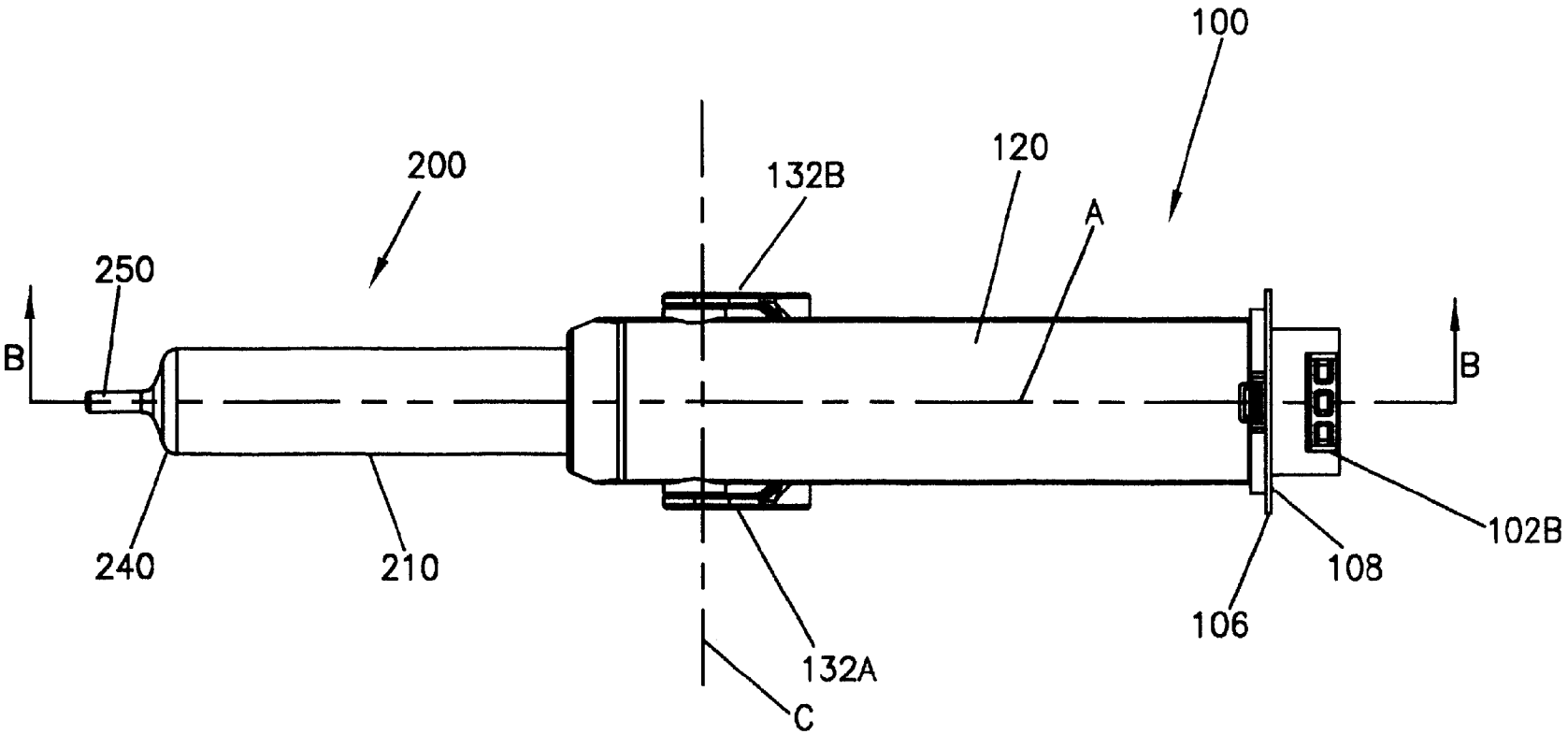
FIG. 2D illustrates a plan view of the adapter of FIG. 2A in a closed state with a syringe loaded therein.
Figure 2E:
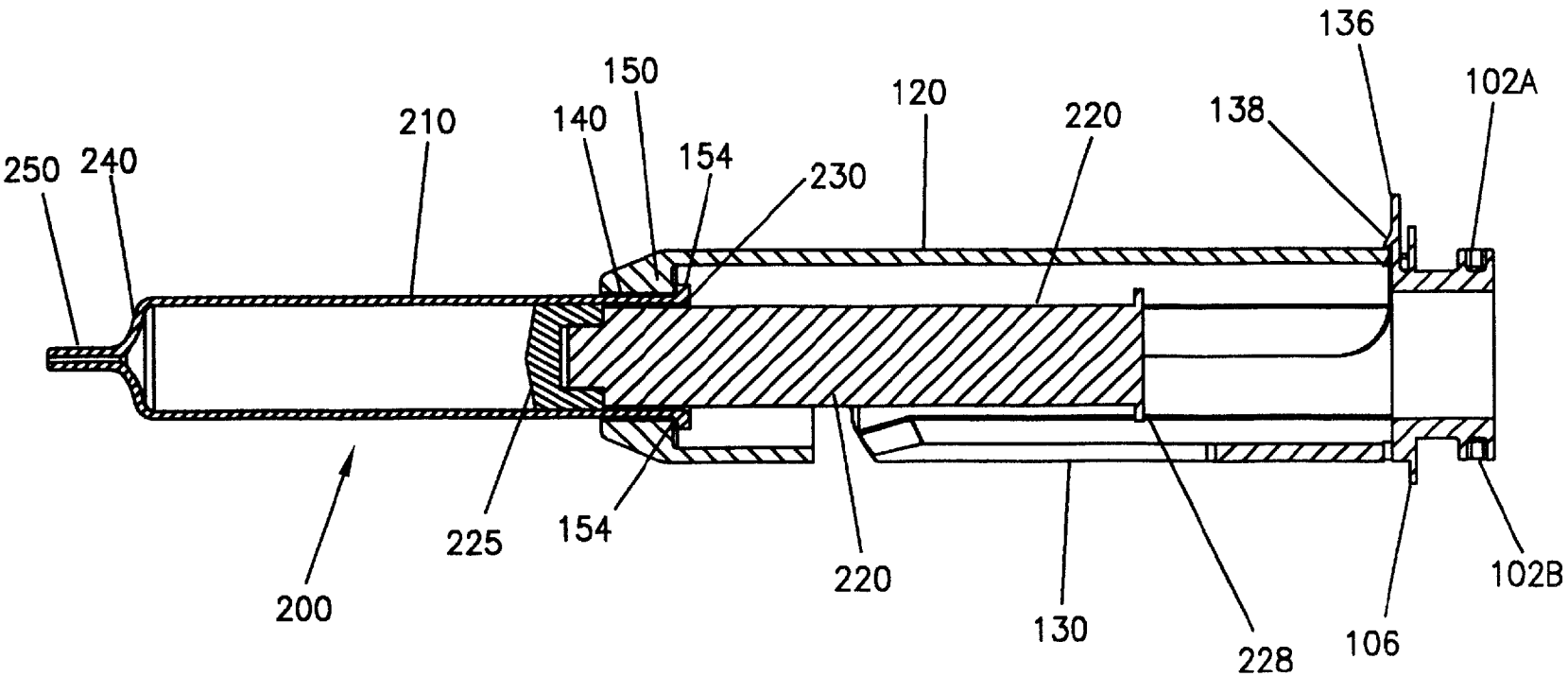
FIG. 2E illustrates a side, cross-sectional view of the adapter of FIG. 2A in a closed state with a syringe loaded therein.

As best illustrated in FIG. 2E, shoulder 150 preferably includes a rearward extending ridge portion 154 on the inner radius thereof so that ridge portion 154 contacts flange 230 only near or in the vicinity of the transition of syringe flange 230 into syringe barrel 210. Contact of ridge portion 154 with syringe flange 230 near barrel 210 assists in minimizing the forces placed upon cantilevered flange 230. For example, in the case of glass syringes 200, flange 230 may fail (break) if contact with shoulder 150 is made at or near the outer end of syringe flange 230, whereas the shorter lever arm resulting from contact with syringe flange 230 at or near the inner radius thereof will reduce the force on syringe flange 230 and prevent failure. Ridge portion 154 can be made of a resilient or compliant material such as an elastomeric material that can be different from the material of the remainder of adapter 100 to further reduce the likelihood of failure.

In the case of a prefilled syringe 200, there is no need for the operator to retract the plunger of syringe 200 to load syringe 200 with contrast medium. Therefore, there is usually no need for a follower mechanism in the adapter of the present invention to attach to plunger extension rod 220 to enable retraction of plunger 225 as described in connection with the adapter of U.S. Pat. No. 5,520,653. Piston 40' can simply be advanced to abut rearward surface 228 of plunger extension rod 220. Any further forward motion of piston 40' will result in advancement of the plunger of syringe 200 and pressurization of the contrast medium with syringe 200. Elimination of a carrier mechanism for the plunger extension simplifies and reduces the cost of manufacture of the adapters of the present invention as compared, for example, to the adapter of U.S. Pat. No. 5,520,653. Nevertheless, the adapters of the present invention may readily be configured with follower mechanisms that connect to plunger extension rods 220 to allow plunger retraction.

FIGS. 2C through 2E illustrate syringe 200 within adapter 100 with first portion 120 and second portion 130 in a closed position. Adapter 100 preferably includes a mechanism to assist in maintaining first portion 120 and second portion 130 in a closed position during operation of injector 100. Second portion 130 may, for example, include a latch tab 136 having an abutment shoulder 138 that cooperates with a recess 128 in a rearward end of first portion 120 to create a snap latching mechanism. Many other closing mechanisms can be used to maintain first portion 120 and second portion 130 in a closed position, as clear to one skilled in the art.

Closed carrier 110 created by first portion 120 and second portion 130 also functions to limit the motion of plunger extension rod 220 out of alignment with axis A. This prevents plunger extension rod 220 from, for example, slipping out of contact with piston 40', prevents deforming of plunger extension rod 220 and prevents eccentric loading of plunger extension rod 220. Deflection, eccentric loading or deforming of plunger extension rod 220 may, for example, cause leaking of fluid to the rear of plunger 225 or breaking of syringe 200. Radially inward projecting guide(s) can be formed in one or both of first portion 120 and second portion 130 to maintain even tighter tolerances. A section of either or both of first portion 120 and second portion 130 can be "cut away" to form a window for viewing of syringe extension rod 220. Likewise, a portion or the entirety of either or both first portion 120 and second portion 130 can be transparent.

Preferably, one or both of first portion 120 and second portion 130 includes an abutment member to prevent rotation of syringe 200 within carrier 110. It is, for example, desirable to prevent rotation of syringe 200 after connection thereof to fluid path tubing. Prevention of syringe rotation can also maintain syringe 200 in proper orientation for viewing, for example, volume gradations on syringe 200. One or more sides of first portion 120 can, for example, have a flattened profile to conform to flattened section(s) 234 of syringe flange 230 to prevent rotation of syringe 200.

As illustrated in FIGS. 2B through 2E, a substantial portion of syringe 200 extends forward through passage 140 so that syringe barrel 210 is plainly visible to the operator. Such visibility, for example, facilitates reading of wording printed on the syringe as well as visual determination of the volume of contrast remaining in syringe 200. Visibility of syringe 220 also allows the operator to more readily determine whether air is present in syringe 200 before commencing an injection procedure. Moreover, operators typically like to see plunger 225 in motion to provide reassurance that the injection is proceeding. Extension of a portion of syringe 200 beyond carrier 110 also facilitates grasping of syringe 200 by the operator to, for example, connect or disconnect a fluid path to syringe neck 250.

As illustrated, for example, in FIGS. 2A through 2C, axis C of rotation of the hinge mechanism (that is, the axis passing through the radial center of generally cylindrical tabs 122 in the embodiment of FIG. 2A) is preferably positioned such that the force experienced by carrier 110 during forward advancement of piston 40' tends to force or maintain carrier 100 in a closed position. The axis of cylindrical tabs 122 is preferably, for example, positioned above the center line or longitudinal axis of carrier 110 such that a forward force exerted on shoulder 150 tends to produce a torque that maintains first portion 120 in a latched, closed position relative to second portion 130.

Once an injection procedure is completed, the operator can grasp the adapter or adapter/syringe combination and rotate it 90 degrees back to the preinstallation orientation, thereby, disengaging mounting flanges 102a and 102b from behind receiving flanges 68a and 68b, respectively. The adapter/syringe combination is then removable from the injector 10.

Retaining syringe 200 within carrier 110 by abutment with shoulder 150, allows accommodation of many different designs of syringe 200 by carrier 110. Adapter 100 is thus usable with a wide variety of currently available syringes 200.

FIGS. 3A through 3E illustrate another embodiment of an adapter 300 for use with a syringe 200. The rearward portion of adapter 300 is essentially identical to that of adapter 100 and is removably attached to injector 10 as described above. Unlike adapter 100, which holds syringe 200 within adapter 100 and provides resistance to the forward force applied to plunger extension rod 220 by abutment of syringe flange 230, syringe 200 is held within adapter 300 and resistance provided to the forward force applied to plunger extension rod 220 by abutting a forward facing surface of forward transition region 240 of syringe 200 rather than by abutting or retaining syringe flange 230.

Like adapter 200, a hinging or "break" action is used to load syringe 200 into a carrier 310 of adapter 300. In that regard, carrier 310 includes a first portion 320 and a second portion 330. First portion 320 is hingingly or rotatably attached to second portion 330 via support arms 332a and 332b, each of which includes a passage 334 therein. First portion 320 includes generally cylindrical tabs 322 on each side thereof that reside in passages 334 to hingingly attach first portion 320 to second portion 330. First portion 320 rotates about an axis C that runs generally through the radial centers of tabs 322 and is generally perpendicular to the longitudinal axis A of adapter 300.

Figure 3A:
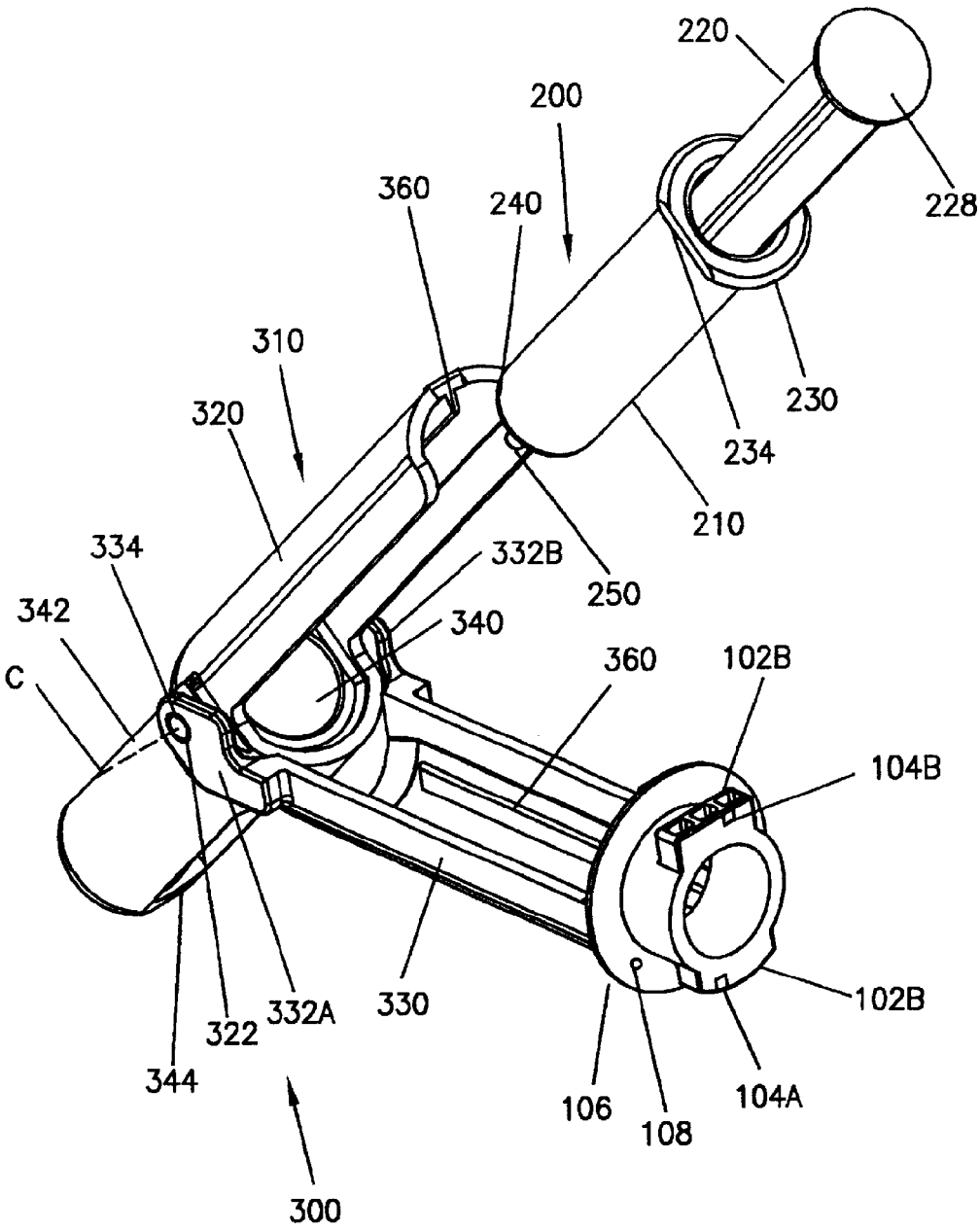
FIG. 3A illustrates a perspective view of another embodiment of an adapter of the present invention in an open state for loading of a syringe therein.
Figure 3B:
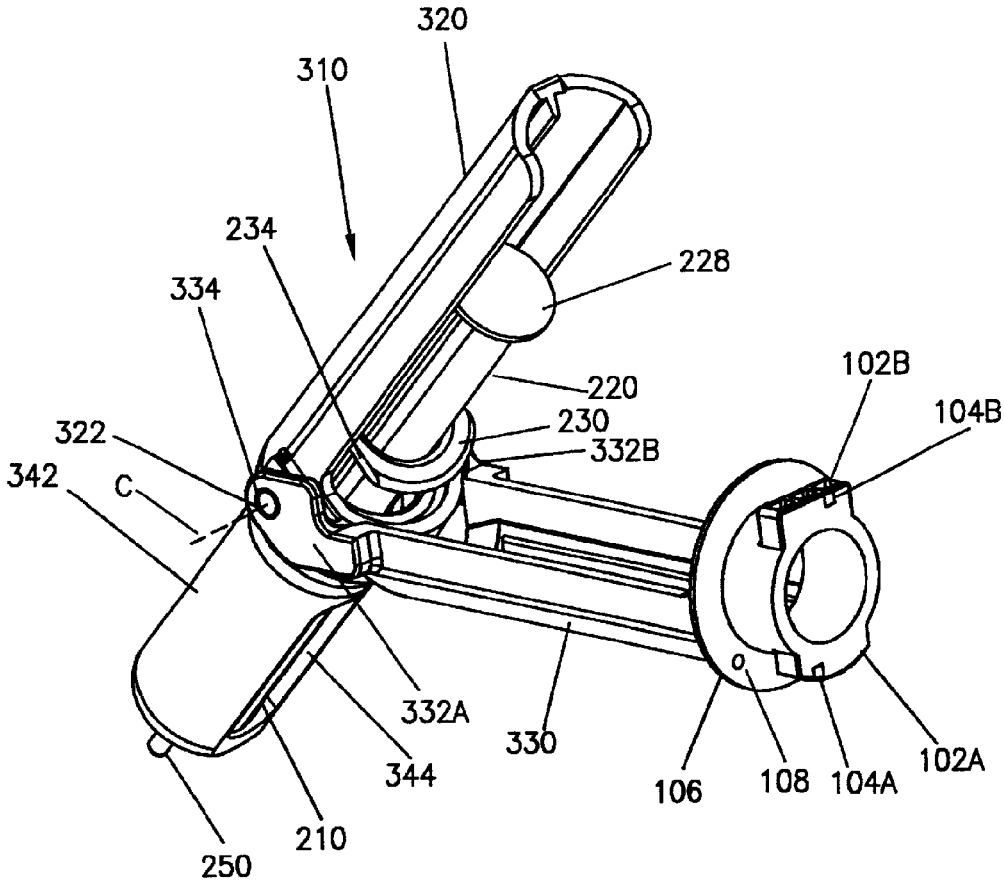
FIG. 3B illustrates a perspective view of the adapter of FIG. 3A in an open state with a syringe loaded therein.
Figure 3C:
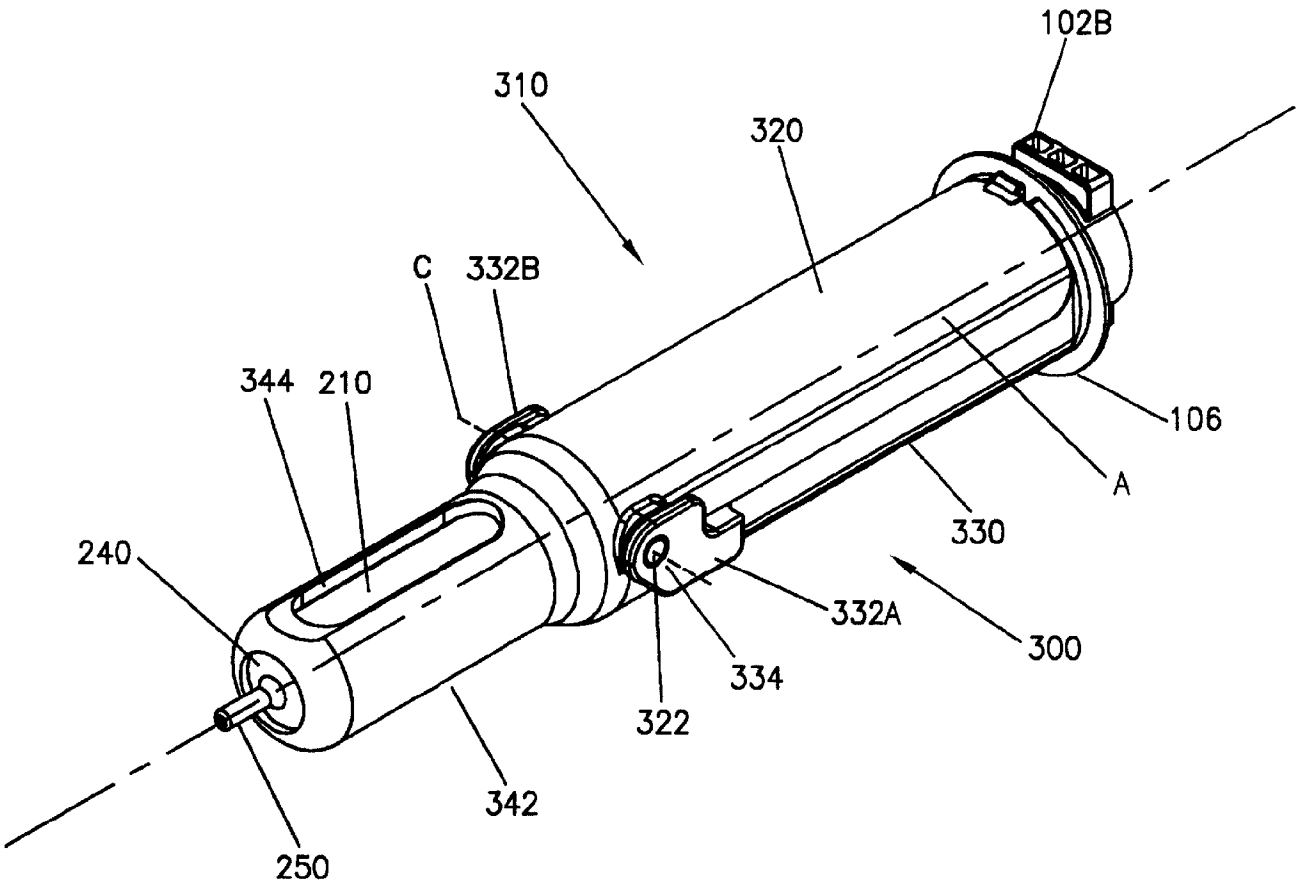
FIG. 3C illustrates a perspective view of the adapter of FIG. 3A in a closed state with a syringe loaded therein.
Figure 3D:
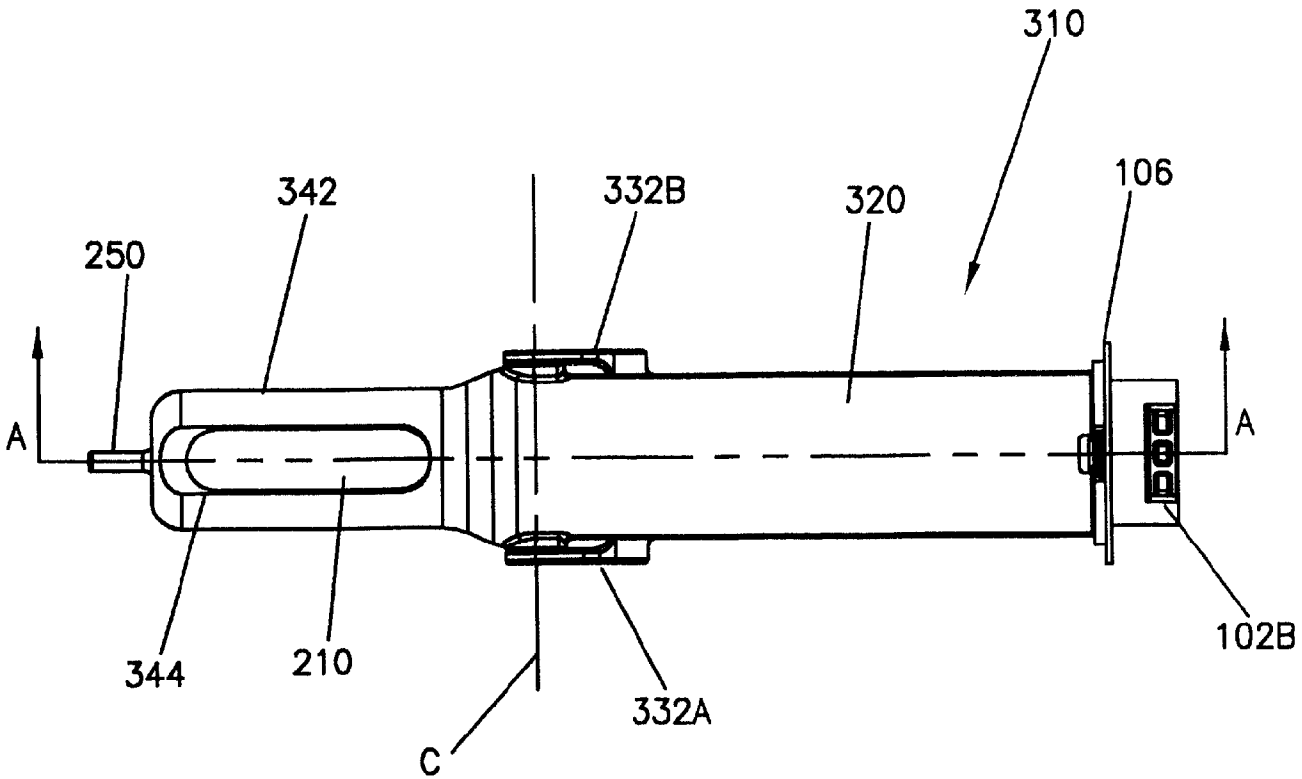
FIG. 3D illustrates a plan view of the adapter of FIG. 3A in a closed state with a syringe loaded therein.
Figure 3E:
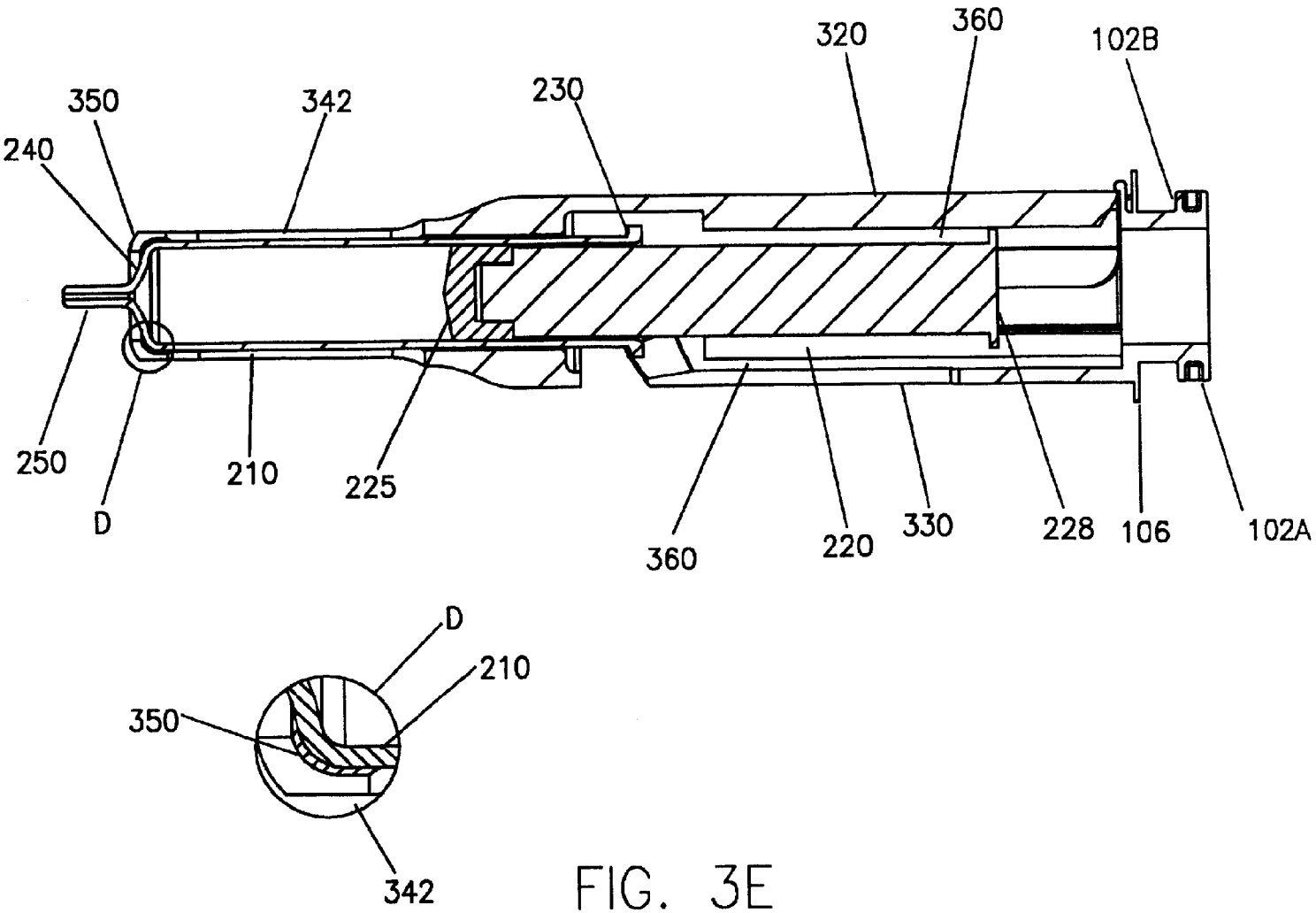
FIG. 3E illustrates a side, cross-sectional view of the adapter of FIG. 3A in a closed state with a syringe loaded therein.

FIG. 3A illustrates adapter 300 in an open state and ready to receive syringe 200. As illustrated in FIGS. 3A and 3B, syringe 200 is loaded into carrier 310 by positioning syringe 200 in general alignment with a generally cylindrical passage 340 formed in first portion 320 of adapter 300. Syringe 200 is slid forward within passage 340 until a forward facing surface of syringe 200 abuts a retention shoulder 350 (see FIG. 3E) that extends radially inward at a forward end of a forward portion 342 of first portion 310. Shoulder 350 cooperates with forward syringe transition region or cone 240 to hold syringe 200 within adapter 300 and to provide resistance to the forward force applied to plunger extension rod 220 by piston 40' during an injection procedure. As illustrated in detail D of FIG. 3E, shoulder 350 preferably contacts syringe 200 only near to or in the vicinity of the transition from the sidewall of barrel 110 to transition region 240 to take advantage of increased structural strength in this region. The contact area of shoulder 350 can be made of a resilient or compliant material (for example, an elastomeric material) to absorb energy and reduce the likelihood of breaking syringe 200.

Syringe 200 may be inserted in adapter 300 before connection of adapter 300 to injector 10. Alternatively, syringe 200 may be loaded into adapter 300 while adapter 300 is mounted on injector 10. Indeed, adapter 300 may remain mounted on injector 10 through many different injection procedures with different syringes.

Forward portion 342 preferably includes one or more open areas or windows 344 so that syringe barrel 210 is plainly visible to the operator. All or a portion of forward portion 342 can also be transparent to further facilitate viewing of syringe barrel 210. Open areas 344 also facilitate grasping of syringe 200 by the operator to, for example, connect or disconnect a fluid path to syringe neck 250. As described in connection with adapter 100, one or both of first portion 320 and second portion 330 may include an abutment member to prevent rotation of syringe 200 within carrier 310. For example, the side(s) of first portion 320 can have a flattened profile to conform to flattened section(s) 234 of syringe flange 230 to prevent rotation of syringe 200. The cooperation of such a flattened profile of carrier 310 and section 234 can, for example, be used to ensure a desired orientation of syringe barrel 210 with open areas 344. For example, two open areas 344 can be provided generally opposing each other (that is, positioned approximately 180° apart on forward portion 342). The cooperation of a flattened profile of carrier 310 and flattened syringe flange section 234 in this embodiment preferably allows mounting of syringe 200 in carrier 310 in only two axially rotated orientations, 180° apart.

One or a plurality of inward projecting guide 360 can be formed in one or both of first portion 120 and second portion 130 to maintain tight tolerances to prevent deflection of plunger extension rod 330 as discussed above. A plurality (for example, three) guides 360 can be used about first portion 120 and/or second portion 130 to limit or prevent deflection in any direction.

Open areas (not shown) can also be provided on carrier 310 in the area where syringe flange 230 resides to accommodate large (in a radial direction) or irregularly shaped syringe flanges 230. Such open areas preferably extend longitudinally to accommodate syringes of different length from a forward end thereof to the syringe flange thereof. In general, the adapters of the present invention preferably provide adequate capacity to accommodate syringes of widely varying length, diameter etc.

An important function of an injector is to monitor and report the actual volume of fluid available for delivery within a syringe. This function, for example, enables rapid decision on whether enough fluid is present to proceed with an imaging procedure or whether additional volume should be loaded. Monitoring the cumulative volume of fluid delivered to a patient is also desirable for certain applications where a recommended per-patient dosage volume should not be exceeded. Fluid volumes delivered by injectors are typically displayed in 1.0 ml increments and are tracked by the injector with finer resolution than is displayed. Injectors also preferably detect and differentiate among different types and sizes of syringes so that accurate display and delivery of fluid volume is provided.

To achieve such fluid volume management specifications, an adapter or syringe must be installed on an injector, be oriented in a known manner and provide the control system with identification information. Identification can be provided by coded features on the adapter or syringe that are detected by sensors on the injector so that each adapter and/or syringe is known by its code and fluid volume parameters specific to that syringe are implemented. When syringes 200 that are intended for non-powered, hand injection are installed on power injector 10, adequate identification is still preferably provided. This result can be achieved by first placing syringe 200 in adapter 100 or 300 which facilitates mounting on injector 10 and possesses its own unique code as encoded by, for example, the positions of notches 104a and 104b. In this manner, many different types and sizes of syringes 200 and/or adapters can be accommodated.

Syringes 200 are frequently of similar geometry such that more than one type of syringe 200 can be carried by the same adapter, giving rise to the potential of incorrect identification and possible fluid delivery error by injector 10. However, it is desirable to minimize the number of adapters required to accommodate all the hand syringes intended for a specific injector leading to a need to install more than one volume of syringe per adapter, provided individual functionality can be achieved. Syringes that share the same functional internal diameter, but have different lengths of travel can be treated as equivalent if both are referenced to the adapter, and consequently to injector 10, by a front-most surface thereof (that is, cone or transition region 240). If syringes 200 sharing the same functional diameter but having different lengths are referenced to the adapter injector 10 by rear flange 230 only, injector 10 will not be able to determine where the front of a syringe 200 is and cannot accurately determine/report the volume of contrast medium available. Mounting hand syringes 200 by rear flange 230 as in the embodiment of adapter 100 thus preferably requires one adapter per syringe diameter and length combination, which results in a larger number of adapters than would be required using a front mounting as in the embodiment of adapter 300. Multiple adapter combinations decrease the ease of use for an operator and expand the logic and sensing capacity required of injector 10. An optimum approach would be to use a single adapter that accommodates all hand syringes targeted for a particular injector. To approach this goal, it is preferable to retain/abut a front end of syringes 200 as described above in connection with adapter 300 so that injector 10 can determine the position of the front end of syringe 200. Loading of a front end of syringe 200 is also preferred to take advantage of an area of increased syringe strength to prevent syringe failure.

Figure 4A:
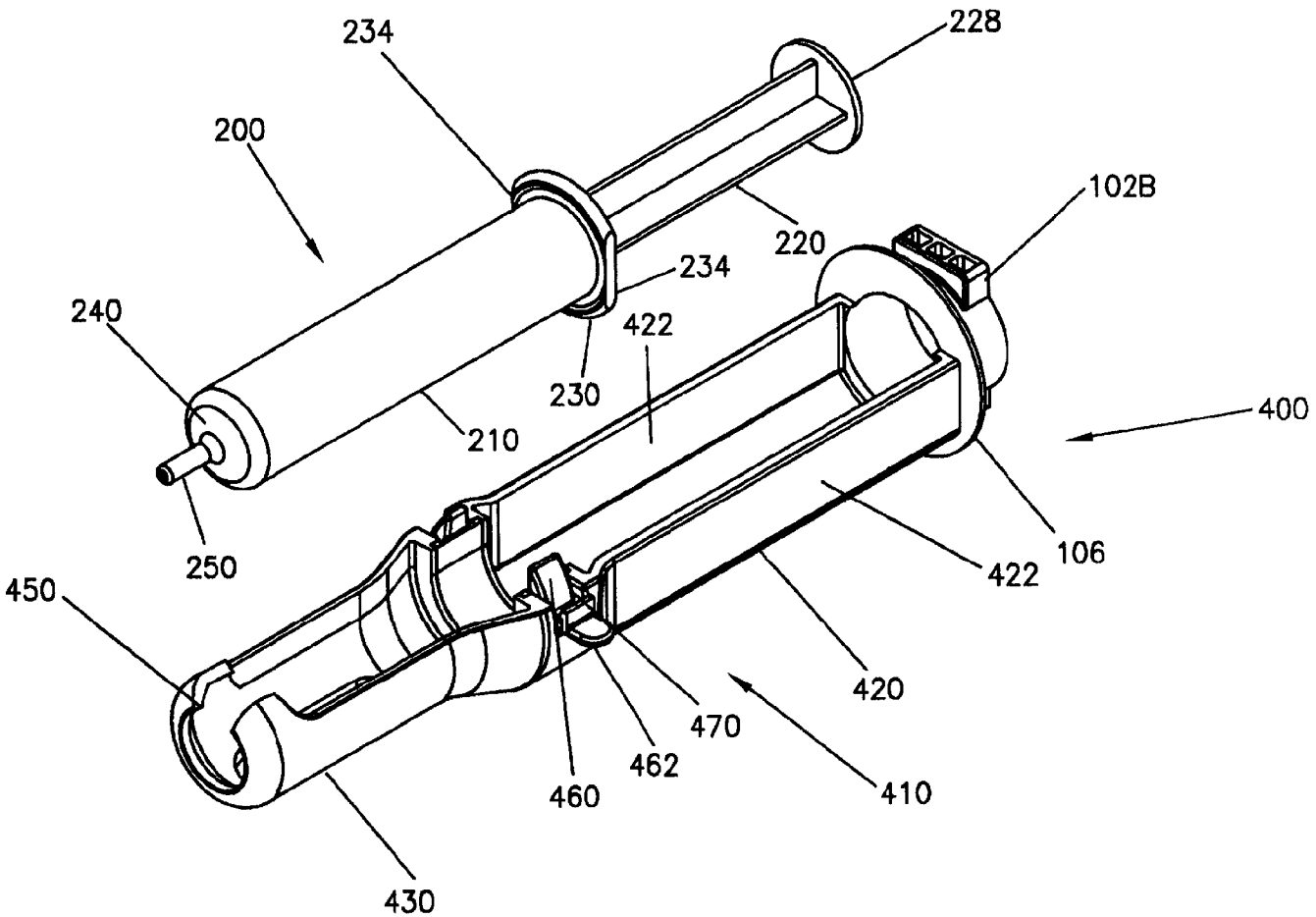
FIG. 4A illustrates a perspective view of another embodiment of an adapter of the present invention with a syringe positioned to be inserted therein.
Figure 4B:
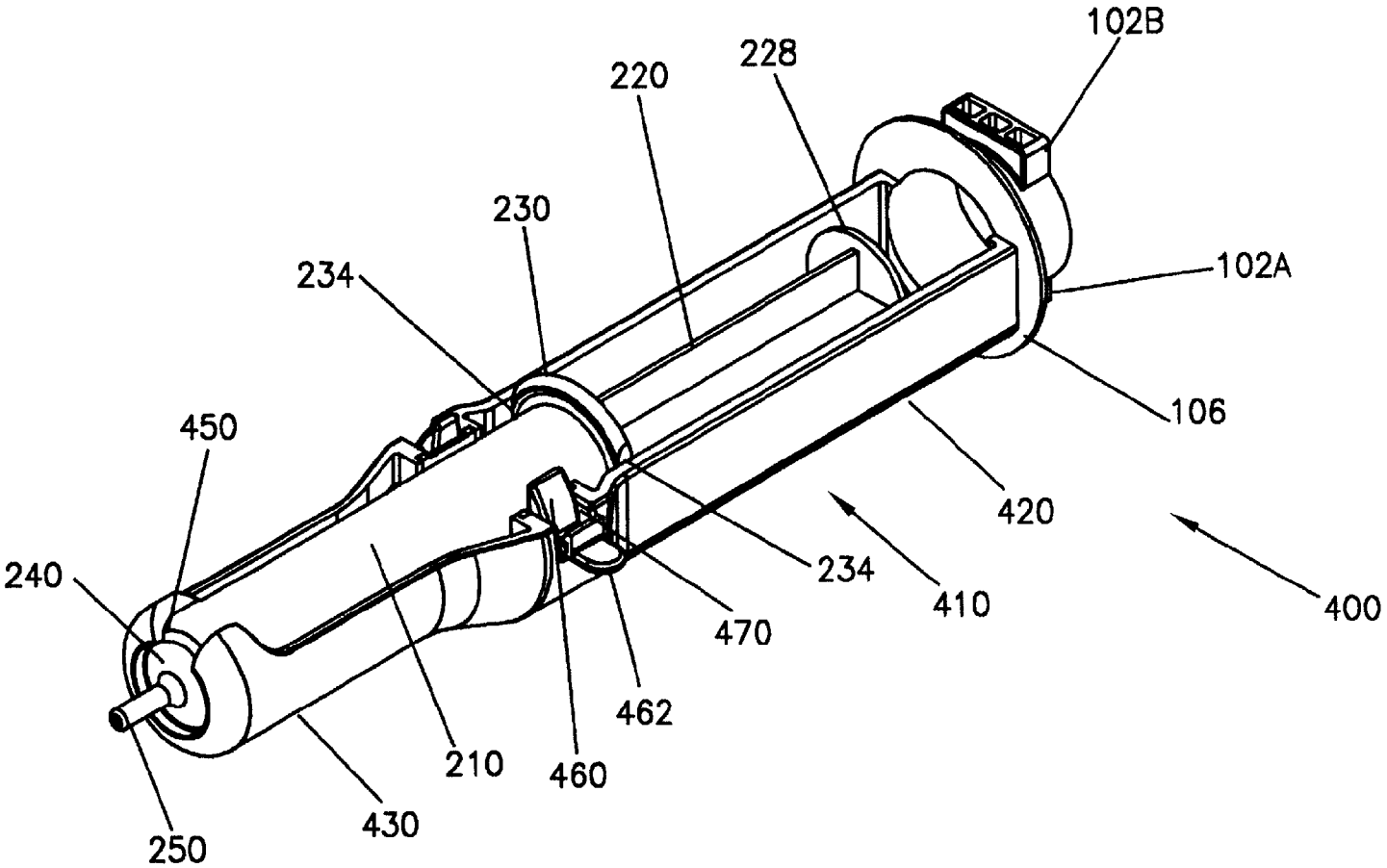
FIG. 4B illustrates a perspective view of the adapter of FIG. 4A with the syringe positioned therein.
Figure 4C:
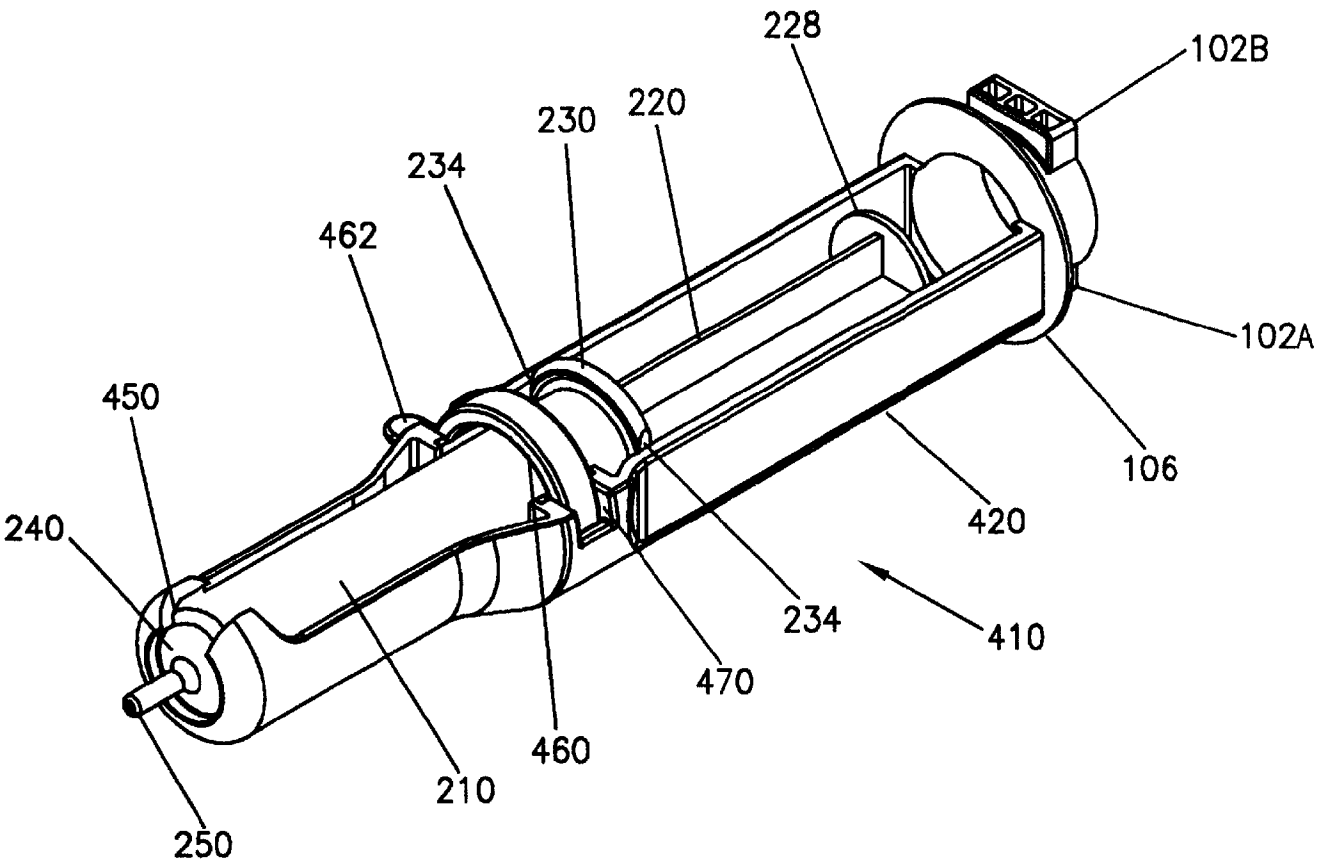
FIG. 4C illustrates a perspective view of the adapter of FIG. 4A wherein a syringe retaining member is in a closed position.

FIGS. 4A through 4C illustrate another embodiment of an adapter 400 for use with syringe 200. The rearward portion of adapter 400 is essentially identical to that of adapters 100 and 300 and is removably attached to injector 10 as described above. Unlike adapters 100 and 300, which incorporate a hinging action to enclose syringe 200, syringe 400 includes an open carrier 410. Like adapter 300, however, syringe 200 is held within adapter 400 and resistance provided to the forward force applied to plunger extension rod 220 by abutting forward transition or cone region 240 of syringe 200.

As illustrated in FIGS. 4A and 4B, syringe 200 is simply loaded into adapter 400 by dropping syringe 200 therein from above. Adapter 400 preferably includes a first, rearward portion 420 that seats/supports syringe flange 230. Preferably, first portion 420 has generally flat side walls 422 that cooperate with generally flat sections 234 on syringe flange 230 to restrict or substantially prevent rotation of syringe 200 within adapter 400. Side walls 422 of first portion 420 preferably extend upward past the generally common axis of syringe 200 and adapter 400 to assist in supporting syringe 200.

Adapter 400 further includes a second, forward portion 430 that seats/supports syringe barrel 210. Second portion 430 preferably includes a radially inward extending abutment shoulder 450 that abuts cone or transition region 340 of syringe 200 to retain syringe 200 within adapter 400 and provide resistance to the forward force applied to plunger extension rod 220 by piston 40'. Although second portion 430, including abutment shoulder 450, are open on the top thereof, the generally cylindrical wall of second portion 430 and abutment shoulder 450 can extend upward past the generally common axis of syringe 200 and adapter 400 to support resistance of the forward force applied to plunger extension rod 220 and to prevent deflection of syringe 200 out of alignment with the shared axis of syringe 200 and adapter 400.

Through abutment shoulder 450, adapter 400 provides the benefits of forward abutment of syringe 200 discussed above. Moreover, because adapter 400 is open along its entire axial length, insertion and removal of syringe 200 is facilitated. For example, syringe 200 can even be easily removed from adapter 400 while still connected to a fluid path (not shown in FIGS. 4A through 4C). In some cases, however, it may be desirable to form abutment shoulder 450 to contact a forward facing surface of transition region 240 around its entire circumference to provide additional stability. In that case, the forwardmost end of carrier 410 would be closed and any fluid path would preferably be disconnected before removing syringe 200 from adapter carrier 410.

Figure 4D:
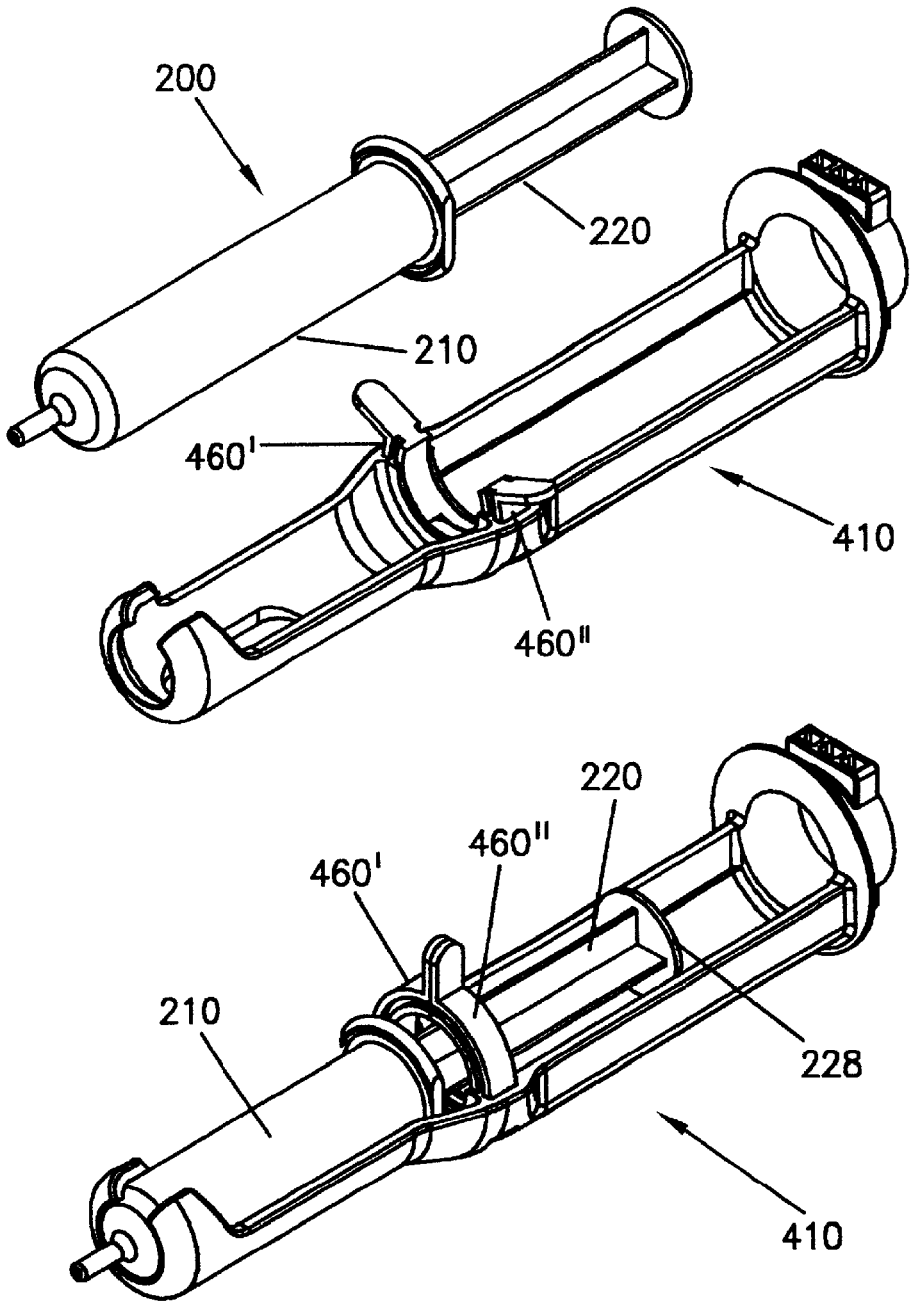
FIG. 4D illustrates a perspective view of an adapter including another embodiment of a syringe retaining member.

Adapter 400 preferably further includes at least one retaining member 460 to assist in retaining and/or stabilizing syringe 200 in proper alignment therein. Retaining member 460 is slideably retained in a generally cylindrically shaped passage 470 in carrier 410. Retaining member 460 is illustrated in an open or disengaged position in FIGS. 4A and 4B. To close or engage retaining member 450 to retain syringe 200, the operator can supply force to collar tab 462 to rotate retaining member 450 within passage 470 to a closed position as illustrated in FIG. 4C. In another embodiment illustrated in FIG. 4D, rotatable retaining member 460 can be split into two portions 460' and 460" that rotate to meet in the middle.

Figure 4E:
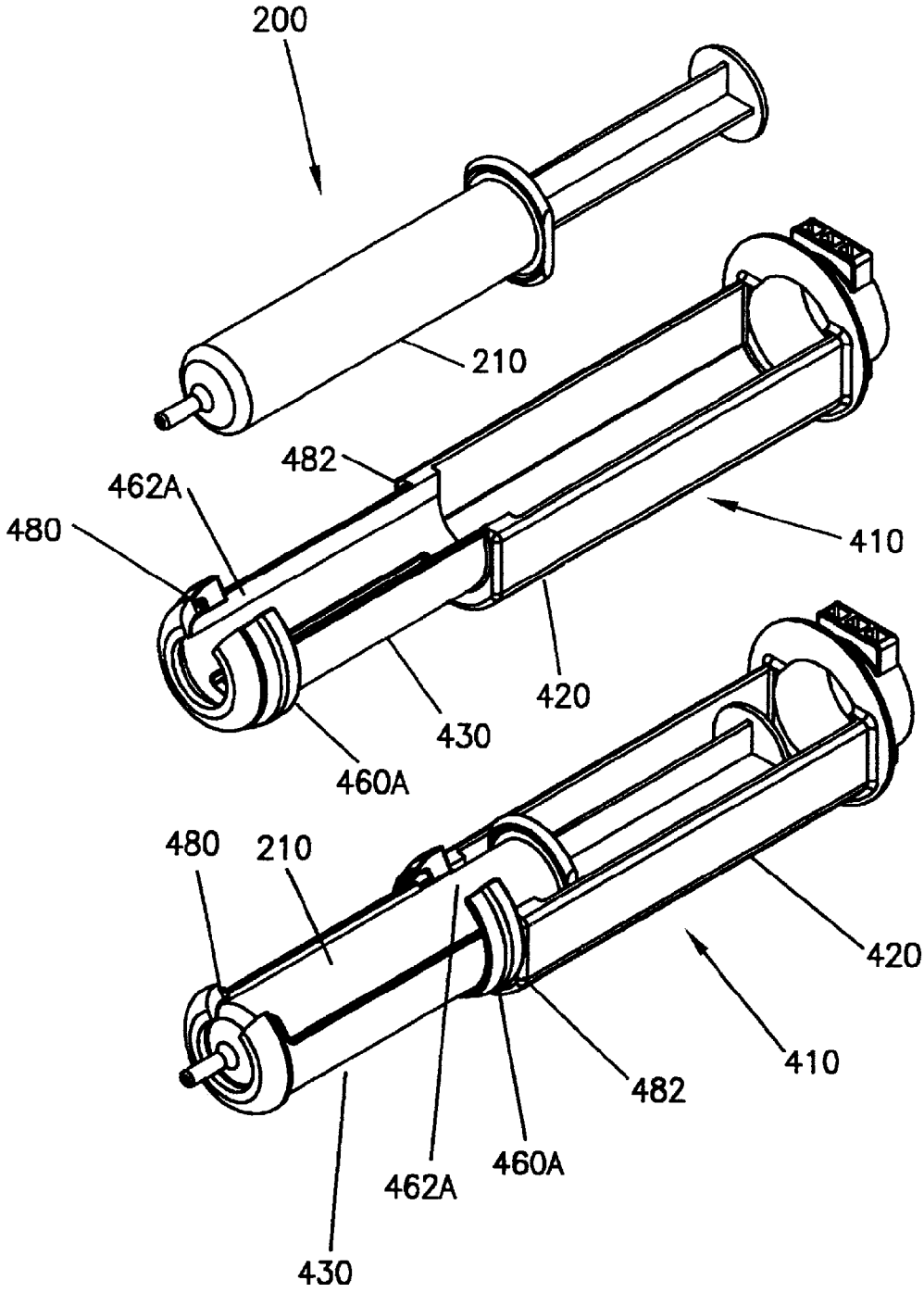
FIG. 4E illustrates a perspective view of an adapter including another embodiment of a syringe retaining member.

Other retaining/stabilizing members or mechanisms for retaining/stabilizing syringe 200 are illustrated in FIGS. 4E through 4I. In FIG. 4E a sliding retaining member 460a is positioned on/around second, forward portion 430 of carrier 410. Retaining member 460a is preferably positioned at a forwardmost position on second portion 430 when syringe is loaded into carrier 410 to facilitate loading. Retaining member 460a is retained on second portion 430 by abutment with a forward shoulder 480 and rearward shoulder 482. After seating of syringe 200, retaining member 450a can preferably be slid to any desired position on second portion. Positioning retaining member 460A at a rearwardmost position on second portion 430 may maximize stability. Retaining member 460a preferably conforms closely to the shape of syringe barrel 210 to maximize stability. Retaining member 460a may include an open section 462a on the top thereof to facilitate removal of syringe 200 from carrier 410 without disconnection of an attached fluid path element.

Figure 4F:
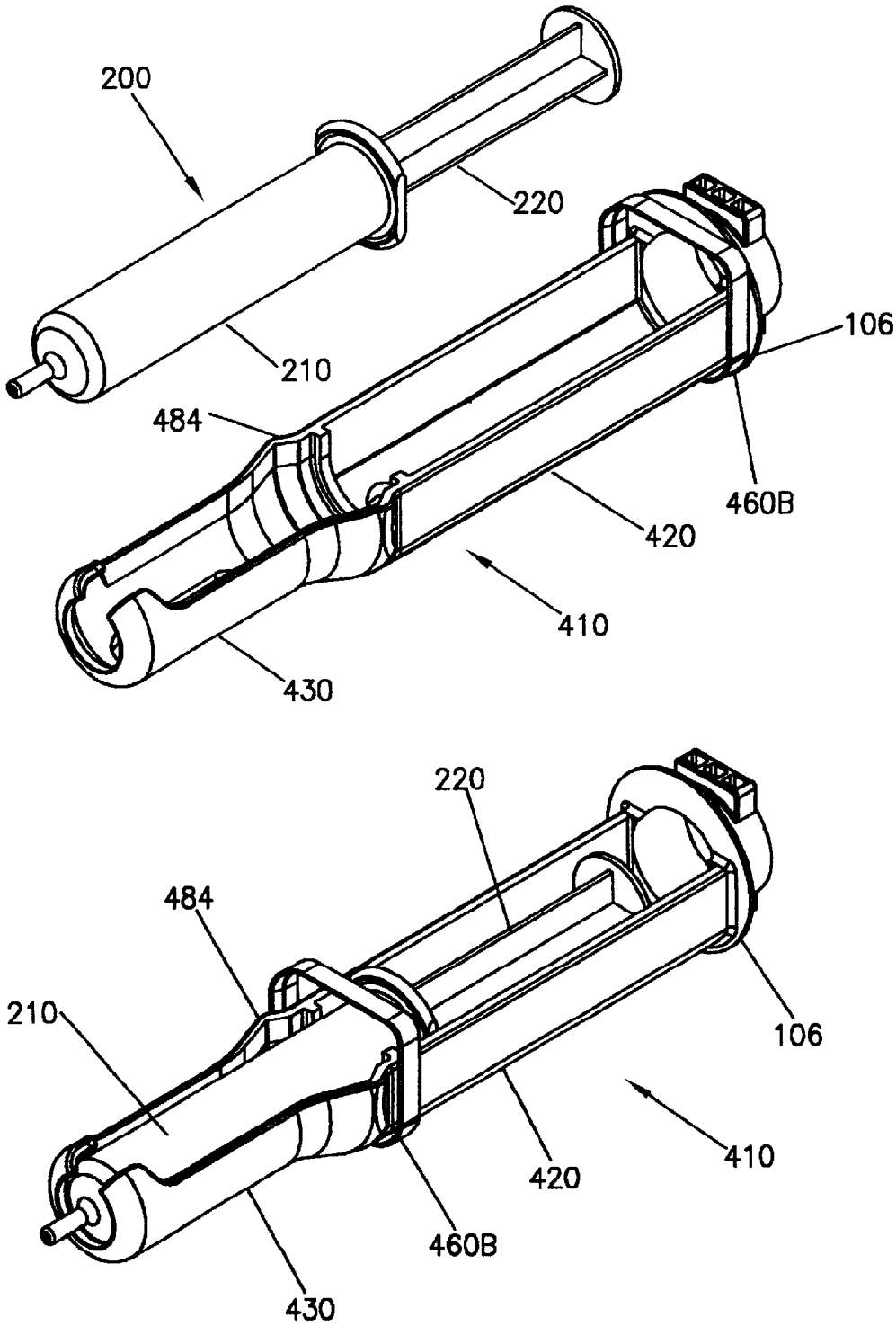
FIG. 4F illustrates a perspective view of an adapter including another embodiment of a syringe retaining member.

FIG. 4F illustrates another embodiment of a slideable retaining member 460b. Retaining member 460b is slideably retained upon first portion 420 of carrier 410 between drip flange 106 and shoulder 484. To facilitate loading of syringe 200, retaining member 450b may be positioned near drip flange 106. After loading of syringe 200, retaining member 460b can be slid to a desired position. An opening (not shown) in retaining member 460b can be formed to facilitate removal of syringe 200 from carrier 410 without disconnection of an attached fluid path element.

Figure 4G:
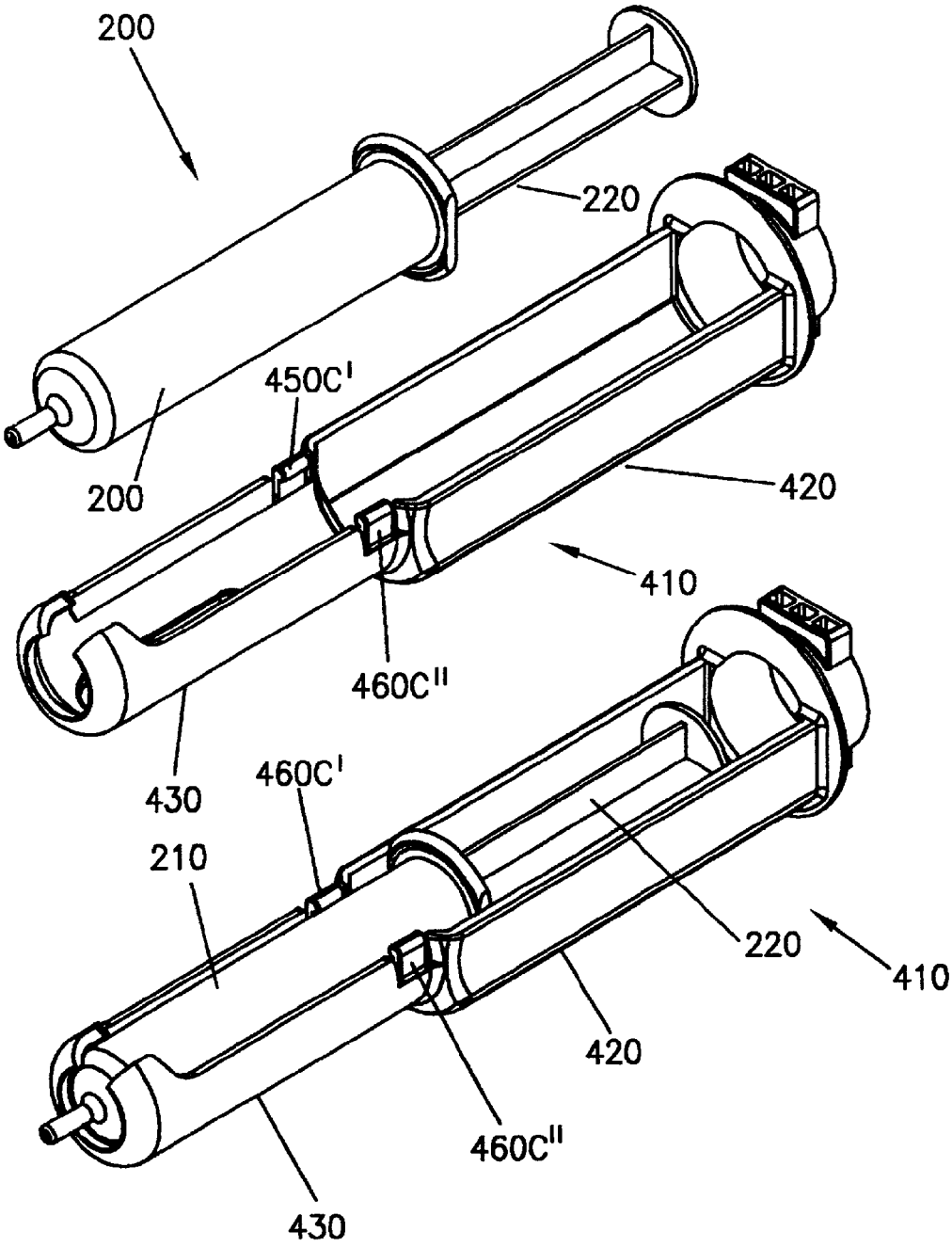
FIG. 4G illustrates a perspective view of an adapter including another embodiment of a syringe retaining member.

In the embodiment of FIG. 4G, a retaining mechanism includes two cantilevered retaining member 460c' and 460c" that snap around syringe barrel 210 upon loading of syringe 200 in carrier 410.

A plurality of retaining/stabilizing members as described above can be provided along the length of carrier 410 to assist in retaining/stabilizing syringe barrel 210 and plunger extension rod 420 in proper position within carrier 410. The opening and closing of such retaining members can be operated individually or collectively, for example, via a common tab.

Figure 4H:
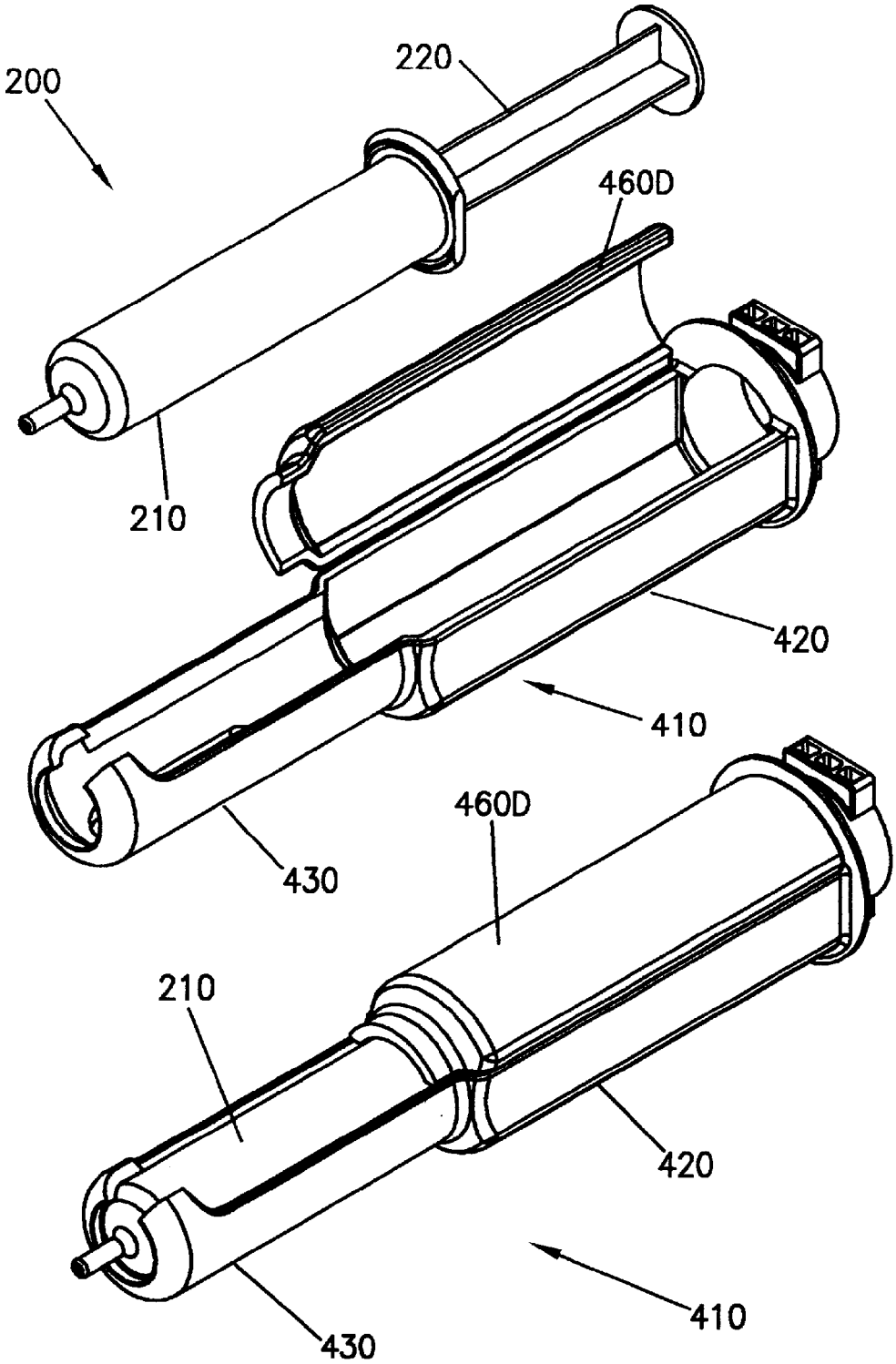
FIG. 4H illustrates a perspective view of an adapter including another embodiment of a syringe retaining member.

Alternatively, a retaining/stabilizing member can be increased in axially length to increase stability. For example, FIG. 4H illustrates a retaining member 460d hingingly attached to first portion 420 that extends along the entire length of first portion 420 and partially along the length of second portion 430 when closed. A similar retaining member can alternatively or additionally be hingingly attached to second portion 430. As an alternative to a hinging motion, such retaining member can rotate in a passage or slot formed in carrier 410.

Figure 4I:
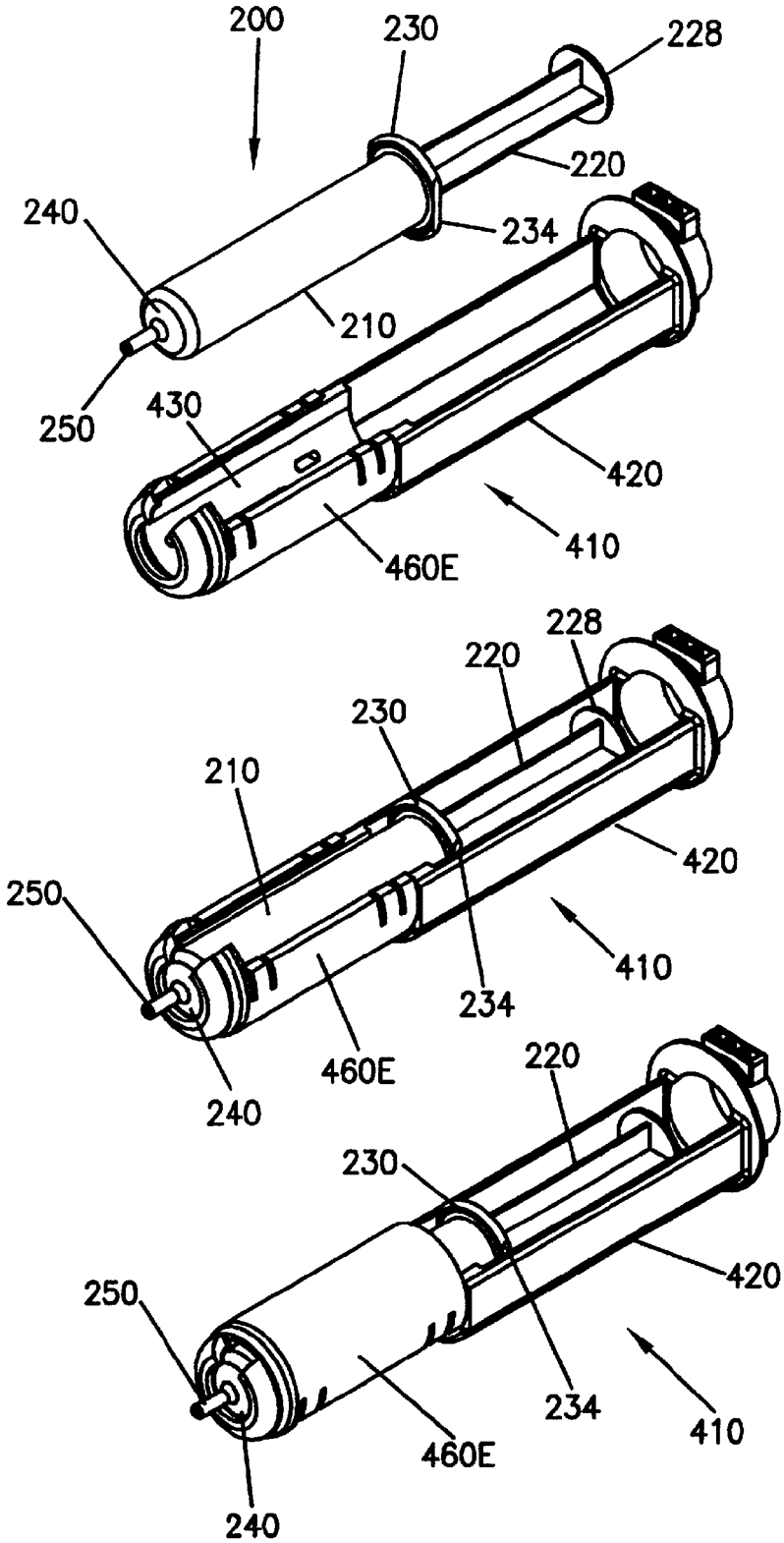

An example of a widened, rotating retaining member 460e is illustrated in FIG. 4I. Retaining member 460e is rotatably attached (about the longitudinal axis of carrier 410) to second portion 430 and extends generally along the entire length of second portion 430. After syringe 200 is top loaded into carrier 420, retaining member 460e can be rotated to form a cover over second section 430. Retaining members 460d and 460e can be transparent or formed with cut away sections to enhance the visibility of syringe 200.

Figure 5A:
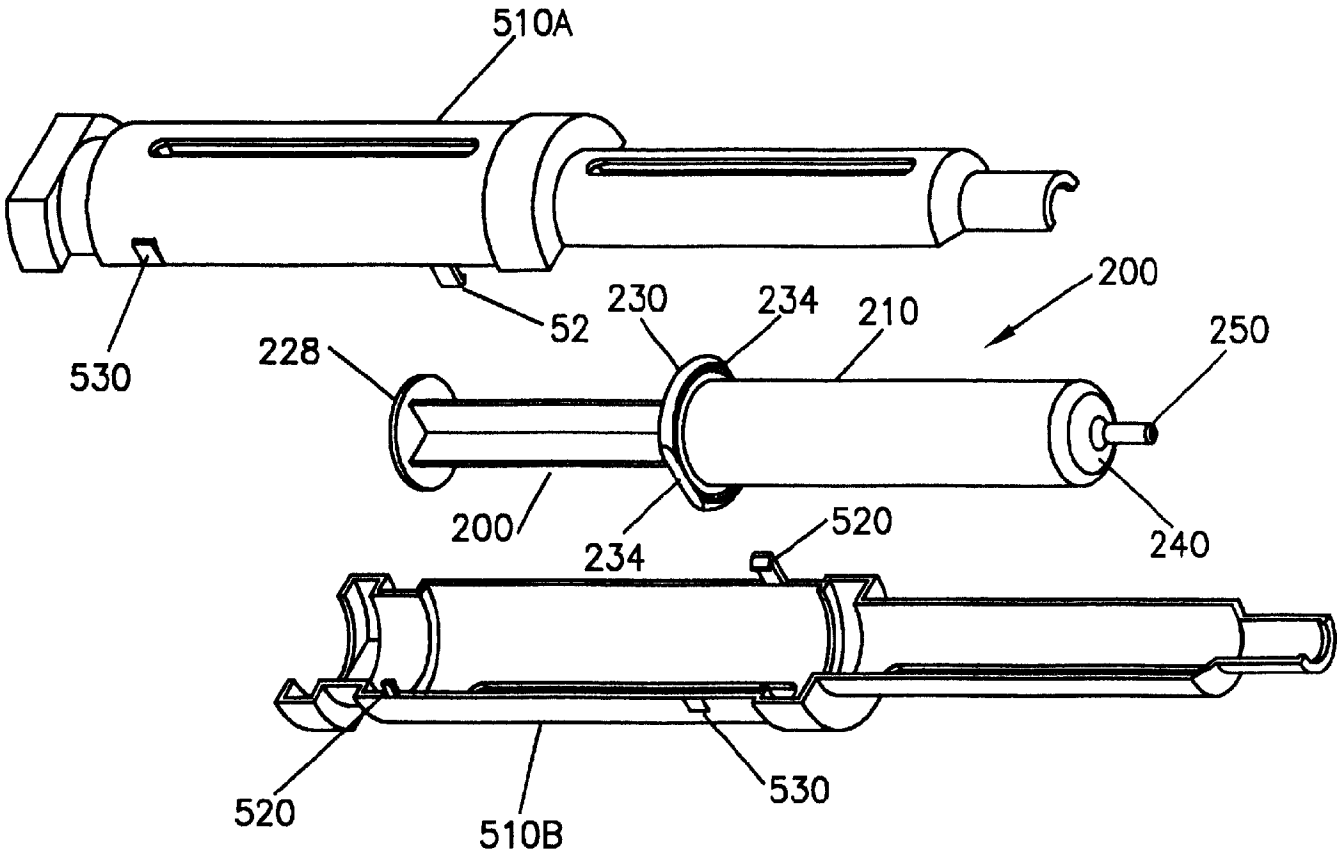
FIG. 5A illustrates a perspective view of an embodiment of an adapter including separate, generally identical sections in an unconnected state.
Figure 5B:
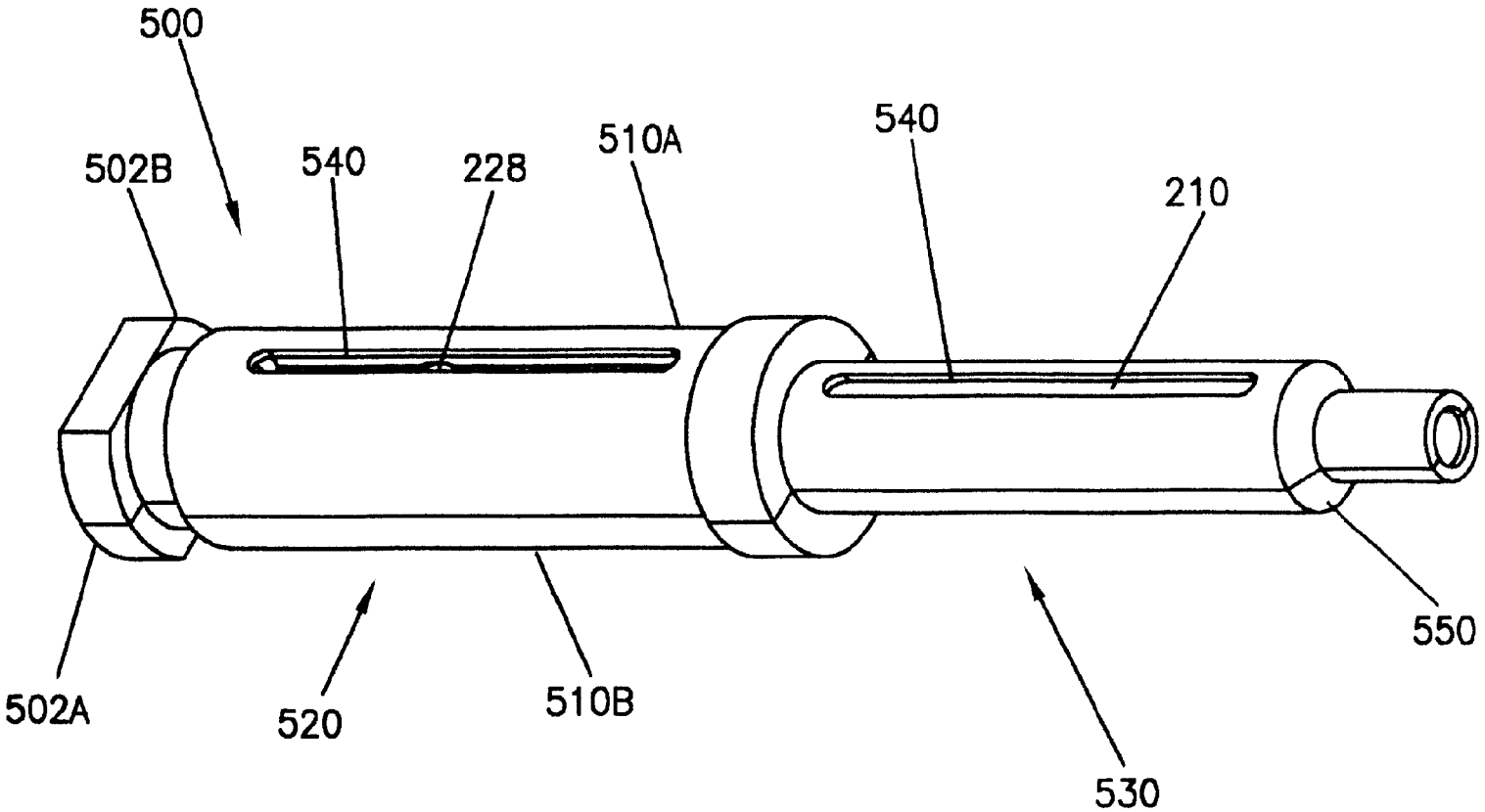
FIG. 5B illustrates a perspective view of the adapter of FIG. 5A in a connected state.

In some cases it may be desirable to manufacture the adapter of the present invention to be disposable after one or more uses. Such disposable adapters are preferably manufactured in an inexpensive manner. In FIGS. 5A and 5B, an embodiment of a preferably disposable adapter 500 is illustrated. Adapter 500 preferably includes two generally identical members 510a and 510b. Fabricating adapter 500 from two generally identical members 510a and 510b may substantially reduce manufacturing costs. Members 510a and 510b may for example be fabricated to "snap" together (for example, via extension members 520 and cooperating catch members 530) and provide visible, audible and/or tactile feedback to indicated proper connection.

In use, syringe 200 is preferably seated in one of members 510a or 50b. The other portion is then, for example, snapped into place to encompass syringe 200 within the resultant adapter 500 (see FIG. 5B). When assembled, portions 510a and 510b form a rearward section that houses plunger extension rod 220 and a forward portion that houses syringe barrel 210. At or near a rearward end of adapter 500, members 510a and 510b preferably form a connecting section including first mounting flange 502a and a second mounting flange 502b adapted to removably attach adapter 500 to injector 10 as described above. As illustrated in FIG. 5b, adapter 500 encompasses both syringe barrel 210 and plunger extension rod 220 to retain/stabilize syringe 200. The side walls of adapter 500 can be formed with a generally flat or flattened profile to interact with/abut generally flat section(s) 234 of syringe flange 230 to prevent rotation of syringe 200 about its axis within adapter 200.

To facilitate viewing of either plunger extension rod 220 or barrel 210, adapter 500 can be formed with cut out window sections 540. Moreover, any portion or all of adapter 500 can be transparent.

Adapter 500 provides resistance to the forward force applied to plunger extension rod 220 by abutment of syringe transition region 240 with a radially inward extending shoulder section 550. The advantages of providing such resistance/retention by abutment of syringe transition region 240 discussed above in connection with other embodiments of adapter of the present invention are also provided by adapter 500.

Figure 6A:
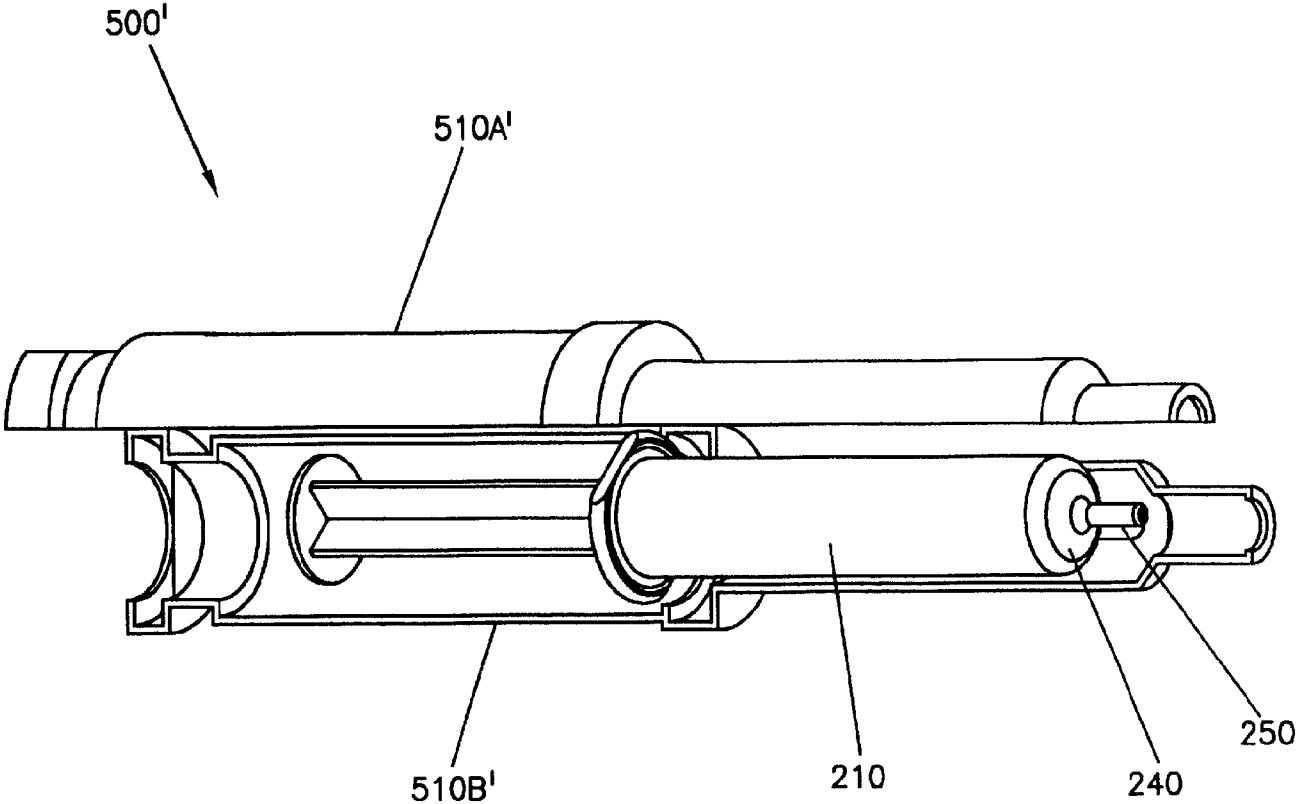
FIG. 6A illustrates a perspective view of another embodiment of an adapter including generally identical sections that are hingingly attached via a side wall thereof.
Figure 6B:
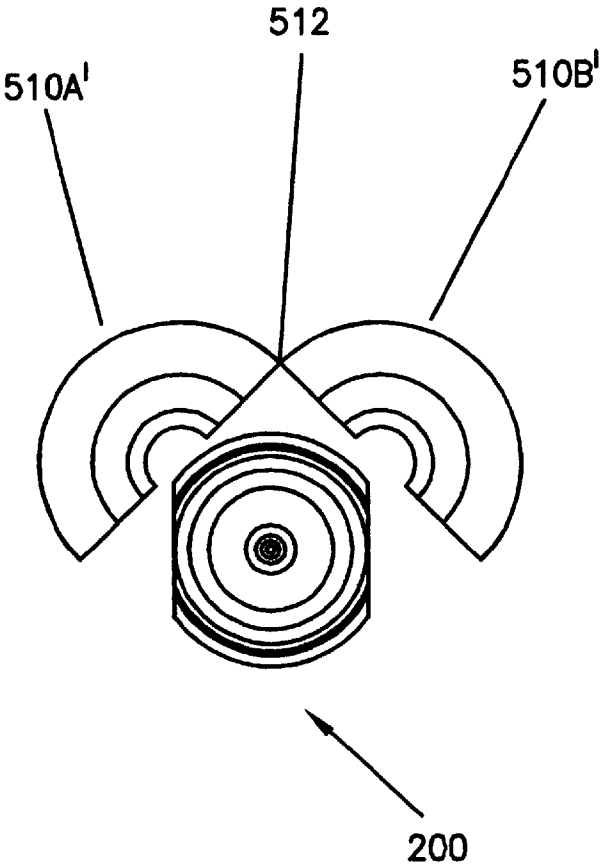
FIG. 6B illustrates a front view of the adapter of FIG. 6A in an open state.
Figure 6C:
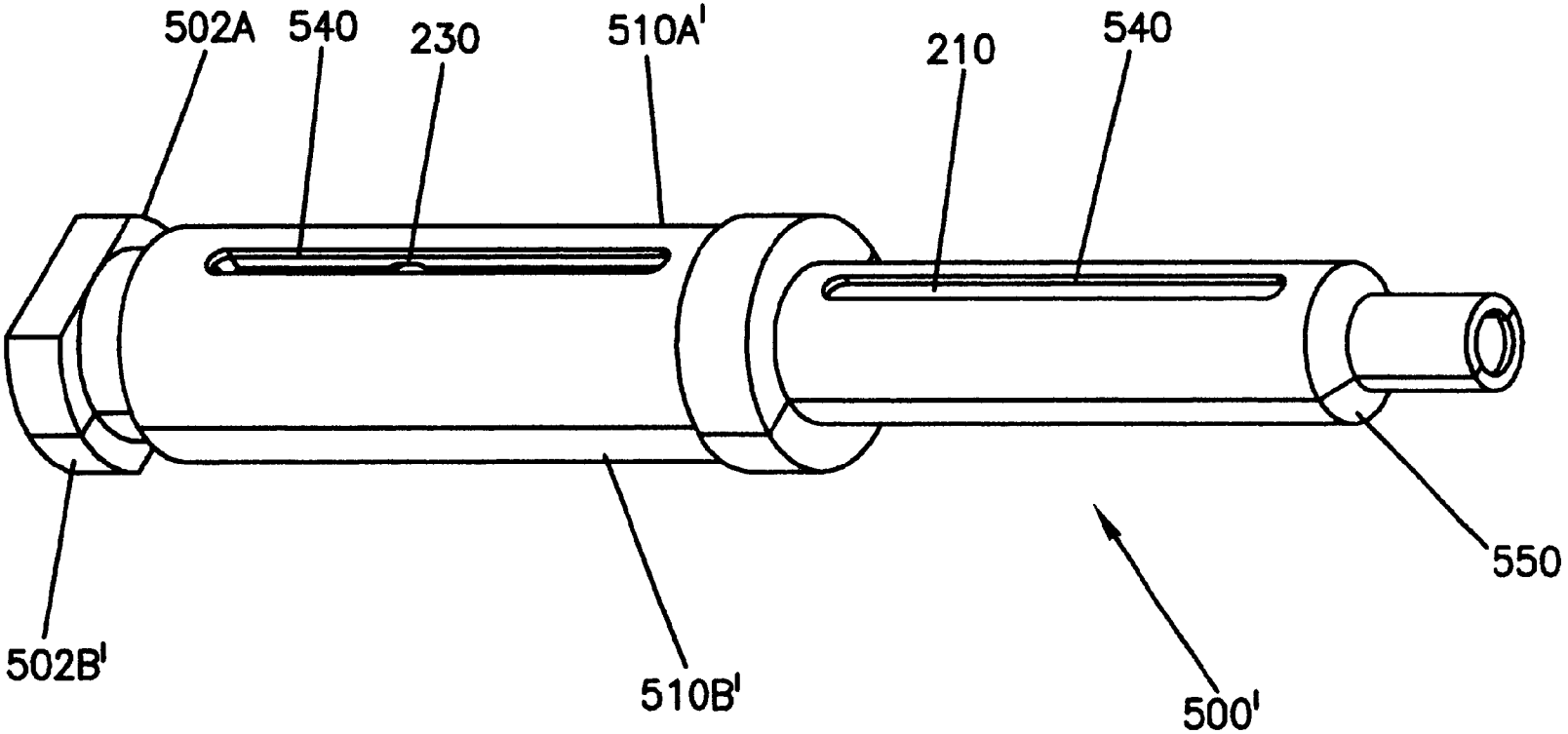
FIG. 6C illustrates a perspective view of the adapter of FIG. 6A in a closed state.

Another embodiment of an adapter 500' is illustrated in FIGS. 6A through 6C. Adapter 500' is generally identical to adapter 500 except that adapter 500' is formed from the connection of a first portion 510a' and a second portion 510b' that are initially hinged together, for example by a notched plastic hinge 512 as known in the art) as best illustrated in FIGS. 6A and 6B.

Figure 7A:
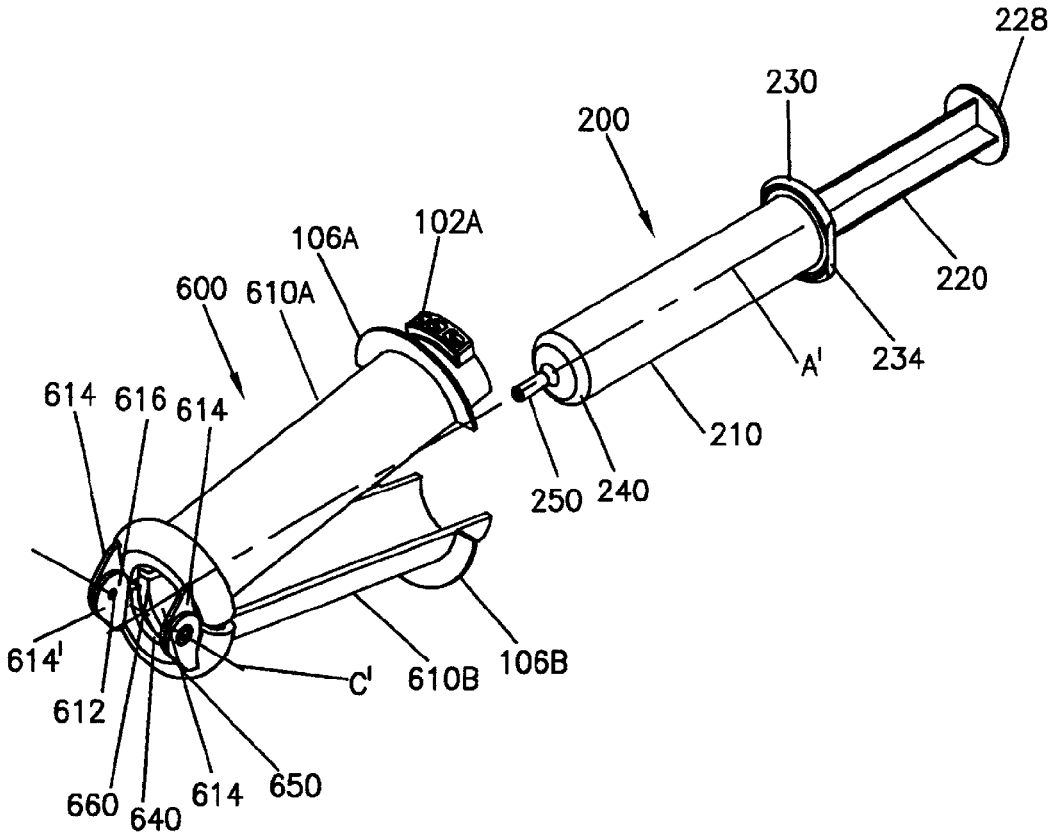
FIG. 7A illustrates a perspective view of another embodiment of an adapter including generally identical sections that are attached at a front end thereof in an open state.
Figure 7B:
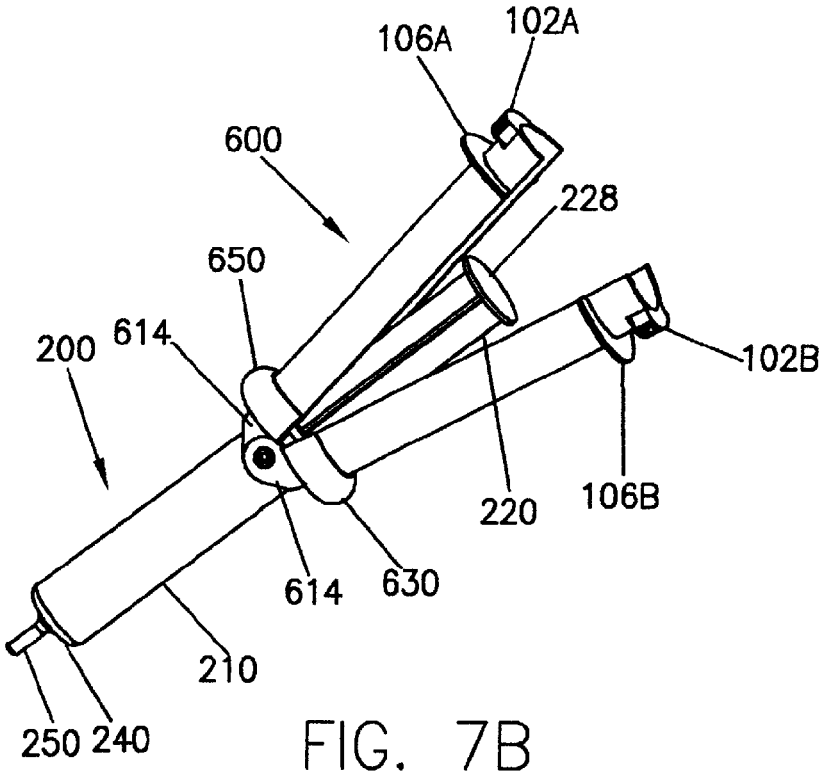
FIG. 7B illustrates the adapter of FIG. 7A with a syringe loaded therein.
Figure 7C:
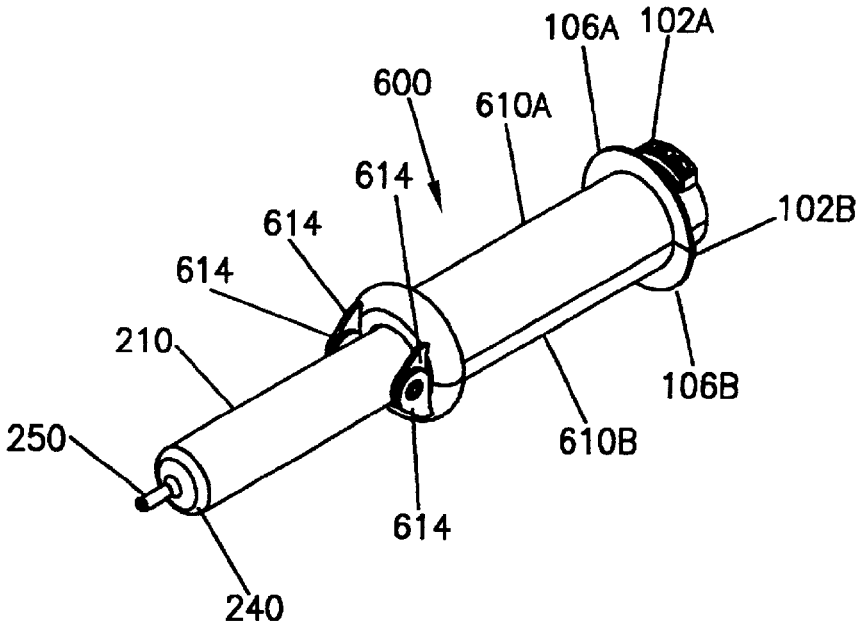
FIG. 7C illustrates the adapter of FIG. 7A wherein the sections thereof have been hingingly closed for connection of the adapter to an injector.

FIGS. 7A through 7C illustrate another embodiment of an adapter 600 of the present invention. Adapter 600 includes a first member 610a and a second member 610b that are attached via a forward hinge mechanism. The hinge mechanism preferably includes a generally cylindrical member 612 on an extending member 614 of one of first member 610a and second 610b that is rotatably seatable in a passage 616 formed in an extending member of the other of first member 610a and second member 610b. Extending members 614 preferably extend forward on each side of a forward end of each of first member 610a and second member 610b as illustrated in FIG. 7A.

First member 610a includes first retaining flange 102a as described above, while second member 610b includes second retaining flange 102b that operate to connect adapter 600 to injector 10 as described above. First member 610a preferably includes one half of a drip flange 106a, while second member 610b preferably includes the other half of a drip flange 106b.

To seat syringe 200 within adapter 600, first member 610a and second member 610b are preferably rotated about an axis C' of hinging mechanism (which axis is generally perpendicular to the orientation of longitudinal axis A' of adapter 600) to an open position as illustrated in FIGS. 6A and 6B. Barrel 210 of syringe 200 is then passed through an opening 640 formed at the forward end of adapter 600. Syringe 200 is advanced forward through passage 640 until flange 230 abuts radially inward extending shoulder 650 to retain syringe 200 within adapter 600 and provide resistance to forward force exerted upon plunger extension rod 220 by piston 40'. First member 610a and second member 610b are then rotated to a closed position. As discussed above in connection with adapter 100, shoulder 650 may include a raised (rearward extending) abutment ridge 660 to ensure that contact is made with syringe flange 230 near the point where syringe flange 230 is connected to barrel 210. Forward force exerted upon shoulder 650 assists in maintaining adapter 600 in a closed position as illustrated in FIG. 6C.

Like adapters 500 and 500', first member 610a and second member 610b can be formed to be generally identical. Fabrications costs of adapter 600 can thereby be reduced.

Figure 8A:
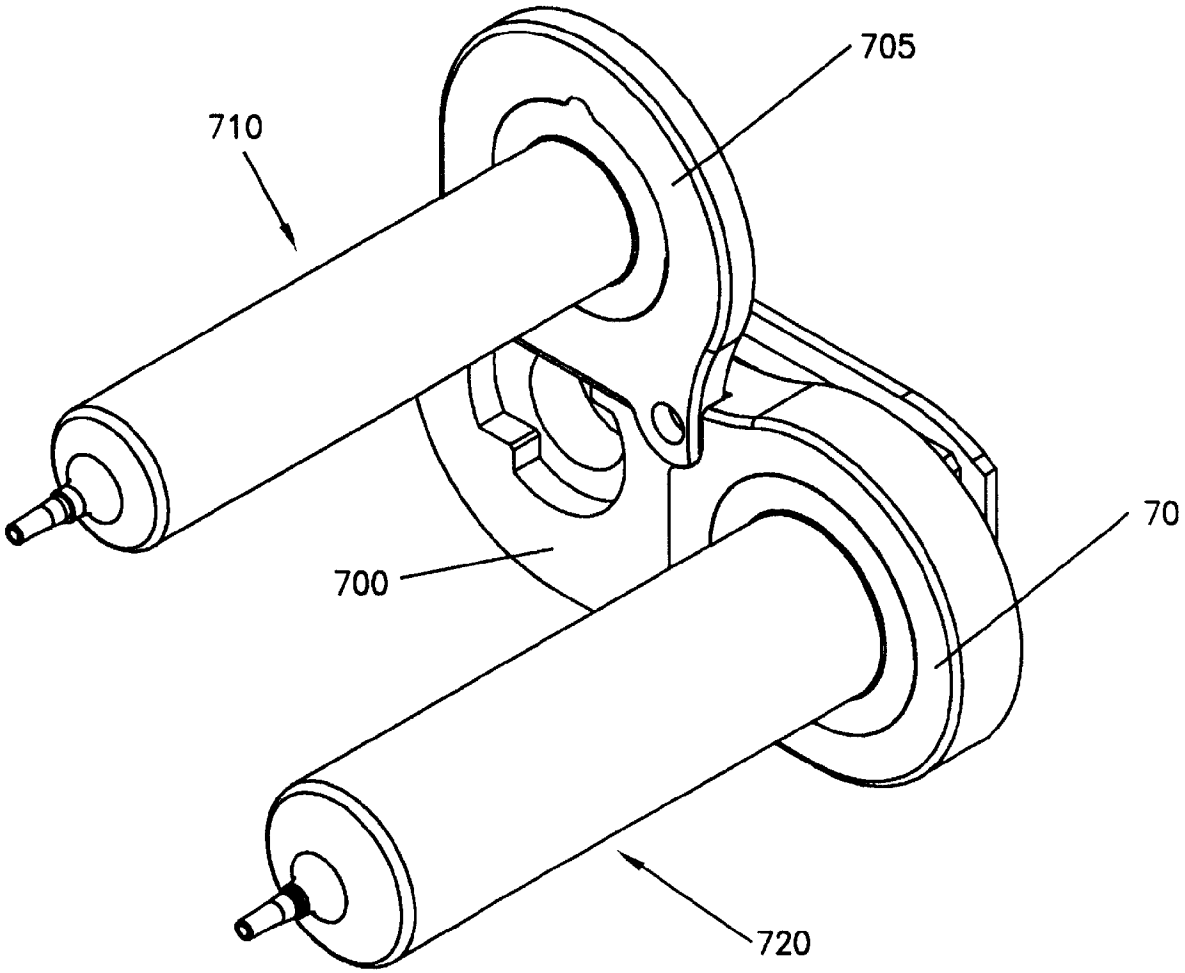
FIG. 8A illustrates a perspective view of a portion of an injector having at least one removable face plate for attachment of a syringe or an adapter thereto.

In all of the embodiment discussed above, the adapter is attached to injector 10 via mounting flanges on a rearward portion or section of the adapter. There are, however, alternative manners in which an adapter of the present invention may be attached to injector 10. As illustrated in FIG. 8A, for example, an injector may include a front wall 700 to which at least one removable face plate 705 is attached. The injector of FIG. 8A is designed for use in an MRI procedure and includes a first, contrast syringe 710 attached to a first face plate 705 and a second, saline syringe 720 attached to a second face plate 705'. In the embodiment of FIG. 8A, face plate 705 is rotated upward to be detached from the injector.

Figure 8B:
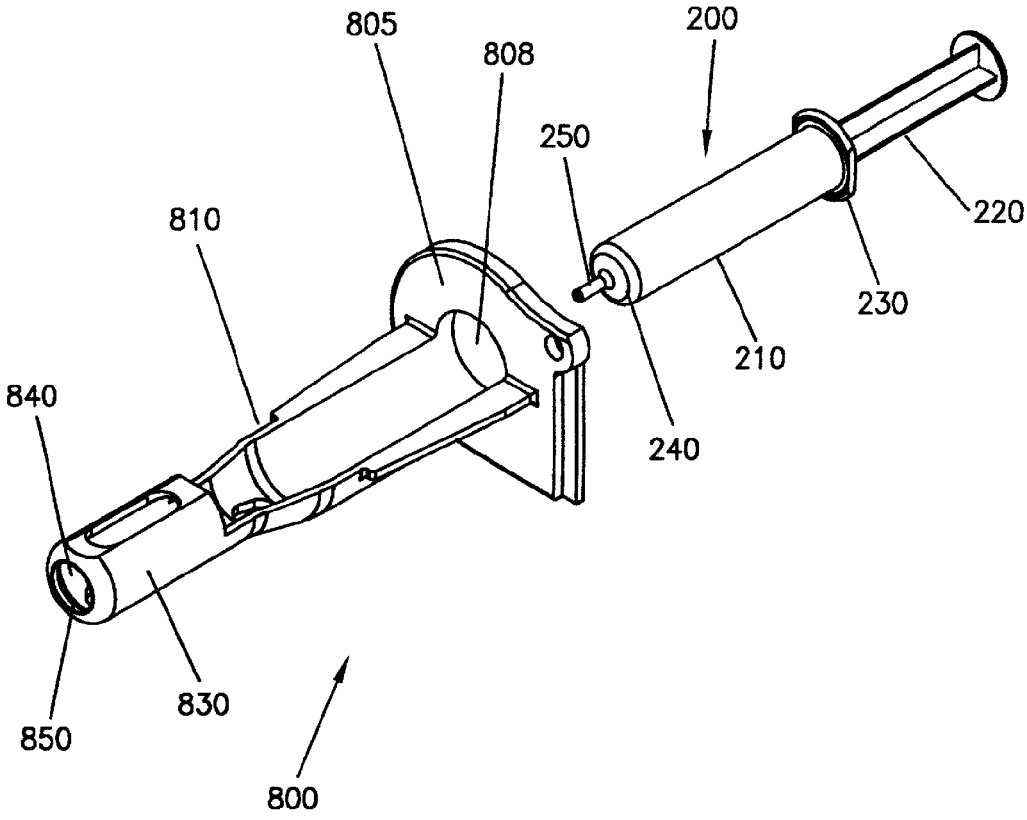
FIG. 8B illustrates a perspective view of an embodiment of an adapter for use with the injector of FIG. 8A.

FIG. 8B illustrates an embodiment of an adapter 800 including a carrier 810 formed integrally or attached to a face plate 805 suitable for attachment to the injector of FIG. 8A. Syringe 200 can be "breach" loaded into carrier 810 by first tilting syringe 200 and advancing barrel 210 of syringe 200 in a forward direction through passage 840 formed in a forward most position of an enclosed forward section 830 of carrier 810. Syringe 200 is advanced until syringe cone region 240 abuts radially inwardly extending shoulder 850 that defines passage 840. Face plate 805 includes a passage 808 therein through which a piston (not shown) of the injector of FIG. 8A can pass to cooperate with plunger extension rod 220.

Figure 8C:
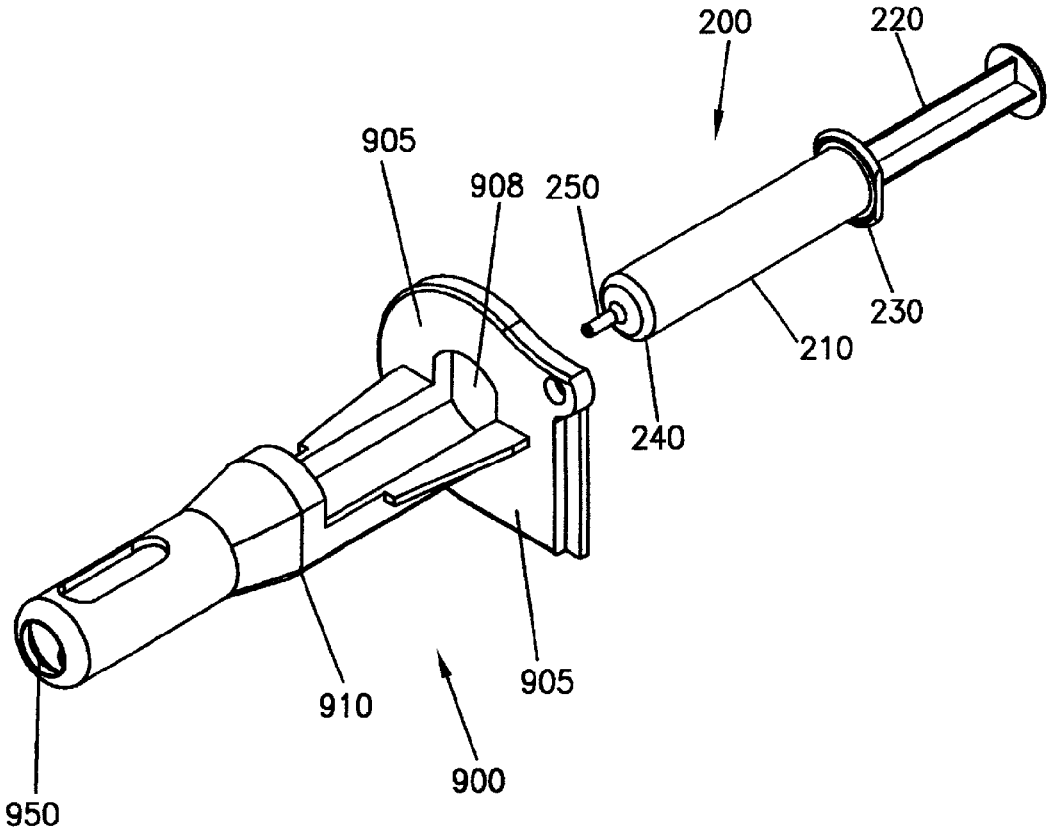
FIG. 8C illustrates a perspective view of another embodiment of an adapter for use with the injector of FIG. 8A.

FIG. 8C illustrates an embodiment of an adapter 900 that includes a carrier 910 attached to a removable face plate 905. In this embodiment, syringe 200 is advanced through passage 908 in face plate 902. Syringe 200 is advanced forward until cone region 240 abuts radially inward extending shoulder 950 of carrier 910.

Figure 8D:
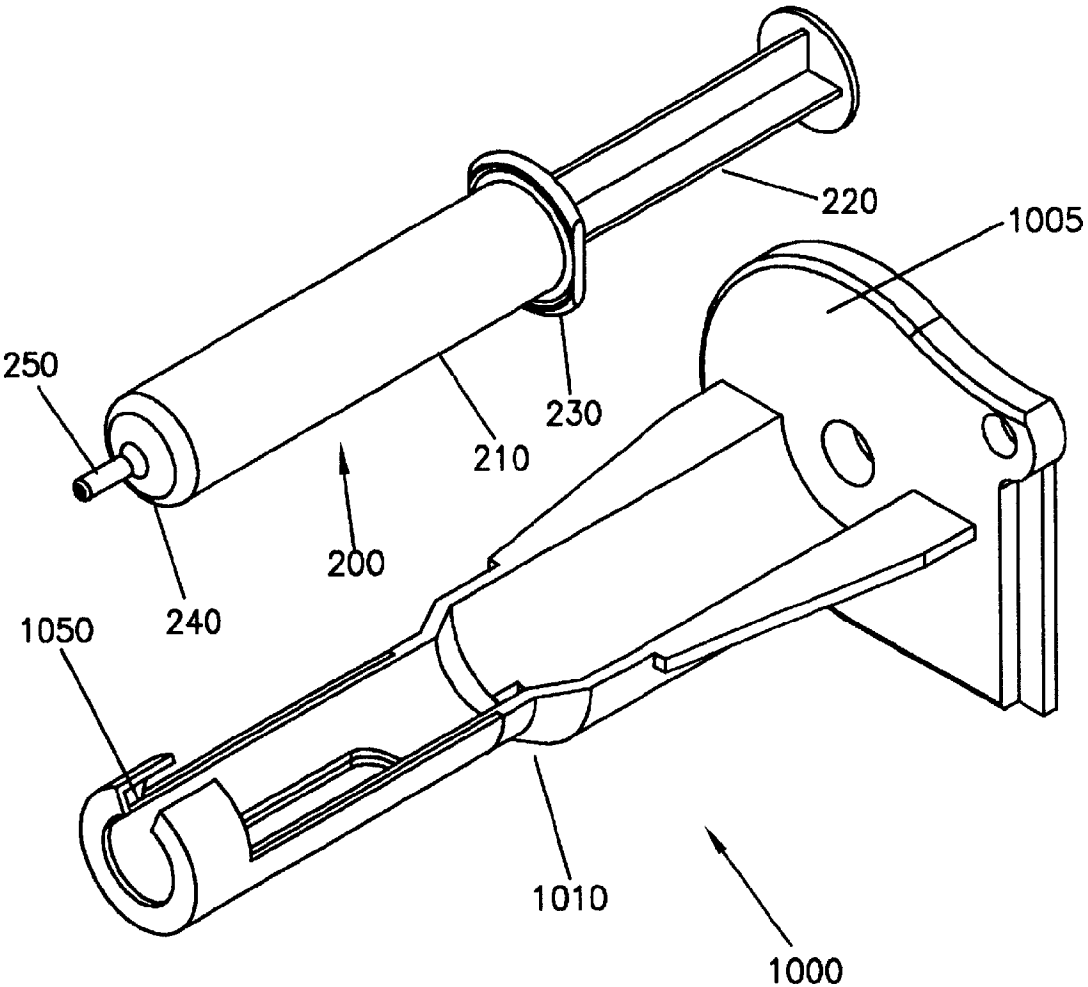
FIG. 8D illustrates a perspective view of another embodiment of an adapter for use with the injector of FIG. 8A.

FIG. 8D illustrates an embodiment of an adapter 1000 that includes a carrier 1010 attached to a removable face plate 1005. Syringe 200 is loaded into carrier 1010 from the top by dropping syringe 200 into carrier 1010. When seated in carrier 1010, syringe 200 abuts radially inward extending shoulder 1050 of carrier 1010. The top of carrier 1010 is maintained in an open state over the length of carrier 1010 to facilitate removal of syringe 200 even when connected to a fluid path element.

Figure 8E:
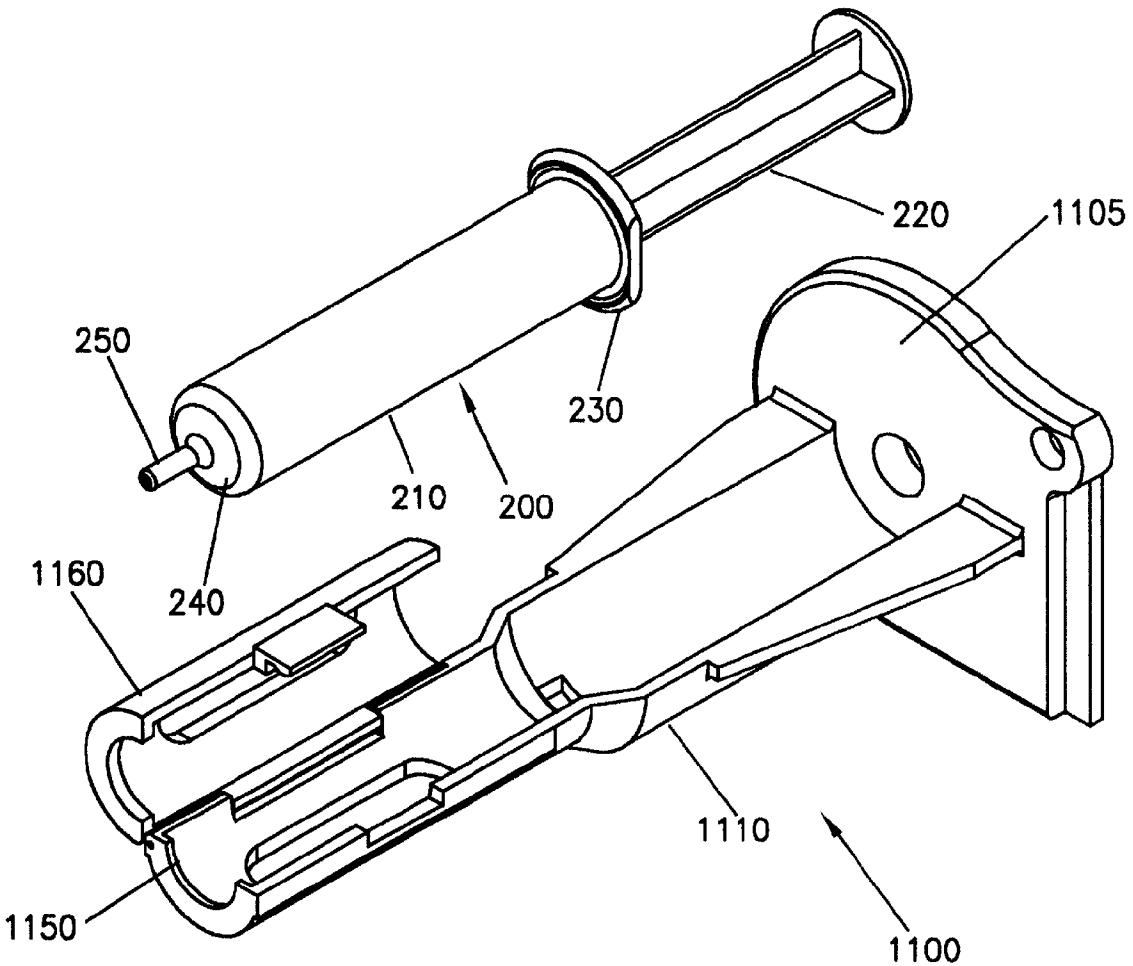
FIG. 8E illustrates a perspective view of another embodiment of an adapter for use with the injector of FIG. 8A.

FIG. 8E illustrates an embodiment of an adapter 1100 that includes a carrier 1110 attached to a removable face plate 1105. Like adapter 1010, syringe 200 is loaded into carrier 1110 from the top by dropping syringe 200 into carrier 1110.

When seated in carrier 1110, syringe transition region 240 abuts radially inward extending shoulder 1150 of carrier 1110. Carrier 1110 includes a hinging cover section 1160 that can be rotated to a closed position to form a cover/retainer over at least a portion of syringe barrel 210 to assist in retaining/stabilizing syringe 200. Shoulder 1050 can be rotatable to capture syringe 200 and support it.

Figure 9A:
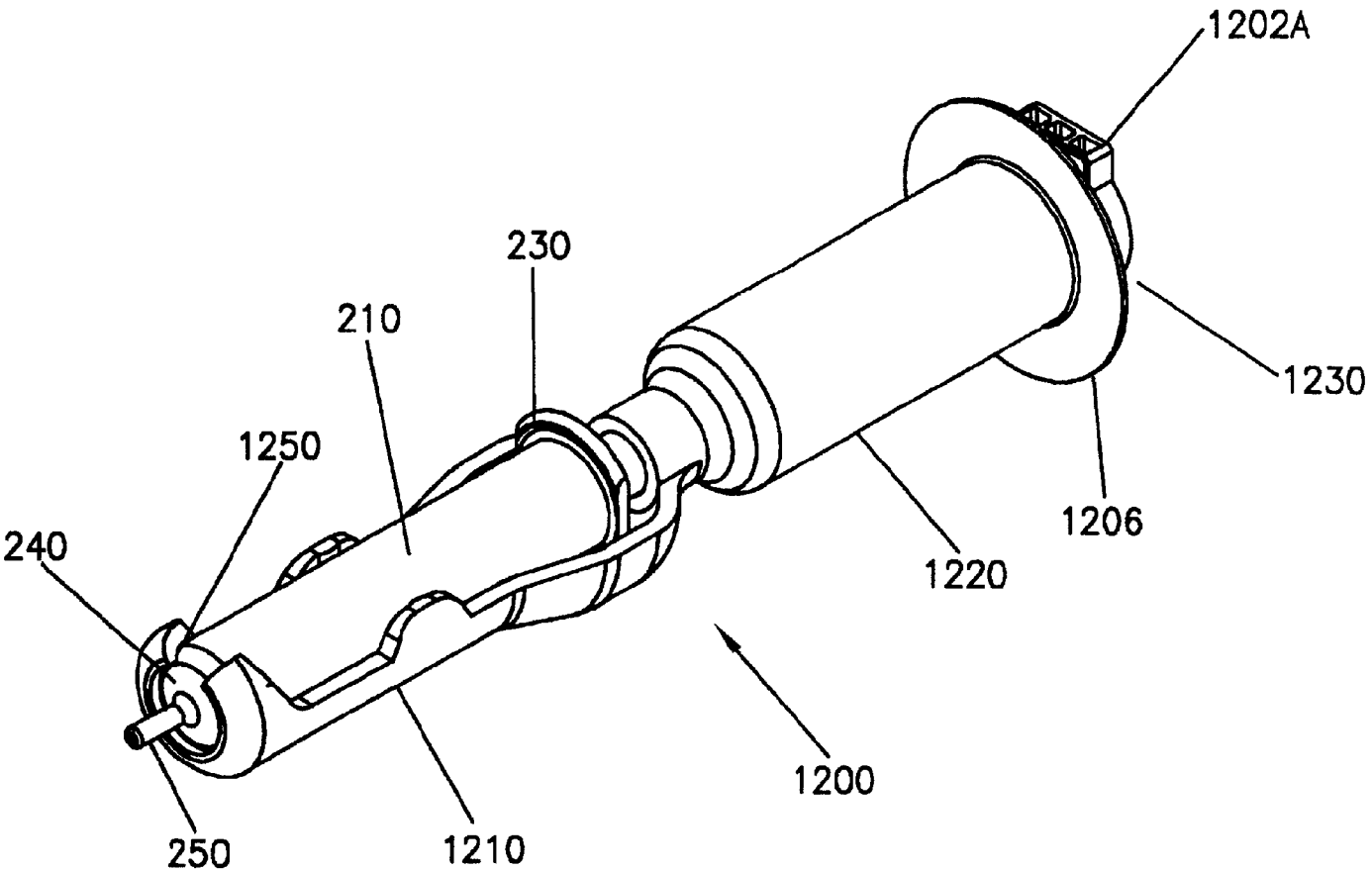
FIG. 9A illustrates a perspective view of an embodiment of an adapter assembly or system in which a push rod performs the function of a syringe plunger extension rod.
Figure 9B:
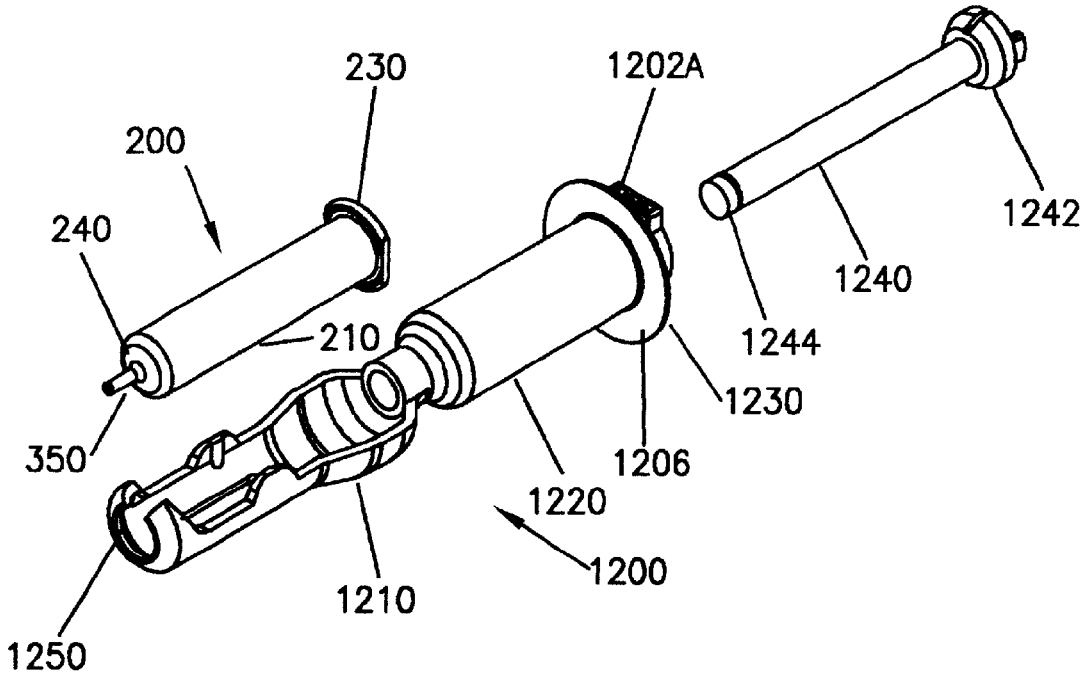
FIG. 9B illustrates a perspective view of the adapter assembly of FIG. 9A in a disconnected state.
Figure 9C:
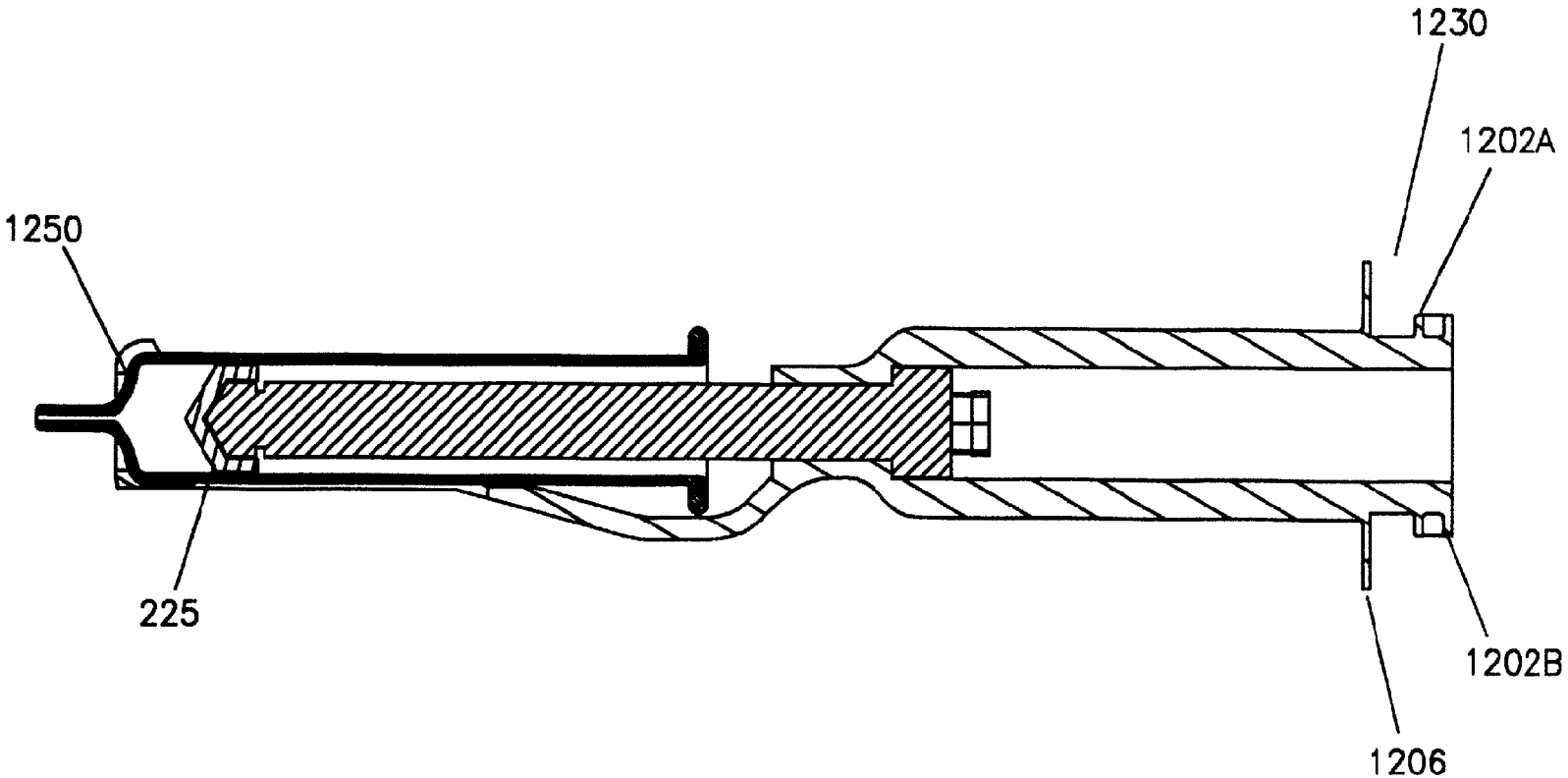
FIG. 9C illustrates a cross-sectional view of the adapter assembly of FIG. 9A.

FIGS. 9A through 9C illustrate an embodiment of an adapter system 1200 including a carrier section 1210, an intermediate section 1220, and a rearwardmost connecting section 1230. Adapter 1200 further includes a push rod 1240. Syringe 200 is seated in carrier section 1210 by dropping syringe 200 into carrier section 1210. Cone region 240 abuts shoulder 1250 of carrier section 1210. The plunger extension rod (not shown) has been removed from connection with syringe plunger 225. In many cases, such plunger extension rods are connected to plunger 225 via threading on the forward end of the plunger extension rod.

Push rod 1240 extends through intermediate section 1220 to cooperate with plunger 225 to apply force to plunger 225. In the case of a prefilled syringe, there is typically no need to retract plunger 225 within syringe 200. In such cases, there is no need to establish an engaging connection (threaded or otherwise) between a forward end of push rod 1240 and plunger 225 to resist the force of and couple plunger 225 to push rod 1240 during a retracting motion of push rod 1240. This greatly simplifies the construction and operation of push rod 1240 and the injector.

In operation of adapter system 1200, push rod 1240 makes a connection with a piston (not shown in FIGS. 9A through 9C; see FIG. 1A) of the injector through a connective coupling 1242 on a rearward end of push rod 1240. Connecting section 1230 is removably attached to the injector via the cooperation of mounting flanged 1202a and 1202b and drip flange 1206 with the injector as described above. Syringe 200 can be top loaded into carriage section 1210 either before or after connection of adapter 1205 to the injector via connecting section 1230. Push rod 1240 is advanced forward through intermediate section 1220 by the injector piston until forward end 1244 pilots into syringe plunger 225 to abut a rearward facing wall section within plunger 225. Once again, no secured connection to resist a rearward motion need be effected between push rod forward end 1244 and plunger 225 in, for example, the case of a prefilled syringe or in any other case that retraction of plunger 225 within syringe 200 will not be required. Push rod forward end 1244 is preferably of generally the shape of the rearward facing interior of plunger 225. In this manner, push rod forward end 1244 provides support to plunger 225 to maintain the shape of plunger 225 during use of syringe 200. In many cases, plunger 225 will be fabricated predominantly from an elastomeric cover material. If the side walls of plunger 225 do not make adequate sealing contact with the interior side wall of syringe barrel 210, leakage of contrast to the rear of plunger 225 can occur during advancement of plunger 225.

FIGS. 10A through 10D illustrate another embodiment of an adapter system 1300 of the present invention. Similar to adapter system 1200, adapter system 1300 includes a carrier section 1310, an intermediate section 1320, and a rearwardmost connecting section 1330. Adapter system 1300 further includes or operates with a push rod 1340. Syringe 200 is seated in open carrier section 1310 by placing syringe 200 into carrier section 1310 from above (and can be seated therein or removed thereform without removal or any attached tubing). Forward transition or cone region 240 abuts a shoulder portion 1350 of carrier section 1310.

To minimize fabrication costs of adapter system 1300, it is desirable that the option of using, for example, less expensive, lower-strength polymeric materials be available. Because the top portion of carrier section 1310 and shoulder 1350 are open for ease of removal of syringe 200, asymmetrical loading of connecting section 1330 can occur if cone region 240 of syringe 200 contacts a bottom portion of shoulder portion 1350 (as in the case of shoulder 1240, for example) during advancement of push rod 1340. The resulting bending moment about connection section 1330 can cause failure of adapter system 1300. To substantially reduce or eliminate asymmetrical loading, shoulder portion 1350 is preferably shaped to prevent such asymmetrical loading by, for example, being open on the top and bottom thereof (see, FIG. 10B). Removing a bottom edge of abutment shoulder 1350 where cone region 240 of syringe 200 would otherwise rest results in generally symmetrical loading about the axis of adapter system 1300 (and syringe 200) and substantially reduces or removes lateral loads and bending moments during forward plunger advancement. Axial load applied to the end of adapter assembly 1300 is maximized while lateral load is minimized.

Figure 10A:
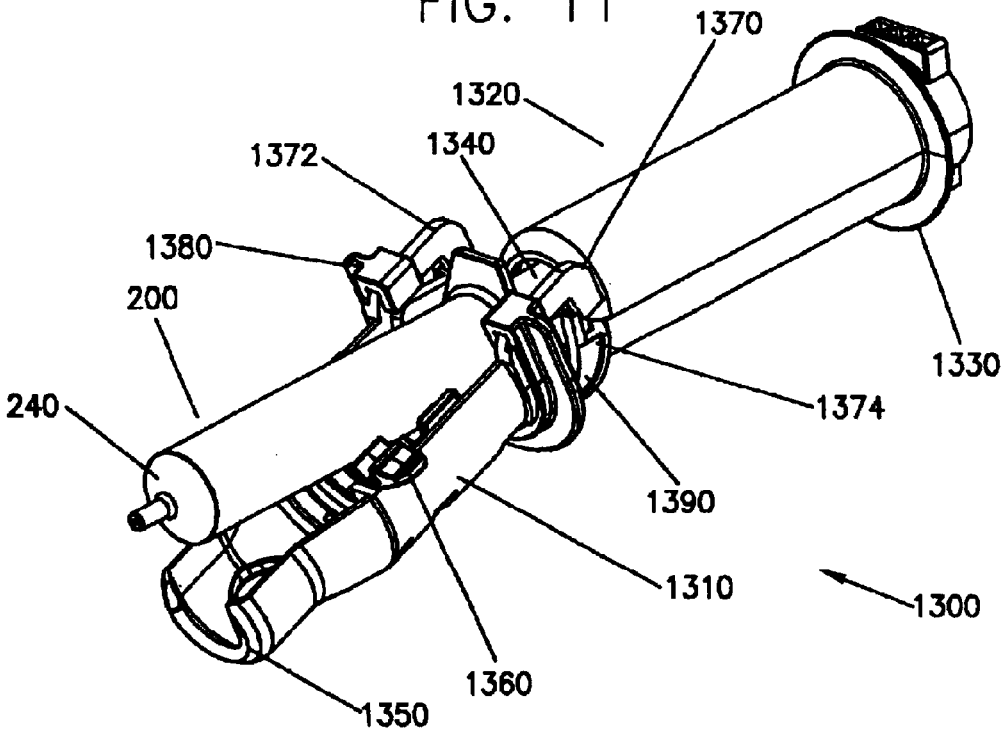
FIG. 10A illustrates a perspective view of an embodiment of an adapter assembly or system in which the carrier section hinges with respect to the intermediate section to allow removal of the syringe after an injection procedure without retraction of the injector drive member.
Figure 10B:
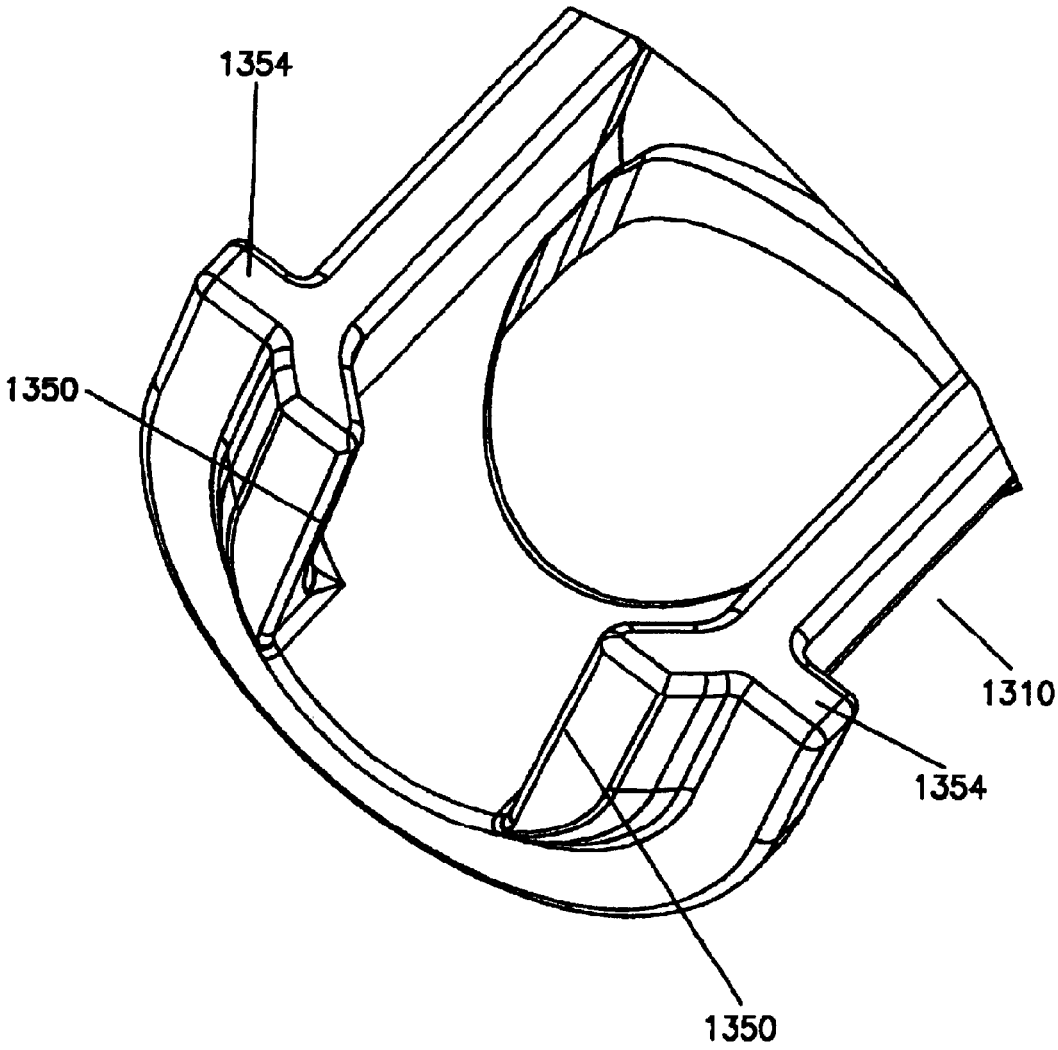
FIG. 10B illustrates an expanded perspective view of the forward portion of the carrier section.

In addition, enforcements such as a rib 1354 can be added to carrier section 1310 to limit wall flexing by increasing the material strength as illustrated in FIG. 10B. Likewise, extension 1556 and 1558 illustrated in FIG. 12B can be formed integrally on the front portion of carrier section 1510 of adapter assembly 1500 (or adapter assembly 1300). Cone or transition region 240 of syringe 200 preferably does not contact extensions 1556 and 1558. When syringe 200 contacts shoulder portions 1350 (not shown in FIG. 12B) with forward force, syringe 200 can act as a wedge and force the opposing portions of shoulder 1350 apart. Forming extension 1556 and 1558 around the circumference of the front of carrier section 1510 creates hoop forces or stresses that help prevent such deformation. Extensions 1556 and 1558 are preferably spaced sufficiently at the top portion thereof to allow ready removal of syringe 200 and any attached tubing as discussed above.

Figure 10C:
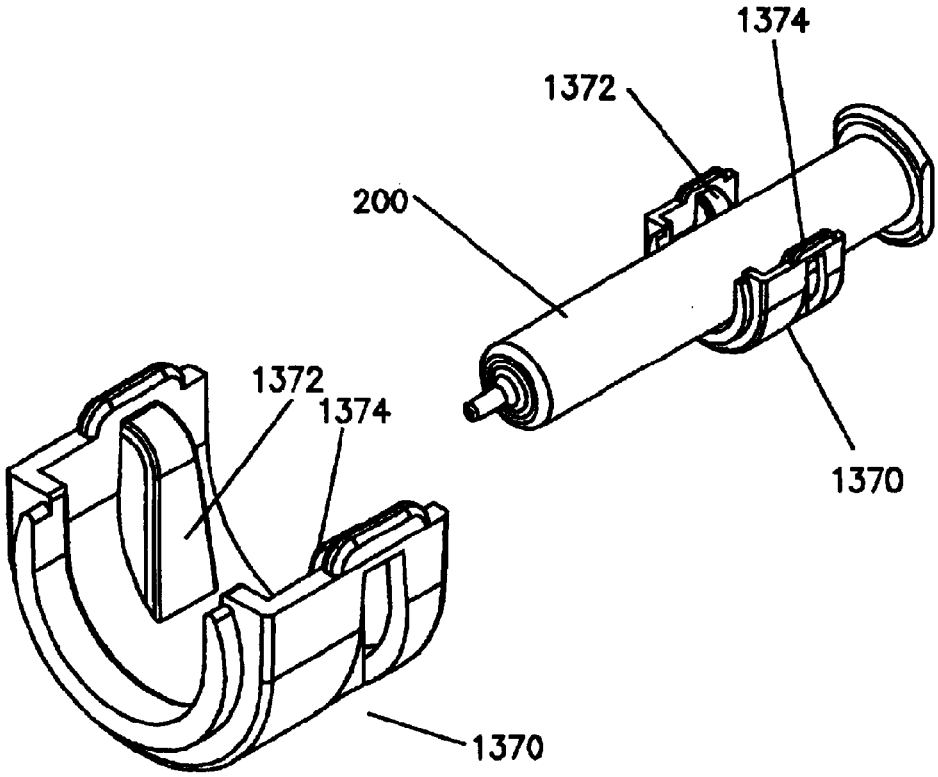
FIG. 10C illustrates a perspective view of an embodiment of a syringe retainer for use in the adapter system.
Figure 10D:
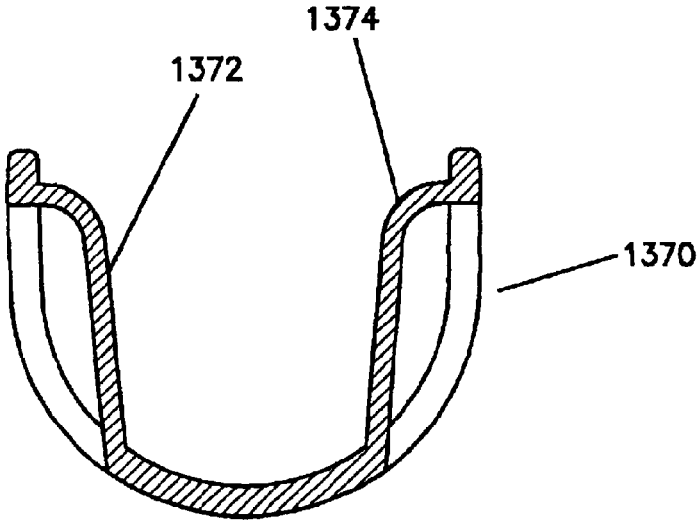
FIG. 10D illustrates a front cross-sectional view of the syringe retainer of FIG. 10C.

In addition to a rotating retaining member 1360 (which operates generally in a manner as described for retaining member 460 of FIGS. 4A through 4C) or in lieu thereof, adapter system 1300 preferably includes a biasing retaining section 1370 illustrated in FIG. 10C and 10D. In the embodiment of FIGS. 10C and 10D, retaining section 1370 includes two flexing retaining member 1372 and 1374 inset from the inside wall of carrier section 1310 to provide a pressure fit against syringe 200, thereby securing syringe 200 in place. Retaining section 1370 assists, for example, in retaining syringe 200 within carrier section 1310 when the injector head (not shown in FIGS. 10A-D) is rotated to a position other than horizontal when syringe 200 is placed with carriage section 1310. Should, for example, the injector head (and thereby carrier section 1310) be in a vertical orientation, retaining section 1370 prevents the syringe from falling out of carrier section 1310 even before retaining member 1360 can be rotated to a closed position.

In the embodiment of FIG. 10A, retainer section 1310 is movably connected (for example, hingedly or even removably connected) to intermediate section 1320. By, for example, rotating carrier section 1310 downward so that syringe 200 can be pulled forward without contacting the forward portion of carrier 1310, syringe 200 can be released and removed without retracting the plunger thereof following a full or partial injection.

In the embodiment of FIG. 10A, carrier section 1310 is hingedly attached to intermediate section 1320 via pin joints (not shown) on each side thereof.

Carrier section 1310 rotates about such pin points when closing the adapter assembly until extending members 1370 and 1372 contact abutment surfaces 1374 on intermediate section 1320. At that point, intermediate section 1320 is generally aligned with carrier section 1310, and carrier section 1310 is in position for shoulder 1350 to abut syringe transition region 240. A locking ring 1380 is preferably slidably positioned on extending members 1370 and 1372. After carrier section 1310 is rotated to a closed position, locking ring 1380 is slid rearward to abut a flange 1390 formed on the lower half of the front of intermediate section 1310 to lock carrier section 1310 in a closed position.

Figure 11:
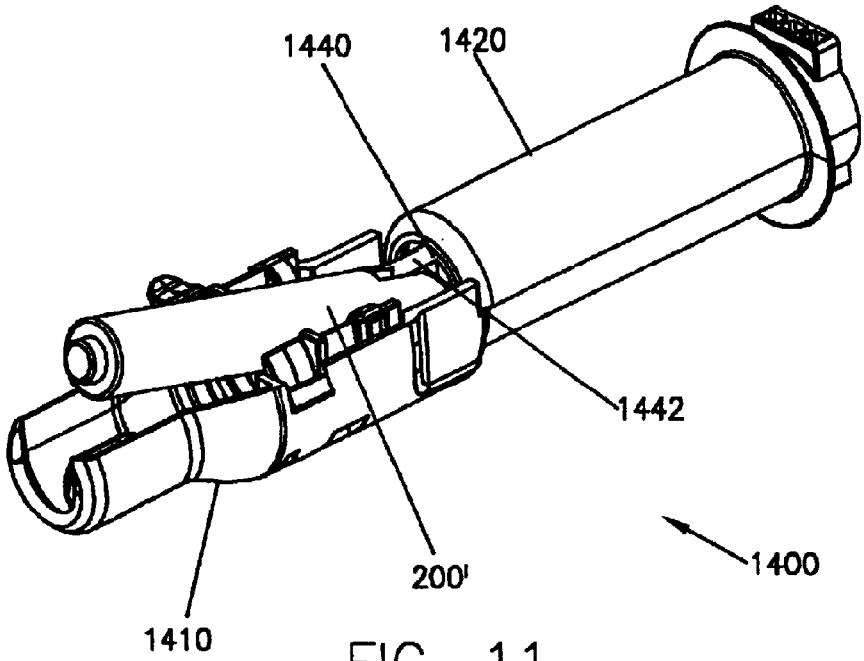
FIG. 11 illustrates a perspective view of an adapter system in which the push rod hinges to allow removal of the syringe after an injection procedure without retraction of the injector drive member.

FIG. 11 illustrates another embodiment of an adapter system 1400 that is very similar to adapter system 1300. However, carrier section 1410 is not hingedly attached to intermediate section 1420. In this embodiment, push rod 1440 includes a movable section (for example, hinging or rotating section 1442) positioned forward of intermediate section 1420. Hinging section 1442 allows syringe 200 to be moved (rotated, in this embodiment) out of alignment with the axis of adapter system 1400 so that syringe 200 can be removed without retracting the drive member of the injector following a full or partial injection.

Figure 12A:
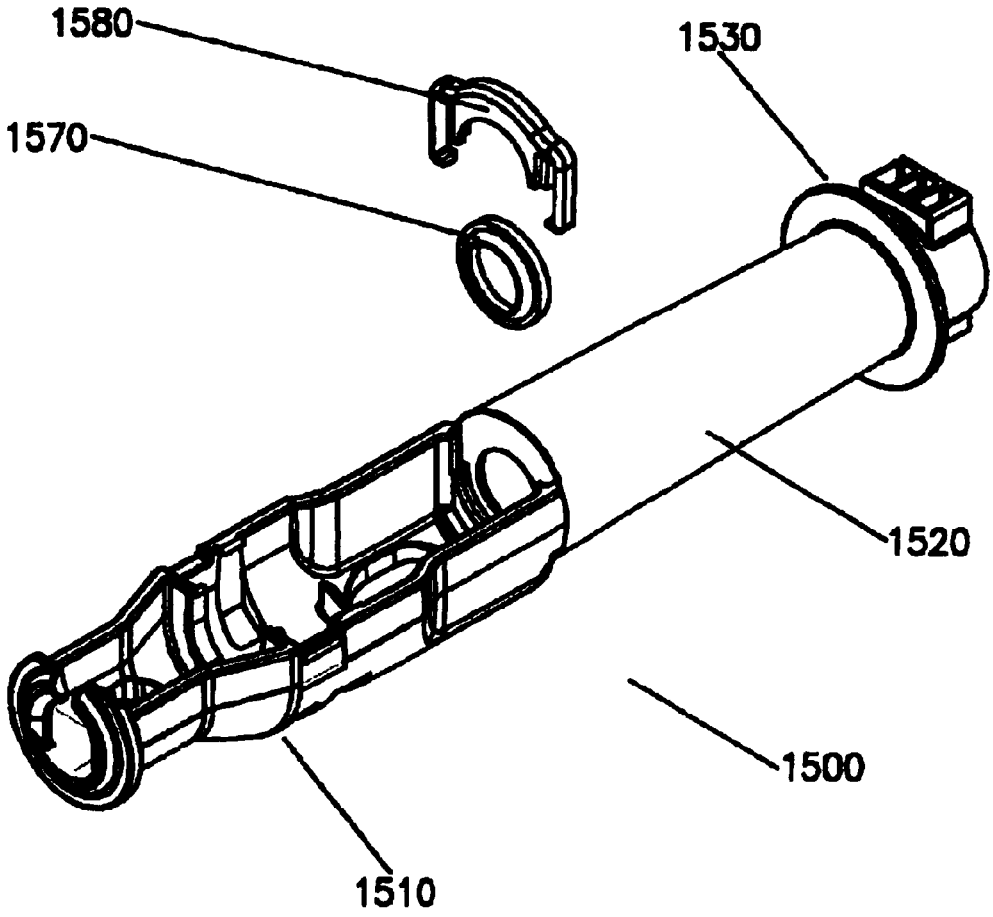
FIG. 12A illustrates a perspective view of an embodiment of an adapter assembly in a disconnected state including a contact or sealing member for removing injection fluids from a push rod.
Figure 12B:
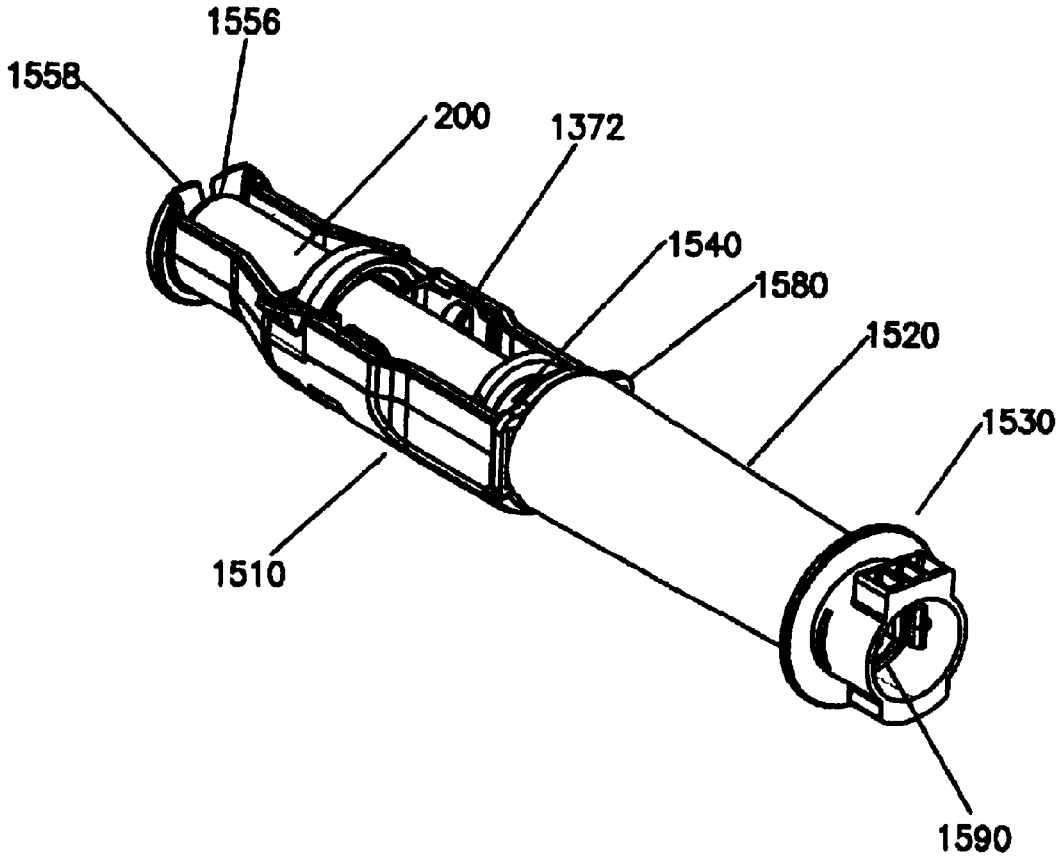
FIG. 12B illustrates a perspective view of the adapter assembly similar to the adapter assembly of FIG. 12A in a connected state.

FIGS. 12A and 12B illustrate an adapter system 1500 that includes a carrier section 1510, an intermediate section 1520 and a connector section 1530 as discussed above. Adapter system 1500 includes a cleaning or contact member such as a wiper seal 1570 and retainer ring 1580 for positioning wiper seal 1570 within adapter system 1500. Wiper seal 1570 operates to remove unwanted contrast media (resulting, for example, from leakage and/or spillage) from push rod 1540. In that regard, as the piston is being retracted following an injection, wiper seal 1570 cleans/wipes any contrast media that has inadvertently adhered to push rod 1540 therefrom. Moreover, wiper seal 1570 also minimize unwanted contrast media from entering the intermediate section 1520 of the adapter system 1520. Retainer 1580 preferably holds wiper seal 1570 in place via a pressure fit in carrier section 1510.

Figure 13A:
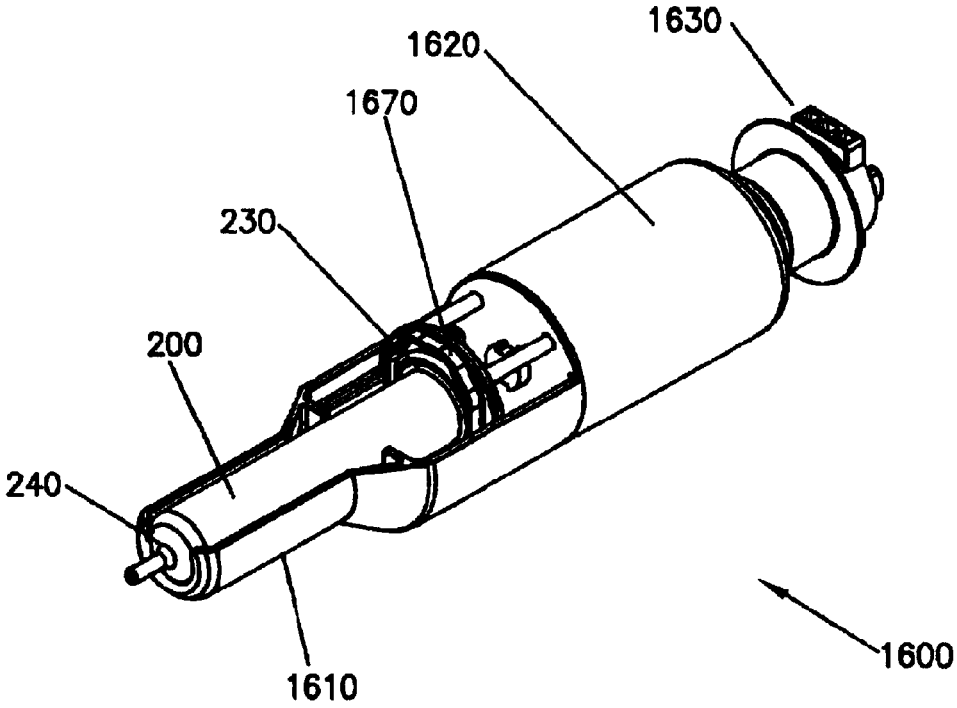
FIG. 13A illustrates a perspective view of an embodiment of an adapter assembly including a biasing member to bias the syringe forward within the carrier section.
Figure 13B:
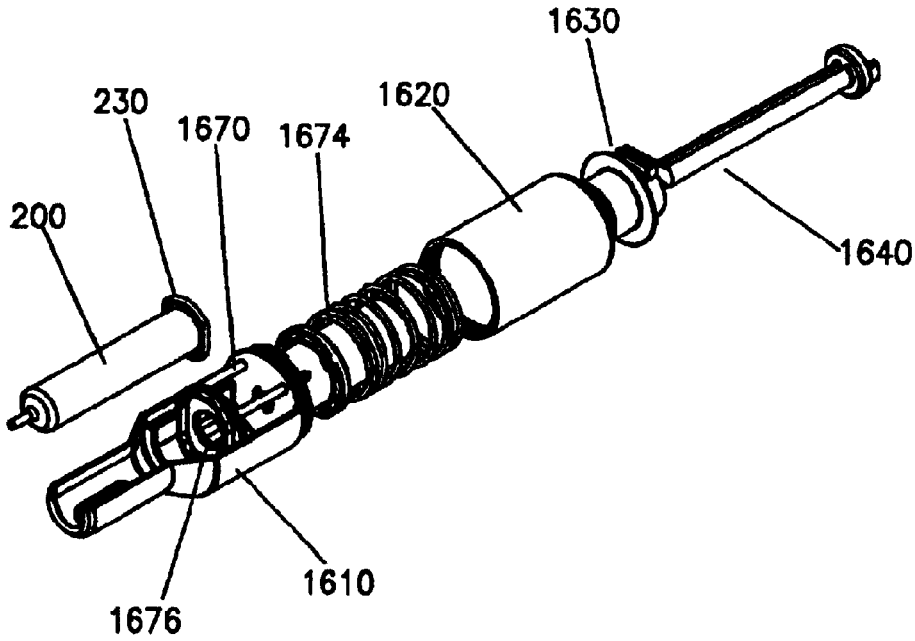
FIG. 13B illustrates a perspective view of the adapter assembly of FIG. 13A in a disconnected state.

As best illustrated in FIG. 12B, push rod 1540 is preferably prevented from being removed from the rear opening of connection section 1330 by a retainer flange 1590 that abuts a flange on the rearward end of push rod 1540 (not shown in FIG. 12B; see push rod 1640 in FIG. 13B). The flange on the rearward end of push rod 1540 is preferably dimensioned to be slightly smaller than the inner diameter of intermediate section 1520. The contact of contact member 1570 with push rod 1540 and the contact of the push rod flange with the inner wall of intermediate section 1520 assist in maintaining proper alignment of push rod 1540 within adapter assembly 1500.

FIGS. 13A and 13B illustrate an adapter system 1600 including a carrier section 1610, an intermediate section 1620, a connector section 1630 and a pushrod 1640. Adapter system 1600 includes a forward-biasing, rear abutment member 1670 that operates to bias syringe 200 completely forward in carrier section 1610 regardless of the length of syringe 200. Abutment member 1670 is preferably slidably positioned at the rear of carrier section 1610 and is biased forward by, for example, a spring 1674 housed within intermediate section 1620. As the operator loads a syringe into carrier section 1610, by initially placing bottom flange 230 of syringe 200 against abutment member 1670, spring 1674 is compressed as required to accommodate various syringe lengths. With spring 1674 compressed, syringe 200 is biased completely forward within carrier section 1610. Abutment member 1670 also preferably includes a generally central passage 1676 formed therethrough to allow pushrod 1640 to impart force to the syringe plunger.

Figure 14:
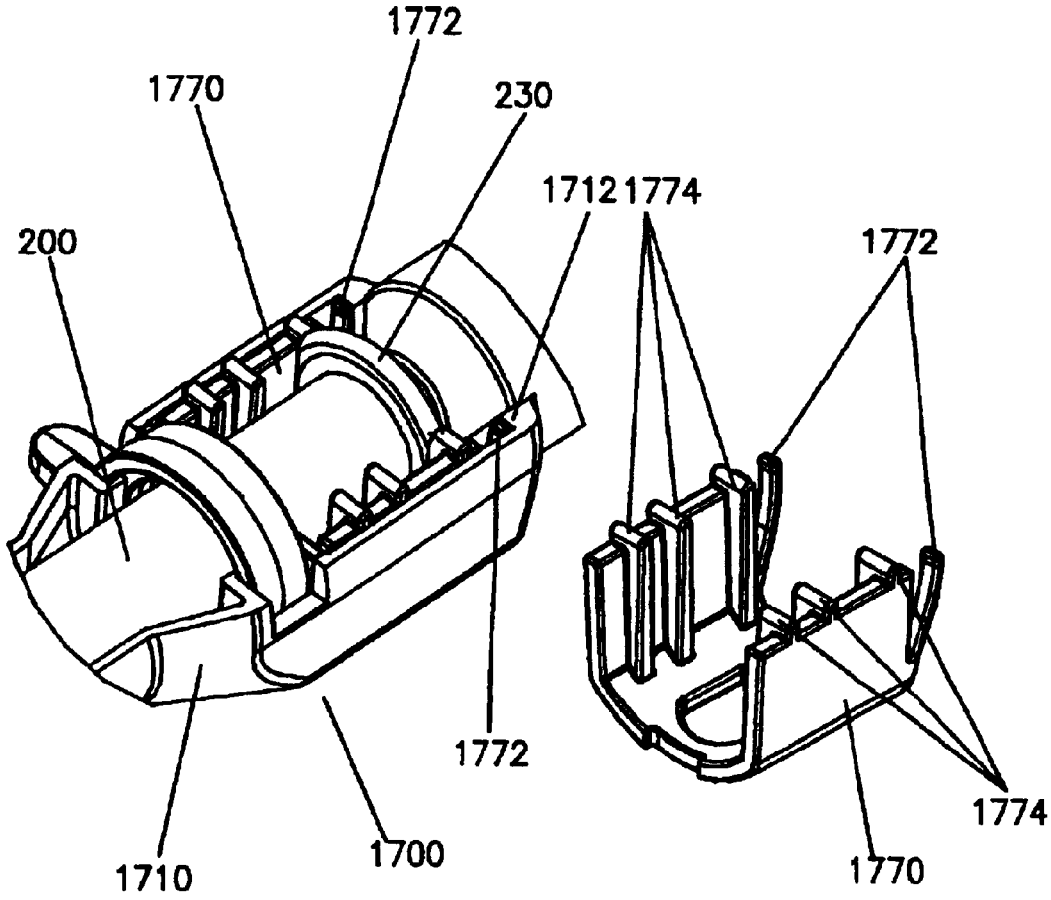
FIG. 14 illustrates a perspective view of another embodiment of a biasing member to bias the syringe forward within the carrier section.

FIG. 14 illustrates another forward biasing abutment member 1770 suitable for use in an adapter system 1700 to bias syringe 200 completely forward within carrier section 1710. Abutment member 1770 is slidably seated within carrier section 1710 and includes flex members 1772 that abut, for example, a forward facing surface 1712 of carrier section 1710 and bias abutment member 1770 forward. Abutment member 1770 of FIG. 14 includes three sets of inward projecting protrusions 1774 for contacting rear flange 230 of syringe 200. Multiple sets of protrusions 1774 are provided to accommodate multiple syringe lengths. Flex members 1772 push against surface 1712 when syringe 200 is in place, thereby biasing syringe 200 in a fully forward position within carrier section 1710 regardless of syringe length.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An adapter for releasably attaching a syringe to an injector, wherein the syringe comprises a body, a cone region attached to a forward end of the body and a plunger slideably positioned within the body, and wherein the injector comprises a front wall, an opening formed in the front wall, and a drive member reciprocally mounted in the injector, the adapter comprising:

a mounting mechanism positioned at a rear of the adapter to mount the adapter in a desired position relative to the front wall of the injector; and a syringe carrier section associated with the mounting mechanism and adapted to seat at least a portion of the syringe, the syringe carrier section defining an opening along a top length thereof to allow placement of the syringe therein from the top, a forward portion of the syringe carrier section comprising two substantially opposed, linear shoulder portions each having first and second ends, the first ends of the shoulder portions being connected by a substantially arcuate member and the second ends of the shoulder portions cooperating to define an opening therebetween, the opposed shoulder portions abutting the cone region of the syringe so that the force exerted by the syringe on the adapter during an injection is generally symmetrical about an axis of the adapter, thereby reducing any bending moment about the mounting mechanism, the syringe carrier section further comprising a rear section defining an opening therein to allow the drive member of the injector to provide forward force to the plunger.

2. The adapter of claim 1 wherein the two substantially opposed shoulder portions are positioned on a first lateral side and a second lateral side, respectively, of the syringe carrier section.

3. The adapter of claim 1 wherein the forward portion of the syringe carrier section further comprises a rib member to strengthen the syringe carrier section.

4. The adapter of claim 1, further comprising an intermediate section operably connected to and disposed between the syringe carrier section and the mounting mechanism.

5. The adapter of claim 4 wherein the syringe carrier section is removably or movably connected to the intermediate section.

6. The adapter of claim 5 wherein the syringe carrier section and the intermediate section are movably connected via pin joints.

7. The adapter of claim 5, further comprising a locking member adapted to lock the syringe carrier section in a closed position.

8. The adapter of claim 4, further comprising a push rod at least partially disposed within the intermediate section for engaging the plunger of the syringe.

9. The adapter of claim 1 wherein the syringe carrier section further comprises a retaining member for retaining the syringe within the syringe carrier section.

10. The adapter of claim 1, further comprising a biasing retaining section operably associated with the syringe carrier section, the biasing retaining section comprising at least one flexible retaining member adapted to engage the syringe body to secure the syringe within the adapter.

11. The adapter of claim 10 wherein the at least one flexible retaining member comprises two retaining members.

12. The adapter of claim 10 wherein the biasing retaining section is removably connected to the syringe carrier section.

13. The adapter of claim 1 wherein the syringe carrier section further comprises at least one flexible retaining member adapted to engage the syringe body to secure the syringe within the adapter.

14. The adapter of claim 13 wherein the at least one flexible retaining member comprises two retaining members.

15. An adapter for releasably attaching a syringe to an injector, wherein the syringe comprises a body, a cone region attached to a forward end of the body and a plunger slideably positioned within the body, and wherein the injector comprises a front wall, an opening formed in the front wall, and a drive member reciprocally mounted in the injector, the adapter comprising:

an intermediate section defining a passage within which a push rod can move to communicate force from the injector drive member to the plunger, a mounting mechanism positioned at a rear end of the intermediate section to mount the adapter in a desired position relative to the front wall of the injector; and a syringe carrier section hingedly connected to a front end of the intermediate section and being adapted to seat at least a portion of the syringe, the syringe carrier section defining a first opening in a rear section thereof to allow the drive member of the injector to communicate forward force to the plunger via the push rod, the syringe carrier section defining a second opening on a top thereof, a forward portion of the syringe carrier section abutting the cone region of the syringe during injection, the syringe carrier section being rotatable relative to the intermediate section to move the forward portion of the syringe carrier section out of contact with the cone region of the syringe to enable removal of the syringe from the adapter without retraction of the drive member.

16. The adapter of claim 15 wherein the forward portion of the syringe carrier section comprises two substantially opposed shoulder portions, the opposed shoulder portions abutting the cone region of the syringe so that the force exerted by the syringe on the adapter during an injection is generally symmetrical about an axis of the adapter, thereby reducing any bending moment about the mounting mechanism.

17. The adapter of claim 16 wherein the two substantially opposed shoulder portions are positioned on a first lateral side and a second lateral side, respectively, of the syringe carrier section.

18. The adapter of claim 15 wherein the forward portion of the syringe carrier section further comprises a rib member to strengthen the syringe carrier section.

19. The adapter of claim 15, further comprising a locking member adapted to lock the syringe carrier section in a closed position.

20. The adapter of claim 15 wherein the syringe carrier section further comprises a retaining member for retaining the syringe within the syringe carrier section.

21. The adapter of claim 15, further comprising a biasing retaining section operably associated with the syringe carrier section, the biasing retaining section comprising at least one flexible retaining member adapted to engage the syringe body to secure the syringe within the adapter.

22. The adapter of claim 21 wherein the at least one flexible retaining member comprises two retaining members.

23. The adapter of claim 21 wherein the biasing retaining section is removably connected to the syringe carrier section.

24. The adapter of claim 15 wherein the syringe carrier section further comprises at least one flexible retaining member adapted to engage the syringe body to secure the syringe within the adapter.

25. The adapter of claim 24 wherein the at least one flexible retaining member comprises two retaining members.

26. An adapter for releasably attaching a syringe to an injector, wherein the syringe comprises a body, a cone region attached to a forward end of the body and a plunger slideably positioned within the body, and wherein the injector comprises a front wall, an opening formed in the front wall, and a drive member reciprocally mounted in the injector, the adapter comprising:

a mounting mechanism positioned at a rear of the adapter to mount the adapter in a desired position relative to the front wall of the injector; and a syringe carrier section adapted to seat at least a portion of the syringe, the syringe carrier section defining an opening on a top thereof to allow placement of the syringe therein from the top, the syringe carrier section comprising an outer wall and at least one flexing retaining member disposed inward from the outer wall, the flexing retaining member adapted to place pressure on at least one side of the syringe to retain the syringe within the syringe carrier section, the syringe carrier section further comprising an opening in a rear section thereof to allow the drive member of the injector to communicate forward force to the plunger.

27. The adapter of claim 26 wherein a forward portion of the syringe carrier section comprises two substantially opposed shoulder portions, the opposed shoulder portions abutting the cone region of the syringe so that the force exerted by the syringe on the adapter during an injection is generally symmetrical about an axis of the adapter, thereby reducing any bending moment about the mounting mechanism.

28. The adapter of claim 27 wherein the two substantially opposed shoulder portions are positioned on a first lateral side and a second lateral side, respectively, of the syringe carrier section.

29. The adapter of claim 27 wherein the forward portion of the syringe carrier section further comprises a rib member to strengthen the syringe carrier section.

30. The adapter of claim 26, further comprising an intermediate section operably connected to and disposed between the syringe carrier section and the mounting mechanism.

31. The adapter of claim 30, further comprising a push rod at least partially disposed within the intermediate section for engaging the plunger of the syringe.

32. The adapter of claim 30, wherein the syringe carrier section is removably or movably connected to the intermediate section.

33. The adapter of claim 32, wherein the syringe carrier section and the intermediate section are movably connected via pin joints.

34. The adapter of claim 32 further comprising a locking member adapted to lock the syringe carrier section in a closed position.

35. The adapter of claim 26 wherein the at least one flexing retaining member comprises two retaining members.

* * * * *